US009289388B2

(12) United States Patent
Guarnieri

(10) Patent No.: US 9,289,388 B2
(45) Date of Patent: Mar. 22, 2016

(54) METHODS AND COMPOSITIONS FOR DELIVERY OF MEDICAMENTS TO THE LUNGS

(75) Inventor: Frank Guarnieri, Brooklyn, NY (US)

(73) Assignee: Paka Pulmonary Pharmaceuticals, Inc., Acton, MA (US)

( * ) Notice: Subject to any disclaimer, the term of this patent is extended or adjusted under 35 U.S.C. 154(b) by 933 days.

(21) Appl. No.: 13/139,154

(22) PCT Filed: Dec. 10, 2009

(86) PCT No.: PCT/US2009/067499
§ 371 (c)(1),
(2), (4) Date: Sep. 23, 2011

(87) PCT Pub. No.: WO2010/068754
PCT Pub. Date: Jun. 17, 2010

(65) Prior Publication Data
US 2012/0010145 A1 Jan. 12, 2012

Related U.S. Application Data

(60) Provisional application No. 61/121,405, filed on Dec. 10, 2008.

(51) Int. Cl.
*A61K 38/00* (2006.01)
*C07K 14/785* (2006.01)
*A61K 9/00* (2006.01)

(52) U.S. Cl.
CPC ............. *A61K 9/0075* (2013.01); *A61K 9/0073* (2013.01)

(58) Field of Classification Search
CPC .......................... A61K 9/0073; A61K 9/0075
See application file for complete search history.

(56) References Cited

U.S. PATENT DOCUMENTS

| 5,006,343 A | 4/1991 | Benson et al. |
| 5,013,720 A | 5/1991 | Whitsett |
| 5,055,553 A | 10/1991 | Jacobs et al. |
| 5,164,369 A | 11/1992 | Cochrane et al. |
| 5,224,183 A | 6/1993 | Dugan |
| 5,238,920 A | 8/1993 | Sarin et al. |
| 5,260,273 A | 11/1993 | Cochrane et al. |
| 5,290,534 A | 3/1994 | Tsao |
| 5,302,581 A | 4/1994 | Sarin et al. |
| 5,320,094 A | 6/1994 | Laube et al. |
| 5,387,746 A | 2/1995 | Whitsett |
| 5,455,227 A | 10/1995 | Curstedt et al. |
| 5,458,135 A | 10/1995 | Patton et al. |
| 5,511,540 A | 4/1996 | Bryant et al. |
| 5,547,937 A | 8/1996 | Dhaon et al. |
| 5,672,581 A | 9/1997 | Rubsamen et al. |
| 5,700,777 A | 12/1997 | Sarin et al. |
| 5,740,794 A | 4/1998 | Smith et al. |
| 5,753,621 A | 5/1998 | Dhaon et al. |
| 5,785,049 A | 7/1998 | Smith et al. |
| 5,861,481 A | 1/1999 | McLean et al. |
| 5,876,970 A | 3/1999 | Benson et al. |
| 5,993,809 A | 11/1999 | Weaver et al. |
| 6,454,140 B1 | 9/2002 | Jinks |
| 6,615,826 B1 | 9/2003 | Gabrio et al. |
| 6,660,833 B1 | 12/2003 | Walther et al. |
| 6,887,845 B2 | 5/2005 | Barron et al. |
| 7,135,452 B1 | 11/2006 | Steinhilber et al. |
| 7,238,664 B2 | 7/2007 | Wollin |
| 2005/0070477 A1 | 3/2005 | Cochrane |
| 2006/0147520 A1 | 7/2006 | Ruegg |
| 2006/0148693 A1 | 7/2006 | Wollin |
| 2006/0234909 A1 | 10/2006 | Newman et al. |
| 2007/0129297 A1 | 6/2007 | Cochrane |
| 2007/0225233 A1 | 9/2007 | Yeh |
| 2010/0284969 A1 | 11/2010 | Guarnieri |
| 2014/0378383 A1* | 12/2014 | Guarnieri ............. A61K 9/0073 514/15.5 |

FOREIGN PATENT DOCUMENTS

| DE | 3229179 A1 | 2/1984 |
| EP | 0100910 A2 | 2/1984 |
| EP | 0110498 A1 | 6/1984 |
| EP | 0119056 A2 | 9/1984 |
| EP | 0145005 A2 | 6/1985 |
| EP | 0251449 A2 | 1/1988 |
| EP | 0286011 A2 | 10/1988 |
| EP | 0335133 A2 | 10/1989 |
| EP | 0348967 A2 | 1/1990 |
| EP | 0368823 A2 | 5/1990 |

(Continued)

OTHER PUBLICATIONS

Beers et al., "Differential extraction for the rapid purification of bovine surfactant protein B," *Am. J. Physiol Lung Cell* 262: L773-L778, 1992.
Bernhard et al., "Conductive Airway Surfactant: Surface-tension Function, Biochemical Composition, and Possible Aleolar Origin," *Am. J. Respir. Cell Mol. Biol.*, vol. 17, pp. 41-50, 1997.
Bernhard, et al., "Phosphatidylcholine Molecular Species in Lung Surfactant Composition in Relation to Respiratory Rate and Lung Development," *A. J. Respir. Cell Mol. Biol.*, vol. 25, pp. 725-731, 2001.
Brackenbury et al., "Evaluation of Exogenous Surfactant in HCl-Induced Lung Injury," *Am J. Respir. Crit. Care Med.*, vol. 163, pp. 1135-1142, 2001.
Broadbent et al., "Chest position and pulmonary deposition of surfactant in surfactant depleted rabbits," *Archives of Disease in Childhood*, vol. 72, No. 2 Suppl., pp. F84-F89, 1995 GB.
Buhl and Farmer, "Current and Future Pharmacologic Therapy of Exacerbations in Chronic Obstructive Pulmonary Disease and Asthma," *Proc. Am.Thorac.Soc.*, vol. 1, pp. 136-142, 2004.

(Continued)

*Primary Examiner* — Marcela M Cordero Garcia
(74) *Attorney, Agent, or Firm* — Goodwin Procter LLP

(57) ABSTRACT

The disclosure provides a drug composition formulated for inhalation comprising a conjugate of a surface active agent and a pulmonary active drug. The surface active agent has an affinity for the human alveolar/gas interface and comprises at least a portion of a mammalian lung surfactant of a mimic thereof. The disclosure also provides a method of treating a subject suffering from or at risk of suffering from a lung disease comprising administering to the subject a conjugate comprising a drug for lung treatment and a surface active agent by inhalation in an amount effective to induce a drug effect in the lungs.

28 Claims, 29 Drawing Sheets

(56) References Cited

FOREIGN PATENT DOCUMENTS

| EP | 0593094 A2 | 4/1994 |
|---|---|---|
| WO | WO-8603408 A1 | 6/1986 |
| WO | WO-8706943 A1 | 11/1987 |
| WO | WO-8803170 A1 | 5/1988 |
| WO | WO-8904326 A1 | 5/1989 |
| WO | WO-90/01540 A1 | 2/1990 |
| WO | WO-9108871 A2 | 6/1991 |
| WO | WO-9118015 A1 | 11/1991 |
| WO | WO-9222315 A1 | 12/1992 |
| WO | WO-9532992 A1 | 12/1995 |
| WO | WO-96/30051 A1 | 10/1996 |
| WO | WO-9726863 A1 | 7/1997 |
| WO | WO-9735882 A1 | 10/1997 |
| WO | WO-0117568 A2 | 3/2001 |
| WO | WO-03/011316 A1 | 2/2003 |
| WO | WO-03/090682 A2 | 11/2003 |
| WO | WO-03105775 A2 | 12/2003 |
| WO | WO-2004/011613 A2 | 2/2004 |
| WO | WO-2005/055994 A1 | 6/2005 |
| WO | WO-2005/059142 A1 | 6/2005 |
| WO | WO-2006/108563 A1 | 10/2006 |
| WO | WO-2007/005672 A2 | 1/2007 |
| WO | WO-2007/102690 A1 | 9/2007 |
| WO | WO-2008/151235 A2 | 12/2008 |
| WO | WO-2008/157263 A2 | 12/2008 |
| WO | WO-2009/007120 A2 | 1/2009 |
| WO | WO-2009/104013 A1 | 8/2009 |
| WO | WO-2010/068754 A2 | 6/2010 |

OTHER PUBLICATIONS

Deterding et al., "Safety and Tolerability of Denufosol Tetrasodium Inhalation Solution, a Novel P2Y$_2$ Receptor Agonist: Results of a Phase 1/Phase 2 Multicenter Study in Mild to Moderate Cystic Fibrosis," *Pediatric Pulmonology*, vol. 39, pp. 339-348, 2005.

Deterding et al., "Phase 2 Randomized Safety and Efficacy Trial of Nebulized Denufosol Tetrasodium in Cystic Fibrosis," *Am. J. Respir. Crit. Care Med.*, vol. 176, pp. 362-369, 2007.

Diemal et al., "In vitro and in vivo intrapulmonary distribution of fluorescently labeled surfactant," *Critical Care Medicine*, vol. 30, No. 5, pp. 1083-1090, 2002.

Edwards and Bernstein, "Synthetic Inhibitors of Elastase," *Medicinal Research Reviews*, vol. 14, No. 2, 127-194, 1994.

Edwards et al., "Corticosteroids and B$_2$ Agonists Differentially Regulate Rhinovirus Induced IL-6 Via Distinct CIS-Acting Elements," *J. Biol Chem*, pp. 1-21, 2007.

Fok et al., "Nebulisation of surfactants in an animal model of neonatal respiratory distress," *Archives of Disease in Childhood: Fetal and Neonatal Edition*, vol. 78, No. 1, pp. F3-F9, 1998 GB.

Gazdar and Minna, "Deregulated EGFR Signaling During Lung Cancer Progression: Mutations, Amplicons, and Autocrine Loops," *Cancer Prev. Res.*, 2008;1(3) Aug. 2008, pp. 156-160.

Goss et al., "Experience using centralized spirometry in the phase 2 randomized, placebo-controlled, double-blind trial of denufosol in patients with mild to moderate cystic fibrosis," *Journal of Cystic Fibrosis*, vol. 7, pp. 147-153, 2008.

Günther et al., "Bronchoscopic administration of bovine natural surfactant in ARDS and septic shock: impact on biophysical and biochemical surfactant properties," *Eur. Respir. J.* , 19, pp. 797-804, 2002.

Günther, "Aerosolized Urokinase in Pulmonary Fibrosis," *American Journal of Respiratory and Critical Care Medicine*, vol. 169, pp. 1258-1259, 2004.

Kellerman et al., "Inhaled P2Y$_2$ receptor agonists as a treatment for patients with Cystic Fibrosis lung disease," *Advanced Drug Delivery Reviews*, vol. 54, pp. 1463-1474, 2002.

Kuramoto et al., "Inhalation of urokinase-type plasminogen activator reduces airway remodeling in a murine asthma model," *Am. J. Physiol. Lung Cell Mol. Physiol.* 296: L337-L346, 2009.

Kurutz and Lee, NMR Structure of Lung Surfactant Peptide SP-B$_{11-25}$, *Brochemistry* 41, 9627-36, 2002.

Leuchte et al., "Inhalation of endothelin receptor blockers in pulmonary hypertension," *Am. J. Physiol. Lung Cell Mol. Physiol.* 294: L772-L777, 2008.

Lu et al., "An oral selective M3 cholinergic receptor antagonist in COPD," *Eur Respir J*, 28: 772-780, 2006.

McGraw et al., "Crosstalk between G$_i$ and G$_q$/G$_s$ pathways in airway smooth muscle regulates bronchial contractility and relaxation," *The Journal of Clinical Investigation*, vol. 117, No. 5, pp. 1391-1398, 2007.

Mokrousov et al., "Mycobacterium tuberculosis co-existence with humans: making an imprint on the macrophage P2X$_7$ receptor gene?" *Journal of Medical Microbiology*, vol. 57, pp. 581-584, 2008.

Patent Cooperation Treaty (PCT) International Search Report; International Application No. PCT/US2008/065776, mailed on Feb. 5, 2009.

Patent Cooperation Treaty (PCT) International Search Report; International Application No. PCT/US2009/067499, mailed on Aug. 19, 2010.

Patent Cooperation Treaty (PCT) International Search Report; International Application No. PCT/US2010/049307, mailed on Mar. 2, 2011.

Penugonda et al., "Synthesis and in Vitro Characterization of Novel Dextran-Methylprednisolone Conjugates with Peptide Linkers: Effects of Linker Length on Hydrolytic and Enzymatic Release of Methylprednisolone and its Peptidyl Intermediates," *J Pharm Sci.*; 97(7): 2649-2664, 2008.

Ruppert et al., "Recombinant production of a hybrid plasminogen activator composed of surfactant protein B and low-molecular-weight urokinase," *Thromb Haemost*, 100: 1185-92, 2008.

Shaver et al., "Structure-activity relationships of dinucleotides: Potent and selective agonists of P2Y receptors," *Purinergic Signaling*, vol. 1, pp. 183-191, 2005.

Som et al., "Synthetic Mimics of Antimicrobial Peptides," *Peptide Science*, vol. 90, No. 2, pp. 83-93, 2008.

Yerxa et al., "Pharmacology of INS37217 [P$^1$-(Uridine 5')-P$^4$-(2'-deoxycytidine 5')tetraphosphate, Tetrasodium Salt], a Next-Generation P2Y$_2$ Receptor Agonist for the Treatment of Cystic Fibrosis," *The Journal of Pharmacology and Experimental Therapeutics*, vol. 302, No. 3, pp. 871-880, 2002.

Zhou et al., "Targeting ADAM-mediated ligand cleavage to inhibit HER3 and EGFR pathways in non-small cell lung cancer," *Cancer Cell*, vol. 10, pp. 39-50, 2006.

Akinbi, et al., "Rescue of SP-B Knockout Mice with a Truncated SP-B Proprotein Function of the C-Terminal Propeptide," *The Journal of Biological Chemistry*, vol. 272, pp. 9640-9647, 1997.

Baatz, et al., "Utilization of modified surfactant-associated protein B for delivery of DNA to airway cells in culture," *Proc. Natl. Acad. Sci. USA*, vol. 91, pp. 2547-2551, 1994.

Hartshorn et al., "Enhanced anti-influenza activity of a surfactant protein D and serum conglutinin fusion protein," *Am. J. Physiol. Lung Cell. Mol. Physiol.* 278: L90-L98, 2000.

Kabore et al., "Biosynthesis of surfactant protein C: characterization of aggresome formation by EGFP chimeras containing propeptide mutants lacking conserved cysteine residues," *Journal of Cell Science*, vol. 114, pp. 293-302.

Lin et al., "Structural Requirements for Targeting of Surfactant Protein B (SP-B) to Secretory Granules in Vitro and in Vivo," *The Journal of Biological Chemistry*, vol. 271, pp. 19689-19695, 1996.

Palacios et al., "Production of a recombinant form of the propeptide NH$_2$-terminal of the precursor of pulmonary surfactant protein B," *Enzyme and Microbial Technology*, vol. 40, pp. 85-92, 2006.

Ross et al., "Surfactant Protein A-Polylysine Conjugates for Delivery of DNA to Airway Cells in Culture," *Human Gene Therapy*, vol. 6, pp. 31-40, 1995.

Ruppert et al., "Chemical crosslinking of urokinase to pulmonary surfactant protein B for targeting alveolar fibrin," *Thromb Haemost*, vol. 89, pp. 53-64, 2003.

Tacken et al., "Effective Targeting of Pathogens to Neutrophils via Chimeric Surfactant Protein D/Anti-CD89 Protein[1]," *The Journal of Immunology*, vol. 172, pp. 4934-4940, 2004.

Wang et al., "Deletion of exon 4 from human surfactant protein C results in aggresome formation and generation of a dominant negative," *Journal of Cell Science*, vol. 116, pp. 683-692, 2003.

(56) References Cited

OTHER PUBLICATIONS

White et al., "Enhanced Antiviral and Opsonic Activity of a Human Mannose-Binding Lectin and Surfactant Protein D Chimeras," *The Journal of Immunology*, vol. 165, pp. 2108-2115, 2000.

White et al., "Increased Antiviral and Opsonic Activity of a Highly Multimerized Collectin Chimera," *Biochemical and Biophysical Research Communications*, vol. 286, pp. 206-213 (2001).

\* cited by examiner

Figure 1

A.
```
1    ccaagcagct ggaggctctg tgtgtgggtc gctgatttct tggagcctga aaagaaagta
61   acacagcagg gatgaggaca gatggtgtga gtcagtgaga gcagcgactg gacccagagc
121  catgtggctg tgccctctgg ccctcaacct catcttgatg gcagcctctg gtgctgtgtg
181  cgaagtgaag gacgtttgtg ttggaagccc tggtatcccc ggcactcctg gatcccacgg
241  cctgccaggc agggacggga gagatggtct caaaggagac cctggccctc caggccccat
301  gggtccacct ggagaaatgc catgtcctcc tggaaatgat gggctgcctg gagcccctgg
361  tatccctgga gagtgtggag agaaggggga gcctggcgag aggggccctc cagggcttcc
421  agctcatcta tgatgaggag ctccaagccac actccacgac tttagacatc aaatcctgca
481  gacaagggga gccctcagtc tgcagggctc cataatgaca gtaggagaga aggtcttctc
541  cagcaatggg cagtccatca cttttgatgc cattcaggag gcatgtgcca gagcaggcgg
601  ccgcattgct gtcccaagga atccagagga aaatgaggcc attgcaagct cgtgaagaa
661  gtacaacaca tatgcctatg taggcctgac tgagggtccc agccctggag acttccgcta
721  ctcagacggg accccgtaa actacaccaa ctggtaccga ggggagcccg caggtcgggg
781  aaaagagcag tgtgtggaga tgtacacaga tgggcagtgg aatgacagga actgcctgta
841  ctcccgactg accatctgtg agttctgaga ggcatttagg ccatgggaca ggggaggacgc
901  tctctggcct tcggcctcca tcctgaggct ccacttggtc tgtgagatgc tagaactccc
961  tttcaaca
```
(SEQ ID NO: 1)

B.
MWLCPLALNLILMAASGAVCEVKDVCVGSPGIPGTPGSHGLPGRDGRDGLKGDPGPPGPMGPPG
EMPCPPGNDGLPGAPGIPGECGEKGEPGERGPPGLPAHLDEELQATLHDFRHQILQTRGALSLQ
GSIMTVGEKVFSSNGQSITFDAIQEACARAGGRIAVPRNPEENEAIASFVKKYNTYAYVGLTEG
PSPGDFRYSDGTPVNYTNWYRGEPAGRGKEQCVEMYTDGQWNDRNCLYSRLTICEF
(SEQ ID NO: 2)

Figure 2

A.
```
1    gccatggctg agtcacacct gctgcagtgg ctgctgctgc tgctgcccac gctctgtggc
61   ccaggcactg ctgcctggac cacctcatcc ttggcctgtg cccagggccc tgagttctgg
121  tgccaaagcc tggagcaagc attgcagtgc agagccctag ggcattgcct acaggaagtc
181  tggggacatg tgggagccga tgacctatgc aagagtgtg aggacatcgt ccacatcctt
241  aacaagatgg ccaaggaggc cattttccag gacacgatga ggaagttcct ggagcaggag
301  tgcaacgtcc tccccttgaa gctgctcatg ccccagtgca accaagtgct gacgactac
361  ttcccctgg tcatcgacta cttccagaac cagactgact caaacggcat ctgtatgcac
421  ctgggcctgt gcaaatcccg cagccagag ccagagcagg agccagggat gtcagacccc
481  ctgcccaaac ctctgcggga ccctctgcca gaccctctgc tggacaagct cgtcctccct
541  gtgctgcccg gggccctcca ggcgaggcct gggcctcaca caggatct ctccgagcag
601  caattcccca ttcctctccc ctattgctgg ctctgcaggg ctctgatcaa gcggatccaa
661  gccatgattc ccaagggtgc gctagctgtg gcagtggccc aggtgtgccg cgtggtacct
721  ctggtggcgg gcggcatctg ccagtgcctg gctgagcgct actccgtcat cctgctcgac
781  acgctgctgg gccgcatgct gccccagctg gtctgccgcc tcgtcctccg gtgctccatg
841  gatgacagcg ctggcccaag gtcgccgaca ggagaatggc tgccgcgaga ctctgagtgc
901  cacctctgca tgtccgtgac cacccaggcc gggaacagca gcgagcaggc cataccacag
961  gcaatgctcc aggcctgtgt tggctcctgg ctggacaggg aaaagtgcaa gcaatttgtg
1021 gagcagcaca cgccccagct gctgaccctg gtgccaggg gctgggatgc cacaccacc
1081 tgccaggccc tcggggtgtg tgggaccatg tccagccctc tccagtgtat ccacagcccc
1141 gacctttgat gagaactcag ctgtccagct gcaaaggaaa agccaagtga gacgggctct
1201 gggaccatgg tgaccaggct cttccctgc tccctggccc tcgccagctg ccaggctgaa
1261 aagaagcctc agctcccaca ccgccctcct caccgccctt cctcggcagt cacttccact
1321 ggtggaccac gggcccccag ccctgtgtcg gccttgtctg tctcagctca accacagtct
1381 gacaccagag cccacttcca tcctctctgg tgtgaggcac agcgagggca gcatctggag
1441 gagctctgca gcctccacac ctaccacgac ctcccagggc tgggctcagg aaaaaccagc
1501 cactgcttta caggacaggg ggttgaagct gagccccgcc tcacacccac ccccatgcac
1561 tcaaagattg gatttacag ctacttgcaa ttcaaaattc agaagaataa aaaatgggaa
1621 catacagaac tctaaaagat agacatcaga aattgttaag ttaagctttt tcaaaaaatc
1681 agcaattccc cagcgtagtc aagggtggac actgcacgct ctggcatgat gggatggcga
1741 ccgggcaagc tttcttcctc gagatgctct gctgcttgag agctattgct ttgttaagat
1801 ataaaaaggg gtttcttttt gtctttctgt aaggtggact tccagctttt gattgaaagt
1861 cctagggtga ttctatttct gctgtgattt atctgctgaa agctcagctg gggttgtgca
1921 agctagggac ccattcctgt gtaatacaat gtctgcacca atgctaataa agtcctattc
1981 tcttttatga aaaaaaaaa aaaaaaaaa aaaaaaaaaa aaaaaa
```
(SEQ ID NO: 3)

B.
MAESHLLQWLLLLLPTLCGPGTAAWTTSSLACAQGPEFWCQSLEQALQCRALGHCLQEVWGHVG
ADDLCQECEDIVHILNKMAKEAIFQDTMRKFLEQECNVLPLKLLMPQCNQVLDDYFPLVIDYFQ
NQTDSNGICMHLGLCKSRQPEPEQEPGMSDPLPKPLRDPLPDPLLDKLVLPVLPGALQARPGPH
TQDLSEQQFPIPLPYCWLCRALIKRIQAMIPKGALAVAVAQVCRVVPLVAGGICQCLAERYSVI
LLDTLLGRMLPQLVCRLVLRCSMDDSAGPRSPTGEWLPRDSECHLCMSVTTQAGNSSEQAIPQA
MLQACVGSWLDREKCKQFVEQHTPQLLTLVPRGWDAHTTCQALGVCGTMSSPLQCIHSPDL
(SEQ ID NO: 4)

C.
FPIPLPYCWLCRALIKRIQAMIPKGALAVAVAQVCRVVPLVAGGICQCLAERYSVILLDTLLGR
MLPQLVCRLVLRCSM
(SEQ ID NO: 5)

Figure 3

A.
```
1    cttatctcgg cttcgtttct ggagggccag gaacaaacag gcttcaaagc caagggcttg
61   gctggcacac aggggggcttg gtccttcacc tctgtccccct ctccctacgg acacatataa
121  gaccctggtc acacctggga gaggaggaga ggagagcata gcacctgcag caagatggat
181  gtgggcagca aagaggtcct gatggagagc ccgccggact actccgcagc tccccggggc
241  cgatttggca ttccctgctg cccagtgcac ctgaaacgcc ttcttatcgt ggtggtggtg
301  gtggtcctca tcgtcgtggt gattgtggga gccctgctca tgggtctcca catgagccag
361  aaacacacgg agatggttct ggagatgagc attggggcgc cggaagccca gcaacgcctg
421  gccctgagtg agcacctggt taccactgcc accttctcca tcggctccac tggcctcgtg
481  gtgtatgact accagcagct gctgatcgcc tacaagccag ccctggcac ctgctgctac
541  atcatgaaga tagctccaga gagcatcccc agtcttgagg ctctcaatag aaaagtccac
601  aacttccaga tggaatgctc tctgcaggcc aagcccgcag tgcctacgtc taagctgggc
661  caggcagagg ggcgagatgc aggctcagca ccctccggag gggacccggc cttcctgggc
721  atggccgtga acaccctgtg tggcgaggtg ccgctctact acatctagga cgcctccggt
781  gagcagggtc agtggaagcc caacgggaa aggaaacgcc ccgggcaaag ggtctttttgc
841  agcttttgca gacgggcaag aagctgcttc tgcccacacc gcagggacaa accctggaga
901  aatgggagct tggggagagg atgggagtgg gcagaggtgg cacccagggg cccgggaact
961  cctgccacaa cagaataaag cagcctgatt g
```
(SEQ ID NO: 6)

B.
MDVGSKEVLMESPPDYSAAPRGRFGIPCCPVHLKRLLIVVVVVVLIVVVIVGALLMGLHMSQKH
TEMVLEMSIGAPEAQQRLALSEHLVTTATFSIGSTGLVVYDYQQLLIAYKPAPGTCCYIMKIAP
ESIPSLEALNRKVHNFQMECSLQAKPAVPTSKLGQAEGRDAGSAPSGGDPAFLGMAVNTLCGEV
PLYYI
(SEQ ID NO: 7)

C.
FGIPCCPVHLKRLLIVVVVVVLIVVVIVGALLMGLHMSQKHTEMVLEMSIGAPEAQQRLALSEH
LVTTATFSIGSTGLVVYDYQQLLIAYKPAPGTCCYIMKIAPESIPSLEALNRKVHNFQMECSLQ
AKPAVPTSKLGQAEGRDAGSAPSGGDPAFLGMAVNTLCGEVPLYYI (SEQ ID NO: 8)

```
1    agtttgcttg gagctcctgg ggcctaacaa aaagaaacct gccatgctgc tcttcctcct
61   ctctgcactg gtcctgctca cacagcccct gggctacctg gaagcagaaa tgaagaccta
121  ctcccacaga acaatgccca gtgcttgcac cctggtcatg tgtagctcag tggagagtgg
181  cctgcctggt cgcgatggac gggatgggag agagggccct cggggcgaga aggggggaccc
241  aggtttgcca ggagctgcag ggcaagcagg gatgcctgga caagctggcc cagttgggcc
301  caaaggggac aatggctctg ttggagaacc tggaccaaag ggagacactg gccaagtgg
361  acctccagga cctcccggtg tgcctggtcc agctggaaga aaggtcccc tggggaagca
421  ggggaacata ggacctcagg gcaagccagg cccaaaagga gaagctgggc ccaaaggaga
481  agtaggtgcc ccaggcatgc agggctcggc aggggcaaga ggcctcgcag gccctaaggg
541  agagcgaggt gtccctggtg agcgtggagt ccctggaaac acaggggcag cagggtctgc
601  tggagccatg ggtccccagg gaagtccagg tgccagggga ccccgggat tgaagggga
661  caaaggcatt cctggagaca aaggagcaaa gggagaaagt gggcttccag atgttgcttc
721  tctgaggcag caggttgagg ccttacaggg acaagtacag cacctccagg ctgctttctc
781  tcagtataag aaagttgagc tcttcccaaa tggccaaagt gtcggggaga agattttcaa
841  gacagcaggc tttgtaaaac catttacgga ggcacagctg ctgtgcacac aggctggtgg
901  acagttggcc tctccacgct ctgccgctga aatgccgcc ttgcaacagc tggtcgtagc
961  taagaacgag gctgctttcc tgagcatgac tgattccaag acagagggca agttcaccta
1021 ccccacagga gagtccctgg tctattccaa ctgggcccca ggggagccca acgatgatgg
1081 cgggtcagag gactgtgtgg agatcttcac caatggcaag tggaatgaca gggcttgtgg
1141 agaaaagcgt cttgtggtct gcgagttctg agccaactgg ggtgggtggg gcagtgcttg
1201 gcccaggagt ttggccagaa gtcaaggctt agaccctcat gctgccaata tcctaataaa
1261 aaggtgacca tctgtgccgg gaaaaaaaaa aaaaaaaaa
```
(SEQ ID NO: 9)

B.

MLLFLLSALVLLTQPLGYLEAEMKTYSHRTMPSACTLVMCSSVESGLPGRDGRDGREGPRGEKG
DPGLPGAAGQAGMPGQAGPVGPKGDNGSVGEPGPKGDTGPSGPPGPPGVPGPAGREGPLGKQGN
IGPQGKPGPKGEAGPKGEVGAPGMQGSAGARGLAGPKGERGVPGERGVPGNTGAAGSAGAMGPQ
GSPGARGPPGLKGDKGIPGDKGAKGESGLPDVASLRQQVEALQGQVQHLQAAFSQYKKVELFPN
GQSVGEKIFKTAGFVKPFTEAQLLCTQAGGQLASPRSAAENAALQQLVVAKNEAAFLSMTDSKT
EGKFTYPTGESLVYSNWAPGEPNDDGGSEDCVEIFTNGKWNDRACGEKRLVVCEF (SEQ ID NO: 10)

C.

AEMKTYSHRT MPSACTLVMC ·SSVESGLPGR DGRDGREGPR GEKGDPGLPG
AAGQAGMPGQ AGPVGPKGDN GSVGEPGPKG DTGPSGPPGP PGVPGPAGRE
GPLGKQGNIG PQGKPGPKGE AGPKGEVGAP GMQGSAGARG LAGPKGERGV
PGERGVPGNT GAAGSAGAMG PQGSPGARGP PGLKGDKGIP GDKGAKGESG
LPDVASLRQQ VEALQGQVQH LQAAFSQYKK VELFPNGQSV GEKIFKTAGF
VKPFTEAQLL CTQAGGQLAS PRSAAENAAL QQLVVAKNEA AFLSMTDSKT
EGKFTYPTGE SLVYSNWAPG EPNDDGGSED CVEIFTNGKW NDRACGEKRL VVCEF (SEQ ID NO: 11)

Figure 5

A.
```
1    ggctatggag gcagggagca tgggctgtgt tcgtgcagga ggagctgctg gagcaggcgc
61   catgctgctg tgctctttga cccttacgct cctctggatg gtggcttctg gcctcgagtg
121  cgatgtcaag gaagtttgtc ttggaagccc tggcattcct ggcactcctg gatcccatgg
181  cctgccagga agagatggga gagatggtat caaaggagac cctgggcctc caggccccat
241  gggccccct ggaggaatgc caggcctccc tgggcgtgat gggatgactg gagcccctgg
301  cctccctgga gagcgtggag aaaagggaga gcctggcgag agaggtcctc cagggtttcc
361  agcatatcta gatgaagagc tccagggcac actccatgag atcagacatc aagtcctgca
421  gtcacagggc gtcctccgtt tgcaggggtc cgtgctggcg gtgggagaga aggtcttctc
481  taccaatggg cagtcagtca attttgatgc cattaaagag ttatgtgcca gagtaggtgg
541  acatattgct gccccgagga gtccagagga gaatgaagcc attgtgagca tcgtgaagaa
601  gtacaacact tatgcttacc tgggcctggt cgaaggcccc accgctggag acttctatta
661  cctggatgga gcccctgtga attataccaa ttggtaccca ggggagccca ggggccgggg
721  taaagagaag tgtgtagaaa tatacacaga tggtcagtgg aatgacaaga actgcctgca
781  gtaccgactg gccatctgtg agttctgagc aggcaccaaa gccacaggat ggacacagtc
841  ctatctttcc ttttagcctc catcctgggg atccacctgg tctatgaatc aggtgctata
901  attcccttgt ggctatcaga attgaaggca ctcttgagca ctccactcct gggtggatcc
961  tgactcctcc ccaatgatca ctaatcagtc tgactccccc agaacccctt ctcagcattg
1021 cactcttggc agccactcta actttgccct tctgcaagag acagaggttt ctttcctcct
1081 tttcttgtcc agttccttta tttatagatg gcaacagtaa ggtcctgaga tgaaggttcc
1141 ctccacagca ccacactgcc tacttcctgg ccccctcta tctgtctttt gcagctcact
1201 gcttgcccag cctcatcaag atttagcagt gctgctcaag cacaatgata gatgtacttc
1261 tgggaaattt cacatgtgtg gagctaagga tacatttggg tttatctatc aacctgagat
1321 ctgtggggag gcatcttgtt aggctctcca tgaagtcaga gggccaggtg gtgctccagc
1381 atgatggaag ccaacttatt cctagtgatt ggcaggtatt atccacttcc ttgagtctta
1441 gggtgtcagc caacacctct aaggaagatg tcaccccac catagacatt acccaagtac
1501 ctgcctgctg atgaacacat tccccacctc ttcagaaatc agtgaggagt tcacgctcct
1561 tgtcacacca ccgtttattg agcacatact atataccaag caccgtgaca tgcacttcta
1621 agacatatga tttaatcttc acacagtgtc atgggatgag catcattttc cccaatcttt
1681 tatacaagga cactgaaatt tagagaagtt aaatgttttg cattttttt tttttaacat
1741 gaagcaattg gcagaggctg gtttcaaacc catctacctg gacctaaagc ttgtgctcat
1801 aattacctct ccttctcatt gaacagagat gattcacgtg taataaatca tgaatgtgtt
1861 aaaaaaaaaa aaaaaaaata aaaaaaaaaa aaaaaaaaaa aaaaaaaaaa aaaaaaaaaa
1921 aaaaaaaaaa aaaaaaaaaa aaaaaaaaaa aaaaaaaaaa aaaaaaaaaa aaaaaaaaaa
1981 aaaaaaaaaa aaaaaaaaaa aaaaaaaaaa aaaaaaaaaa aaaaaaaaaa aaaaaaa
```
(SEQ ID NO: 12)

B.
MLLCSLTLTLLWMVASGLECDVKEVCLGSPGIPGTPGSHGLPGRDGRDGIKGDPGPPGPMGPPG
GMPGLPGRDGMTGAPGLPGERGEKGEPGERGPPGFPAYLDEELQGTLHEIRHQVLQSQGVLRLQ
GSVLAVGEKVFSTNGQSVNFDAIKELCARVGGHIAAPRSPEENEAIVSIVKKYNTYAYLGLVEG
PTAGDFYYLDGAPVNYTNWYPGEPRGRGKEKCVEIYTDGQWNDKNCLQYRLAICEF
(SEQ ID NO: 13)

Figure 6

A.
```
1    ggtccaggct gtggaggtgc catggccaag tcacacctgc ttccatggct tctgctgctg
61   cccatactct gtggtccggg cactgctgct gcgatcacct attccctggc ctgtgcccag
121  ggccccgagt tctggtgtca agtctggag  caagcattgc agtgcagagc ctagggcac
181  tgcctgcagg aagtctgggg acatgtggaa gccgatgacc tgtgccagga atgtgagaac
241  atctcccgcc tcctcaccaa gatggccaag gaggccattt tccaggactc agtgcgcaaa
301  tttctggagc aggagtgcga tgtccttccg ctgaaactgt tggcgcccct gtgtcgccac
361  ctgctggaca cctatttccc tctgatcatt gagcacttcc agagccatat gaacccgaag
421  ttcatctgtc agcacgtggg cctatgcaag cccaggcacc cagagccagg gaaggggcca
481  gagccatggg gccctctgct ggacaagctg gccctccccc tgctgccagg ggtcccccag
541  gccaagcctg ggcctcagac acaggacctc tctgagcagc tgttccccat tcccatcccc
601  tactgctggc tctgccggac tctgatcaaa cggatccagg ctgtgattcc caagggtgtt
661  ctggccatga ctgtggccca ggtgtgccac gtggtccccc tgctggtggg cggcatctgc
721  cagtgcctgg ttgagcgcta ctcggtcatc ctcctggaca cgctgctagg ccgcatgctg
781  ccccagctgg tctgcggcct cgtcctccgg tgctccagtg aggacagcgc tggcccagcc
841  ctccctgccc tggggtccgt gcctggagaa tggctgccac aagactctga ctgccagctc
901  tgcatgtttg tgaccaccca ggcagggaac agcagtgagc aggccacgcc acaggcaatg
961  cgccaggcct gctgggcac  ctggctggac aggcaaaagt gtgagcggtt cgtggaggag
1021 aacgcgcccc ggctgcagac tctggtgtcc agtggctggg atgcccacat ggcctgccag
1081 gccctgggga catgtgcggc tccgttcagt cctctccagt gtgtccacag ccccacttc
1141 tgatgagaat gcacagccat ggcagcctgg aaccagaggc acttccgtcc actttgggag
1201 tgaggggtgg ccaaggcctc gtcttctgga caaggaatgc agatggggct tccggcccag
1261 ggccacctgc acatcccacc agtgccagcc caactctcac cacaccccca gcactgggct
1321 gatgggacct tgtcgtgggc ccccagtcct tctctaagtc ctggcatcaa gaggacagcg
1381 gagggagaat cctgtgctgg cgtcactccc atctccatgt gcatgagatg ctagcttta
1441 caatcactct gctaacgctt tcacaaaatt aagaattcgg aagaataaaa gtgggaacag
1501 aaagtcccag aaaagacaaa aaaaaaaaa  aaaaaaaaa  aaaaaaaaa  aaaaaaaaa
1561 aaaaaaaaa  aaaaaaaaa  a
```
(SEQ ID NO: 14)

B.
MAKSHLLPWLLLLPILCGPGTAAAITYSLACAQGPEFWCQSLEQALQCRALGHCLQEVWGHVEA
DDLCQECENISRLLTKMAKEAIFQDSVRKFLEQECDVLPLKLLAPLCRHLLDTYFPLIIEHFQS
HMNPKFICQHVGLCKPRHPEPGKGPEPWGPLLDKLALPLLPGVPQAKPGPQTQDLSEQLFPIPI
PYCWLCRTLIKRIQAVIPKGVLAMTVAQVCHVVPLLVGGICQCLVERYSVILLDTLLGRMLPQL
VCGLVLRCSSEDSAGPALPALGSVPGEWLPQDSDCQLCMFVTTQAGNSSEQATPQAMRQACLGT
WLDRQKCERFVEENAPRLQTLVSSGWDAHMACQALGTCAAPFSPLQCVHSPHF
(SEQ ID NO: 15)

Figure 7

A.
```
1    atggatgtgg gcagcaaaga ggtcttgatg gagagcccgc cggactacac agcagtccct
61   gggggccggc tcctcatccc ttgctgtccc gtgaacatca aacgccttct catcgtggtc
121  gtggttgtgg tccttgttgt cgtggtgatc gtaggggccc tgctcatggg ccttcacatg
181  agccagaaac atacagagat ggttctagag atgagcatca caggcccaga agcacagcaa
241  cgcctggccc tgagtgagcg tgtgggaacc actgccactt tctccattgg ctccactggc
301  actgtggttt atgactacca gcggctcctg attgcctaca agccagcccc cggaacctgc
361  tgctacatca tgaagatggc tccgcagaac atcccaagtc tcgaggctct caccagaaaa
421  ttgcagaact tccaggccaa gccccaagtg ccttcctcga agctgggcca ggagcagggc
481  catgacgccg gctcagcatt ctctggggac ctggccttcc tgggcaggac cgtgagcacc
541  ctgtgtggcg aggtgcccct gtactacacc taggactggt cagggcctca ggaagcccca
601  gagggacagc ggagatccag gagcaaaggg tcttgtgcag actggcagga agcagatcct
661  gtcgacacca ctgggactgg ccctgcagaa atgggactgt ggggggaggt gggcagagga
721  gaag
```
(SEQ ID NO: 16)

B.
MDVGSKEVLMESPPDYTAVPGGRLLIPCCPVNIKRLLIVVVVVVLVVVVIVGALLMGLHMSQKH
TEMVLEMSITGPEAQQRLALSERVGTTATFSIGSTGTVVYDYQRLLIAYKPAPGTCCYIMKMAP
QNIPSLEALTRKLQNFQAKPQVPSSKLGQEQGHDAGSAFSGDLAFLGRTVSTLCGEVPLYYT
(SEQ ID NO: 17)

Figure 8

A.
```
1    aattccgggt gctatagttg cttcctgtag gactgcagac tccagtacta gtctgtccag
61   agcaacaagt gataggaaac aagccagcat tgtaagagga catgcttctc ctccctctct
121  ccgtgctgct cctgctcaca cagccctgga gatccctggg agcagaaatg aagatctatt
181  cccagaaaac aatggccaac gcctgtaccc tggtcatgtg tagccccccg gaggatggtt
241  tgcctggtcg tgatggacga gatgggagag aagcccccg gggggagaag ggagatccag
301  gttcaccagg acctgcagga cgagcaggaa tgcctggacc agctggccct attgggctga
361  aaggagacaa tggctctgct ggagaacccg gaccaaaggg agacactgga ccacctgggc
421  ctccaggtat gcctggacca gctggaagag agggcccctc agggaagcag gggagcatgg
481  gacctccagg cacaccaggc cccaaggag acactgggcc caaggagga gtgggtgccc
541  caggcattca gggctcccca ggccctgcag gtctcaaagg agagagaggt gccctggtg
601  agcccggagc cctgacgt gctggggcac cagggcctgc tggagccata ggtccacagg
661  ggccttcagg tgccaggggc cccccaggac tgaagggaga cagaggtact cctggagaaa
721  gaggagcaaa gggggagagt gggcttgcag aggtcaatgc tctcaggcag cgggtgggaa
781  tcttagaggg acaactacaa cggctccaga atgccttctc tcagtataag aaagcgatgc
841  tcttccctaa tggccggagt gtcggggaga agatctttaa gacggtaggc tctgaaaaaa
901  cgtttcagga tgcccagcag atctgcacac aggctggagg acagttgccc tccccacgtt
961  ctggagctga aaacgaggcc ttgactcagc tggccacagc ccagaacaag gctgctttcc
1021 tgagcatgag cgacaccagg aaggagggta ctttcatcta ccccacgggg gagcccctgg
1081 tctattccaa ctgggccccc caggagccca acaatgatgg cggctcagag aactgtgtgg
1141 agatctttcc caatggcaag tggaatgaca aagtctgcgg agagcagcgc ctcgtgatct
1201 gcgagttctg agctcctcct gcacacacac acacacatag tgtgtgtgtt ggggcggtgg
1261 gggtcggggg gggggatggg cagtgcccag agctgcattt ttccagtgtt tgaataaaat
1321 agtgaccctc tactggccag ggcttctcca cagagccaca ggataaggcc agaggcaggg
1381 ctcctatgga atacatccct cagaataaag tttgaaactg gcttcacaca aaaaaaaaa
1441 aaaaaccgga attc
```
(SEQ ID NO: 18)

B.
MLLLPLSVLLLLTQPWRSLGAEMKIYSQKTMANACTLVMCSPPEDGLPGRDGRDGREGPRGEKG
DPGSPGPAGRAGMPGPAGPIGLKGDNGSAGEPGPKGDTGPPGPPGMPGPAGREGPSGKQGSMGP
PGTPGPKGDTGPKGGVGAPGIQGSPGPAGLKGERGAPGEPGAPGRAGAPGPAGAIGPQGPSGAR
GPPGLKGDRGTPGERGAKGESGLAEVNALRQRVGILEGQLQRLQNAFSQYKKAMLFPNGRSVGE
KIFKTVGSEKTFQDAQQICTQAGGQLPSPRSGAENEALTQLATAQNKAAFLSMSDTRKEGTFIY
PTGEPLVYSNWAPQEPNNDGGSENCVEIFPNGKWNDKVCGEQRLVICEF
(SEQ ID NO: 19)

Figure 9

A.
```
1    tggcagtggg agagaaggtc ttctccacca atgggcagtc agtcgctttt gatgtcatta
61   gagagttgtg tgccagagca ggtggacgca tcgctgcccc aaggagtcca gaggagaatg
121  aggccattgc aagcattgtg aagaaacaca acacttatgc ttacctcggc ctggttgagg
181  gccccactgc tggagacttc ttctacttgg atggaacccc tgtgaattac accaactggt
241  acccagggga acccaggggt cggggcaaag agaagtgtgt ggagatgtac acagatggcc
301  agtggaatga caggaactgc cagcagtacc gactggccat atgtgagttt tga
```
(SEQ ID NO: 20)

B.
AVGEKVFSTNGQSVAFDVIRELCARAGGRIAAPRSPEENEAIASIVKKHNTYAYLGLVEGPTAG
DFFYLDGTPVNYTNWYPGEPRGRGKEKCVEMYTDGQWNDRNCQQYRLAICEF
(SEQ ID NO: 21)

Figure 10

A.
```
1    ctttccgctg gtcgttgatc acttccagag ccaaatgaac ctgaaggcca tctgcaagca
61   cttgggcctg tgcaaacctg agcatccaga gccaggccag gggccagagc tgacaggctc
121  tctgctggac aagctggccc tccccctgct gcccgcaggc ctccaggcga ggcctgggcc
181  tcagacacag gatctctcca agcagaagtt ccccattcct cttcccttct gctggctctg
241  cagg
```
(SEQ ID NO: 22)

B.
FPLVVDHFQSQMNLKAICKHLGLCKPEHPEPGQGPELTGSLLDKLALPLLPAGLQARPGPQTQD
LSKQKFPIPLPFCWLCR
(SEQ ID NO: 23)

Figure 11

A.
```
1    ctctccctcc tggtgcatat aagaccctgg tcacacttgg ggatgagcag gggaaggtgc
61   ctacagcaag atggatgtag gcagcaaaga agtcctgatg gagagcccgc cggactactc
121  agcagtccca gggggccggc tccgcatccc ctgctgtcct gtgaacctca aacgccttct
181  tgtcgtggtc gtggtggtgg ttcttgtcgt cgtggtgatt gtagggggccc tgctcatggg
241  tcttcacatg agccagaaac atactgagat ggtcctagag atgagcctcg cagggccaga
301  agcccagcaa cgcctggccc tgagtgagca tgtgggaacc actgccacct tctccattgg
361  ctctagtggc aatgtggtct atgactacca gcggctcctg attgcctaca agccagcccc
421  gggaacctgc tgctatgtca tgaagatgtc tccgcagagt atgccgagtc ttgaggctct
481  caccaaaaaa ttccagaact tccaggccaa gccctcgacg cctacctcta agctgggcca
541  ggaggagggc cgtgtcgctg gctcagcacc ctccggggac ctggccttcc tgggcagcac
601  catgagcacc ctgtgtggcg aagtgcccct cttgtacatc taggaaacat cagggcctca
661  ggaagcccca agaggacagc aaagatccag gagcaaagag tcttgtgcag actcacagga
721  agccgcttct gggacaccac ggggactggc cctggagaaa tgggagctgt ggggagaggt
781  gggcagagga gaagcagctg ttaggggccc ggggcttct accaccaaag aataaagcag
841  cctgattgaa aaaaaaaaaa aaaaaaa
```
(SEQ ID NO: 24)

B.
MDVGSKEVLMESPPDYSAVPGGRLRIPCCPVNLKRLLVVVVVVVLVVVVIVGALLMGLHMSQKH
TEMVLEMSLAGPEAQQRLALSEHVGTTATFSIGSSGNVVYDYQRLLIAYKPAPGTCCYVMKMSP
QSMPSLEALTKKFQNFQAKPSTPTSKLGQEEGRVAGSAPSGDLAFLGSTMSTLCGEVPLLYI
(SEQ ID NO: 25)

Figure 12

A.
```
1     cgagtttgcc tggagattct gagctctaga ggacgcaact gacatgcttc tcctccctct
61    ctccgtgctg atcctgctca cacagccccc gaggtcactg ggagcagaaa tgaagaccta
121   ttcccagaga gcagtggcca acgcctgcgc cctggtcatg tgtagcccca tggagaatgg
181   cctgcctggt cgtgatggtc gggatgggag agagggccct cggggcgaga aggggggatcc
241   aggtttgcca ggagctgtag ggcgagcggg gatgcctgga ctggctggcc cagttgggcc
301   caaaggggac aacggctcta ctggagaacc cggagcaaag ggagacattg gaccatgcgg
361   gcctccagga cctccaggta tacctggtcc agccggaaaa gaaggtccct cagggcagca
421   ggggaacata ggacctccag gcacaccagg ccccaaagga gagactgggc caaaggaga
481   agtgggtgcc ctgggcatgc agggctctac aggggcaaga ggccctgcag gtcttaaagg
541   agagagaggt gcccccggtg agcgtggagc cctggaagt gctggggcag cagggcctgc
601   tggagccacg ggccctcagg gcccttcagg tgccagggc ccccaggac tgaaggggga
661   cagaggtcct cctggagaaa gaggagccaa gggagagagt ggactcccag gcatcactgc
721   tctgaggcaa caggtggaga ccttacaggg gcaggtacaa cgcctccaga aggccttctc
781   tcagtataag aaagtggagc tcttccccaa tggccgaggt gtcggggaga agatcttcaa
841   gacgggaggc tttgaaaaga cttttcagga tgctcagcag gtatgcacac aggccggggg
901   acagatggcc tccccacgct ctgagactga aacgaggcc ttgagccagc tggtcacagc
961   tcagaataag gctgctttcc tgagcatgac tgacatcaag acggagggca atttcaccta
1021  ccccacgggg gagcccctgg tctatgccaa ctgggcccct ggggagccca acaacaatgg
1081  tggcagcagc ggagcagaga actgtgtgga gatctttccc aatggcaagt ggaatgacaa
1141  ggcctgcgga gaactgcgcc tcgtgatctg cgagttctga gccctgggg agggaggggc
1201  ggtgtccaga gctgtgtgct accaacgtcc caataaatag gtgaccttct gctggccagg
1261  gcttctccac agagccgtgg gacgaggcca gaaggtaggg agcctatgga acgcctccct
1321  cagaataaag tacgaaactg gcctcacaaa aaaaaaaaaa aaaaaaaaaa aaaaaaaaaa
1381  aaaaa
```
(SEQ ID NO: 26)

B.
MLLLPLSVLILLTQPPRSLGAEMKTYSQRAVANACALVMCSPMENGLPGRDGRDGREGPRGEKG
DPGLPGAVGRAGMPGLAGPVGPKGDNGSTGEPGAKGDIGPCGPPGPPGIPGPAGKEGPSGQQGN
IGPPGTPGPKGETGPKGEVGALGMQGSTGARGPAGLKGERGAPGERGAPGSAGAAGPAGATGPQ
GPSGARGPPGLKGDRGPPGERGAKGESGLPGITALRQQVETLQGQVQRLQKAFSQYKKVELFPN
GRGVGEKIFKTGGFEKTFQDAQQVCTQAGGQMASPRSETENEALSQLVTAQNKAAFLSMTDIKT
EGNFTYPTGEPLVYANWAPGEPNNNGGSSGAENCVEIFPNGKWNDKACGELRLVICEF
(SEQ ID NO: 27)

Figure 13

A.
```
1    agcatgggct gtgttcgtgc aggaggagcc gctggagcag gcgccatgct gctgtgctct
61   ttgacccttc tgctcctctg gatggtggct tctggcctcg agtgcgacac aaaggaagtt
121  tgtcttggaa gccctggcat tcctggcact cccggatccc atggcctgcc aggaagagat
181  gggagagatg gtatcaaagg agaccctggg cctccaggcc ccatgggccc ccctggagga
241  atgccaggcc tccctgggcg tgatgggatg actggagccc ctggcctccc tggagaacgt
301  ggagaaaagg gagagcctgg cgagagaggt cctccagggt ttccagcgta tctagatgaa
361  gagctccagg gcacactcca tgagatcaga catcaagtcc tgcagtcaca ggcgtcctc
421  attttgcagg ggtccatgct ggaagtggga gagaaggtct tctctaccaa tgggcagtca
481  ctcaattttg atgccattaa agagttatgt gccagagcag gtggacacat cgctgcccca
541  aggagtccgg aggagaatga ggccattacc agcatcgtga agaagcacaa cacttatgct
601  tacctggggc tggctgaagg ccccaccgct ggagacttct attacctgga tggagcccct
661  gtgaattata ccaactggta cccaggggag cccaggggcc ggggtaaaga gaagtgtgta
721  gagatataca cagatggtca gtggaatgac aagaactgcc tgcagtaccg actggccatc
781  tgtgagttct gagcaggcac caaagccaca ggatggacag agtcctatct ttcctttcag
841  cctccatcct gggaatccac ctggtctatg gatcaggtgc tataattcct ttgtggctat
901  cagaagtgaa ggcactcttg atcactccac tcctgggtgg atcctaactc ctccccaatg
961  atcactaatc agtctgactc ccccagaacc ccttctcagc attgcactct tggcagccac
1021 tctaactttg cccttctgca agagacagag gtttctttcc tcctcttctt gtccagttcc
1081 tttatttata gatggcaaca gtaaggtcct gagatgaagg ttccctccat agcaccacac
1141 tgggtgcctg cttcctggcc ccctctactc tgtctttgca gctcactgct tgcccagcct
1201 catcaagatt tagcagttct gctcaagcac aatgataggt ggacttctgg gaaatttcac
1261 acatgtggag ctaaggatac atttggtttt atctatcaac ctgagatcta tggggaggca
1321 tcttgttagg ctctccatga agtcagaggg tcaggtggtg ctccagcatg atggaggcca
1381 atttattcct agtgattggc aggtattatc cacttccttg agtcttgggg tgtcagccag
1441 cgcctctaag gaagatctta ccccaccgt agacattacc caagtaactg cctgctgatg
1501 aacacattcc ccacctcttc agaactcagt gaggagttca caccacttgt cacaccacca
1561 tttattgagc acatactata caccaagcac cttgacatgc acttctaaaa catcttatgt
1621 gatttaatct tcacacagtg tcatgggatg agcattattt tccccaatct tttatataac
1681 aacgctgaaa tttagagaag ttaaatgttt tgagtttctt ttttaaaca tgaagcaatt
1741 ggcagaggct ggtttcaaac tcatctacct ggacctgaag cttgtgctca taaccacccc
1801 acctcactga acagagatga ttcaagtgta ataaatcatg actgtgttaa aaaaaaaaa
1861 aaaaaaaaaa aaaaaaaaaa aaaaaaaaaa aaaaaaaaa a
```
(SEQ ID NO: 28)

B.
MLLCSLTLMLLWMVASGLECDTKEVCLGSPGIPGTPGSHGLPGR
DGRDGIKGDPGPPGPMGPPGGMPGLPGRDGMTGAPGLPGERGEKGEPGERGPPGFPAY
LDEELQGTLHEIRHQVLQSQGVLILQGSMLEVGEKVFSTNGQSLNFDAIKELCARAGG
HIAAPRSPEENEAITSIVKKHNTYAYLGLAEGPTAGDFYYLDGAPVNYTNWYPGEPRG
RGKEKCVEIYTDGQWNDKNCLQYRLAICEF
(SEQ ID NO: 29)

Figure 14

A.
```
1    gccaagtcac gcctgctgcc gtggctgctg ctgctgctgc ccatgctctg tggtctgggc
61   tctgcagctg tggggaccac ctactccctg acctgtgccc agggccccac attctggtgc
121  caaagtctgg agcaagcttt gcagtgcaga gccctagggc actgcctgca ggaagtctgg
181  ggacatgcgg aagccgatga cctgtgccag gaatgtgaga acatctcccg catcctcacc
241  aagatggcca aggaggccat tttccaggac acagtgcgca aattcctgga gcaggagtgc
301  gatgttcttc cgctgaaact cttggtgccc cagtgtcgcc acctgctgga cacctacttc
361  cctctgatca ttgaccactt ccagagccag atgaacccga agttcatctg tcagcatgtg
421  ggcctatgca agcccaggca cccagagcca gggaaggggc cagagccatg gggtcctctg
481  ctggacaaga tggccctccc cctgctgcca ggggccctcc aggccaagcc tgggcctcag
541  acacaggacc tctcccagca gcggttcccc atccctctcc ccttctgctg gctctgccgg
601  actctgatca aacgaatcca ggctgtgatt cccaagggtg tactggccat gactgtggcc
661  caggtgtgcc acgtggtccc cctgctggtg ggcggcatct gccagtgcct ggttgagcgc
721  tactctgtca tcctcctgga cacgctgcta ggccgcatgc tgccccagct ggtctgcggc
781  ctcgtcctcc ggtgctccag cgaggacagc gctggcccag ccctccctgc cctggggtcc
841  ctgcctggag aatggctgcc acaagactct gagtgccagc tctgcatgtt tgtgaccact
901  caggcaggga acagcagtga gcaggccatg ccacaggcaa tgcgccaggc tgcctgggc
961  acctggctgg acaggcaaaa gtgtgagcag tttgtggagg agcatgcgcc ccggctacag
1021 actctggtgt ccagcggctg ggatgccac atggcctgcc aggccctggg gacatgtgcg
1081 actccgttca gtcctctcca gtgtatccac agccccact tctgatgaga acgcacagcc
1141 atggcaggct gaactcaagg ctcctgaggg ccccggcagc accatctcga ctgtcctctc
1201 tcaaacccgc tcacccctct gcccagaatc ccatggcgt tcagtgccag gcccggctcc
1261 cagcttgctg gccctccccc agcccagagg gaagcttccg tgcctgacca tggctttccc
1321 ctcacagacc accctctgca tgcactgatc ctcagtacca aatgtgcttg caccaagccc
1381 tgcctttcct gaaactcagg ggacaccaga cattgctccc caaagatgcc aggaactcct
1441 ccatcgcctg actcctccta cctgagactc ctccctgtct ccctcaatgt cactgggtca
1501 gaggtgaccc cttaggacag agtggggtc agaggcagac tccatgccag gtgcctccgg
1561 agagggaagc gcccctgaga agagacctgg caacttcaca gttctgtcca gagcaagccc
1621 ccaacatgaa ggtcatgtat tcaaaaaaaa aaaaaaaaa
```
(SEQ ID NO: 30)

B.
AKSRLLPWLLLLLPMLCGLGSAAVGTTYSLTCAQGPTFWCQSLEQALQCRALGHCLQEVWGHAE
ADDLCQECENISRILTKMAKEAIFQDTVRKFLEQECDVLPLKLLVPQCRHLLDTYFPLIIDHFQ
SQMNPKFICQHVGLCKPRHPEPGKGPEPWGPLLDKMALPLLPGALQAKPGPQTQDLSQQRFPIP
LPFCWLCRTLIKRIQAVIPKGVLAMTVAQVCHVVPLLVGGICQCLVERYSVILLDTLLGRMLPQ
LVCGLVLRCSSEDSAGPALPALGSLPGEWLPQDSECQLCMFVTTQAGNSSEQAMPQAMRQACLG
TWLDRQKCEQFVEEHAPRLQTLVSSGWDAHMACQALGTCATPFSPLQCIHSPHF
(SEQ ID NO: 31)

Figure 15

A.
```
1   gtctacagca agatggatgt gggcagcaaa gaggtcttga tggagagccc gccggactac
61  tcagcagtcc ccgggggccg gctccgcatc ccctgctgtc ccgtgaacat caaacgcctt
121 ctcatcgtgg ttgtggttgt ggtccttgtc gtcgtggtga tcgtaggagc cctgctcatg
181 ggtcttcaca tgagccagaa acatacagag atggttctag agatgagcat cgcaggcccg
241 gaagcacagc aacgcctggc cctgagtgag cgtgtgggaa ccactgccac tttctccatc
301 ggctccactg gcactgtggt gtatgactac cagcggctcc tgattgccta caagccagcc
361 cccggaacct gctgctacat tatgaaggtg gctccgcaga gcatcccaag tctcgaggct
421 ctcactagaa aattgccgaa cttccaggcc aagcccccag tgccttcctc gaagctgggc
481 caggagcagg gccgtgacgc cggctcagca ttctctgggg acctggcctt cctgggcagg
541 accgtgagca ccctgtgtgg cgaggtgccc ctgtactaca cttaggactg gtcagggcct
601 caggaagccc caaagggaca gtggagatcc aggagcaaag ggtcttgtgc agattggcag
661 gaagtggata ctgtcgacac cactgggact ggcctggag aaatgggagc tgtggggaga
721 ggtgggcaga ggagaagcag ttcctagggc ccaaggggc tcctaccacc aaagattaaa
781 gcatcctgat tgcaaaaaaa aaaaaaaaa
```
(SEQ ID NO: 32)

B.
MDVGSKEVLMESPPDYSAVPGGRLRIPCCPVNIKRLLIVVVVVVLVVVVIVGALLMGLHMSQKH
TEMVLEMSIAGPEAQQRLALSERVGTTATFSIGSTGTVVYDYQRLLIAYKPAPGTCCYIMKVAP
QSIPSLEALTRKLPNFQAKPPVPSSKLGQEQGRDAGSAFSGDLAFLGRTVSTLCGEVPLYYT
(SEQ ID NO: 33)

Figure 16

A.
```
1    ttccctgatg gccggagtgt cgggaagaag atctttaaga cggcaggctc tgaaaaaacg
61   tttcaggatg cccagcaggt ctgcacacag gctggaggac agctgccctc cccacgttct
121  gcagctgaga atgaggcttt gactcagctg gccacagccc agaacaagac tgctttcctg
181  agcatgaccg ataccaggaa ggagggtact ttcatctacc cacggggga gcccctggtc
241  tattccaact gggccccca ggagcccaac aatgatggcg gctcagagaa ctgtgtggag
301  atct
```
(SEQ ID NO: 34)

B.

FPDGRSVGKKIFKTAGSEKTFQDAQQVCTQAGGQLPSPRSAAENEALTQLATAQNKTAFLSMTD
TRKEGTFIYPTGEPLVYSNWAPQEPNNDGGSENCVEI
(SEQ ID NO: 35)

Figure 17

SP-B Residues 1-25

H—Phe—Pro—Ile—Pro—Leu—Pro—Tyr—Cys—Trp—Leu—Cys—Arg—Ala—Leu—Ile—Lys—Arg—Ile—Gln—Ala—Met—Ile—Pro—Lys—Gly—OH

| ID | Molecule | Reference |
|---|---|---|
| 1 |  | 5-2 |
| 2 |  | 5-3 |

Figure 17 Cont.
| ID | Molecule | Reference |
|---|---|---|
| 3 | 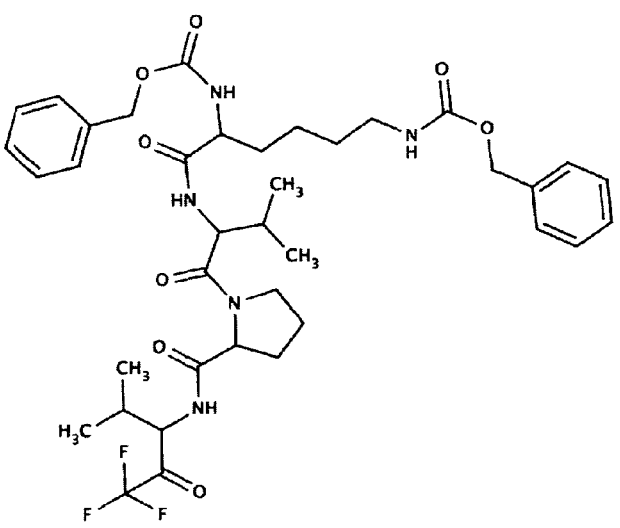 | 6-4 |
| 4 | 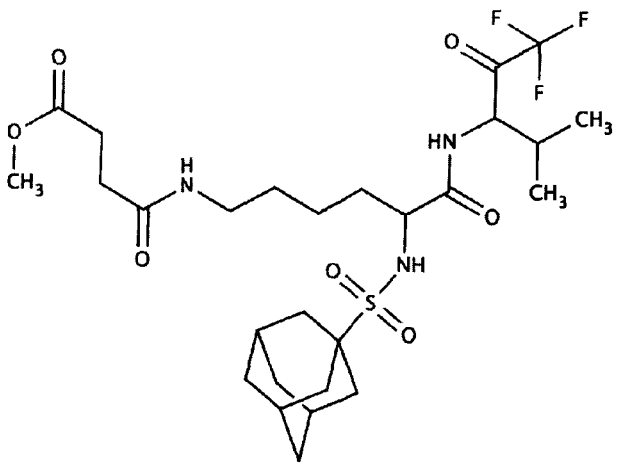 | 6-5 |

Figure 17 Cont.

| ID | Molecule | Reference |
|---|---|---|
| 5 | | 6-6 |
| 6 | | 6-7 |
| 7 | | 7-5 |

Figure 17 Cont.
| ID | Molecule | Reference |
|---|---|---|
| 8 | 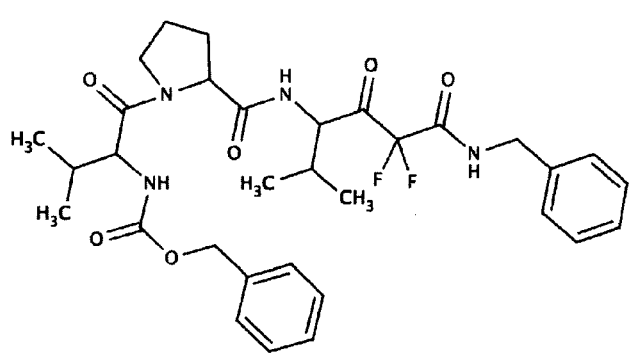 | 7-6 |
| 9 | 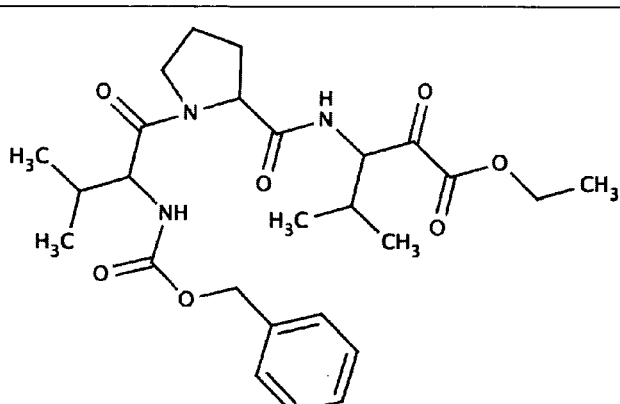 | 8-3 |
| 10 | 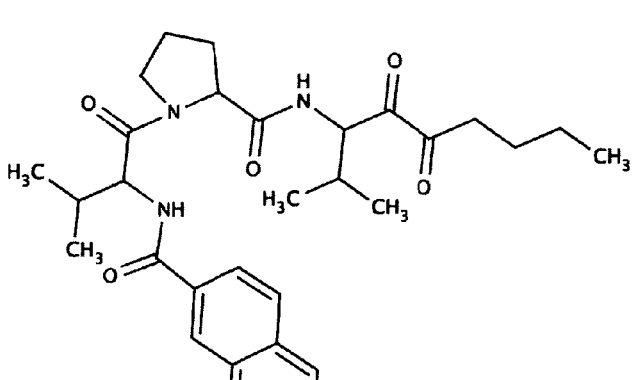 | 8-6 |

Figure 17 Cont.
| ID | Molecule | Reference |
|----|----------|-----------|
| 11 | 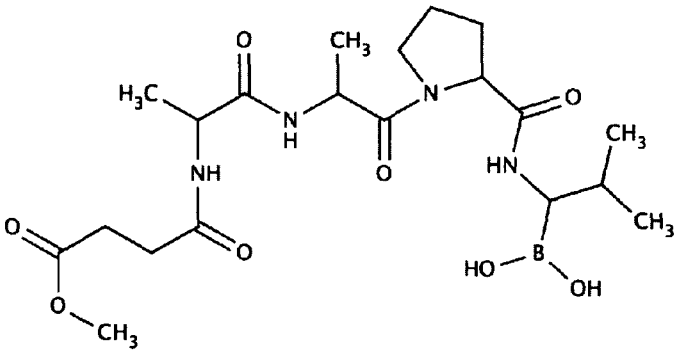 | 10-4 |
| 12 | 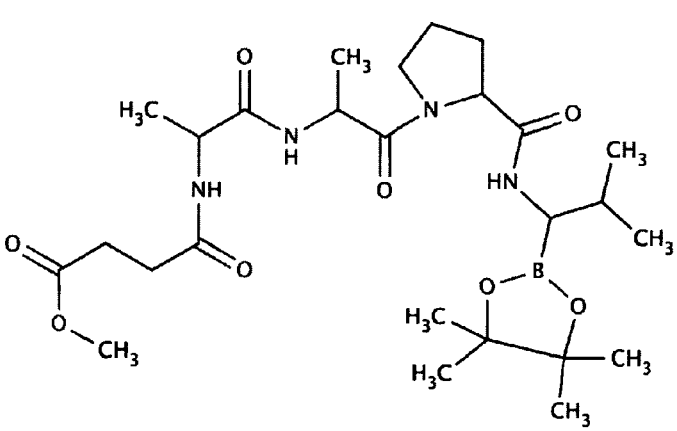 | 10-5 |

General Scheme

Final compounds will be roughly 1:1 mixtures of epimers at the stereogenic center α to the ketone carbonyl (as per J. Med. Chem. 1997, 40(12), 1876).

Deliverables

Ligand: 50 mg

Ligand + linker: 50 mg plus approx. 0.5 – 1.0 g for linkage to peptide.

Figure 19
| SL. NO. | STRUCTURE | NAME ASSIGNED | MOL. WT. |
|---|---|---|---|
| 1 | 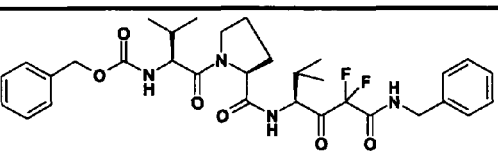 | TARGET 1 | 614 |
| 2 | 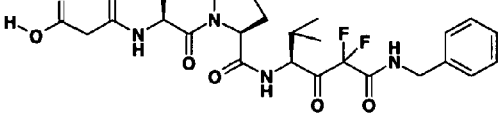 | TARGET 2 | 566 |
| 3 | 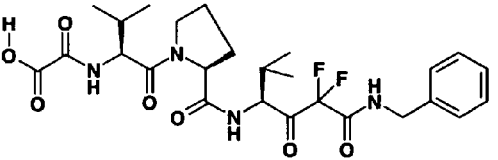 | TARGET 3 | 552 |
| 4 | PEPTIDE | TARGET A | 2926.97 |
| 5 | 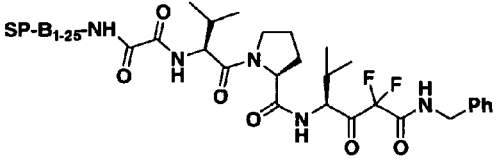 | TARGET B | 3461 |
| 6 | 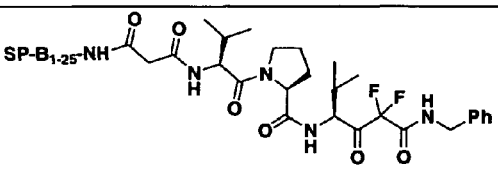 | TARGET C | 3475 |

SEQUENCE LISTING

<160> NUMBER OF SEQ ID NOS: 96

<210> SEQ ID NO 1
<211> LENGTH: 968
<212> TYPE: DNA
<213> ORGANISM: Homo sapiens

<400> SEQUENCE: 1
ccaagcagct ggaggctctg tgtgtgggtc gctgatttct tggagcctga aaagaaagta     60

```
acacagcagg gatgaggaca gatggtgtga gtcagtgaga gcagcgactg gacccagagc    120
catgtggctg tgccctctgg ccctcaacct catcttgatg gcagcctctg gtgctgtgtg    180
cgaagtgaag gacgtttgtg ttggaagccc tggtatcccc ggcactcctg gatcccacgg    240
cctgccaggc agggacggga gagatggtct caaaggagac cctggccctc caggccccat    300
gggtccacct ggagaaatgc catgtcctcc tggaaatgat gggctgcctg gagcccctgg    360
tatccctgga gagtgtggag agaagggga gcctggcgag aggggccctc agggcttcc      420 agctcatcta gatgaggagc tccaagccac actccacgac tttagacatc aaatcctgca    480
gacaagggga gccctcagtc tgcagggctc cataatgaca gtaggagaga aggtcttctc    540
cagcaatggg cagtccatca cttttgatgc cattcaggag gcatgtgcca gagcaggcgg    600
ccgcattgct gtcccaagga atccagagga aaatgaggcc attgcaagct tcgtgaagaa    660
gtacaacaca tatgcctatg taggcctgac tgagggtccc agccctggag acttccgcta    720
ctcagacggg acccctgtaa actacaccaa ctggtaccga ggggagcccg caggtcgggg    780
aaaagagcag tgtgtggaga tgtacacaga tgggcagtgg aatgacagga actgcctgta    840
ctcccgactg accatctgtg agttctgaga ggcatttagg ccatgggaca gggaggacgc    900
tctctggcct tcggcctcca tcctgaggct ccacttggtc tgtgagatgc tagaactccc    960
tttcaaca                                                            968
```

```
<210> SEQ ID NO 2
<211> LENGTH: 248
<212> TYPE: PRT
<213> ORGANISM: Homo sapiens

<400> SEQUENCE: 2

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Ser Pro Gly Ile
                20                  25                  30

Pro Gly Thr Pro Gly Ser His Gly Leu Pro Gly Arg Asp Gly Arg Asp
            35                  40                  45

Gly Leu Lys Gly Asp Pro Gly Pro Pro Gly Met Gly Pro Pro Gly
        50                  55                  60

Glu Met Pro Cys Pro Pro Gly Asn Asp Gly Leu Pro Gly Ala Pro Gly
65                  70                  75                  80

Ile Pro Gly Glu Cys Gly Glu Lys Gly Glu Pro Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
    130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205
```

```
Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 3
<211> LENGTH: 2026
<212> TYPE: DNA
<213> ORGANISM: Homo sapiens

<400> SEQUENCE: 3
gccatggctg agtcacacct gctgcagtgg ctgctgctgc tgctgcccac gctctgtggc      60
ccaggcactg ctgcctggac cacctcatcc ttggcctgtg cccagggccc tgagttctgg     120
tgccaaagcc tggagcaagc attgcagtgc agagccctag gcattgcct acaggaagtc      180 tggggacatg tgggagccga tgacctatgc aagagtgtg aggacatcgt ccacatcctt       240
aacaagatgg ccaaggaggc cattttccag gacacgatga ggaagttcct ggagcaggag     300
tgcaacgtcc tccccttgaa gctgctcatg ccccagtgca accaagtgct tgacgactac     360
ttccccctgg tcatcgacta cttccagaac cagactgact caaacggcat ctgtatgcac     420
ctgggcctgt gcaaatcccg gcagccgag ccagagcagg agccagggat gtcagacccc      480
ctgcccaaac tctgcgggga ccctctgcca gaccctctgc tggacaagct cgtcctccct     540
gtgctgcccg ggcccctcca ggcgaggcct gggcctcaca cacaggatct ctccgagcag     600
caattcccca ttcctctccc ctattgctgg ctctgcaggg ctctgatcaa gcggatccaa     660
gccatgattc caagggtgc gctagctgtg cagtggccc aggtgtgccg cgtggtacct       720
ctggtggcgg gcggcatctg ccagtgcctg gctgagcgct actccgtcat cctgctcgac     780
acgctgctgg gccgcatgct gccccagctg gtctgccgcc tcgtcctccg gtgctccatg     840
gatgacagcg ctggcccaag gtcgccgaca ggagaatggc tgccgcgaga ctctgagtgc     900
cacctctgca tgtccgtgac cacccaggcc gggaacagca gcgagcaggc cataccacag     960
gcaatgctcc aggcctgtgt tggctcctgg ctggacaggg aaaagtgcaa gcaatttgtg    1020
gagcagcaca cgccccagct gctgaccctg tgcccaggg ctgggatgc ccacaccacc       1080 tgccaggccc tcggggtgtg tggaccatg tccagccctc tccagtgtat ccacagcccc      1140
gacctttgat gagaactcag ctgtccagct gcaaggaaa agccaagtga cgggctct        1200 gggaccatgg tgaccaggct cttccccctgc tccctggccc tcgccagctg ccaggctgaa    1260
aagaagcctc agctcccaca ccgccctcct caccgccctt cctcggcagt cacttccact    1320
ggtggaccac gggcccccag ccctgtgtcg gccttgtctg tctcagctca accacagtct    1380
gacaccagag cccacttcca tcctctctgg tgtgaggcac agcgagggca gcatctggag    1440
gagctctgca gcctccacac ctaccacgac ctcccagggc tgggctcagg aaaaaccagc    1500
cactgcttta caggacaggg ggttgaagct gagccccgcc tcacacccac ccccatgcac    1560
tcaaagattg gattttacag ctacttgcaa ttcaaaattc agaagaataa aaatgggaa     1620 catacagaac tctaaaagat agacatcaga aattgttaag ttaagctttt tcaaaaaatc    1680
agcaattccc cagcgtagtc aagggtggac actgcacgct ctggcatgat gggatggcga    1740
ccgggcaagc tttcttcctc gagatgctct gctgcttgag agctattgct ttgttaagat    1800
ataaaaaggg gtttctttttt gtctttctgt aaggtggact tccagctttt gattgaaagt    1860
```

```
cctagggtga ttctatttct gctgtgattt atctgctgaa agctcagctg gggttgtgca    1920
agctagggac ccattcctgt gtaatacaat gtctgcacca atgctaataa agtcctattc    1980
tcttttatga aaaaaaaaaa aaaaaaaaaa aaaaaaaaaa aaaaaa                   2026

<210> SEQ ID NO 4
<211> LENGTH: 381
<212> TYPE: PRT
<213> ORGANISM: Homo sapiens

<400> SEQUENCE: 4

Met Ala Glu Ser His Leu Leu Gln Trp Leu Leu Leu Leu Pro Thr
1               5                   10                  15

Leu Cys Gly Pro Gly Thr Ala Ala Trp Thr Thr Ser Ser Leu Ala Cys
                20                  25                  30

Ala Gln Gly Pro Glu Phe Trp Cys Gln Ser Leu Glu Gln Ala Leu Gln
                35                  40                  45

Cys Arg Ala Leu Gly His Cys Leu Gln Glu Val Trp Gly His Val Gly
            50                  55                  60

Ala Asp Asp Leu Cys Gln Glu Cys Glu Asp Ile Val His Ile Leu Asn
65              70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
        115                 120                 125

Asn Gln Thr Asp Ser Asn Gly Ile Cys Met His Leu Gly Leu Cys Lys
    130                 135                 140

Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
        195                 200                 205

Trp Leu Cys Arg Ala Leu Ile Lys Arg Ile Gln Ala Met Ile Pro Lys
    210                 215                 220

Gly Ala Leu Ala Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Asp Asp Ser Ala Gly Pro Arg Ser Pro
        275                 280                 285

Thr Gly Glu Trp Leu Pro Arg Asp Ser Glu Cys His Leu Cys Met Ser
    290                 295                 300

Val Thr Thr Gln Ala Gly Asn Ser Ser Glu Gln Ala Ile Pro Gln Ala
305                 310                 315                 320

Met Leu Gln Ala Cys Val Gly Ser Trp Leu Asp Arg Glu Lys Cys Lys
                325                 330                 335

Gln Phe Val Glu Gln His Thr Pro Gln Leu Leu Thr Leu Val Pro Arg
            340                 345                 350
```

Gly Trp Asp Ala His Thr Thr Cys Gln Ala Leu Gly Val Cys Gly Thr
        355                 360                 365

Met Ser Ser Pro Leu Gln Cys Ile His Ser Pro Asp Leu
    370                 375                 380

<210> SEQ ID NO 5
<211> LENGTH: 79
<212> TYPE: PRT
<213> ORGANISM: Homo sapiens

<400> SEQUENCE: 5

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser Met
65                  70                  75

<210> SEQ ID NO 6
<211> LENGTH: 991
<212> TYPE: DNA
<213> ORGANISM: Homo sapiens

<400> SEQUENCE: 6
cttatctcgg cttcgtttct ggagggccag gaacaaacag gcttcaaagc caagggcttg      60
gctggcacac aggggcttg gtccttcacc tctgtcccct ctccctacgg acacatataa     120
gaccctggtc acacctggga gaggaggaga ggagagcata gcacctgcag caagatggat     180
gtgggcagca aagaggtcct gatggagagc ccgccggact actccgcagc tccccgggc     240 cgatttggca ttccctgctg cccagtgcac ctgaaacgcc ttcttatcgt ggtggtggtg     300
gtggtcctca tcgtcgtggt gattgtggga gccctgctca tgggtctcca catgagccag     360
aaacacacgg agatggttct ggagatgagc attgggcgc cggaagccca gcaacgcctg     420
gccctgagtg agcacctggt taccactgcc accttctcca tcggctccac tggcctcgtg     480
gtgtatgact accagcagct gctgatcgcc tacaagccag ccctggcac tgctgctac     540 atcatgaaga tagctccaga gagcatcccc agtcttgagg ctctcaatag aaaagtccac     600
aacttccaga tggaatgctc tctgcaggcc aagcccgcag tgcctacgtc taagctgggc     660
caggcagagg ggcgagatgc aggctcagca ccctccggag gggacccggc cttcctgggc     720
atggccgtga caccctgtg tggcgaggtg ccgctctact acatctagga cgcctccggt     780
gagcagggtc agtggaagcc caacgggaa aggaaacgcc ccgggcaaag ggtcttttgc     840
agcttttgca gacgggcaag aagctgcttc tgcccacacc gcaggacaa accctggaga     900 aatgggagct tggggagagg atgggagtgg gcagaggtgg cacccagggg cccgggaact     960
cctgccacaa cagaataaag cagcctgatt g                                    991

<210> SEQ ID NO 7
<211> LENGTH: 197
<212> TYPE: PRT
<213> ORGANISM: Homo sapiens

<400> SEQUENCE: 7

```
Met Asp Val Gly Ser Lys Glu Val Leu Met Glu Ser Pro Pro Asp Tyr
1               5                   10                  15

Ser Ala Ala Pro Arg Gly Arg Phe Gly Ile Pro Cys Cys Pro Val His
            20                  25                  30

Leu Lys Arg Leu Leu Ile Val Val Val Val Leu Ile Val Val
        35                  40                  45

Val Ile Val Gly Ala Leu Leu Met Gly Leu His Met Ser Gln Lys His
    50                  55                  60

Thr Glu Met Val Leu Glu Met Ser Ile Gly Ala Pro Glu Ala Gln Gln
65                  70                  75                  80

Arg Leu Ala Leu Ser Glu His Leu Val Thr Thr Ala Thr Phe Ser Ile
                85                  90                  95

Gly Ser Thr Gly Leu Val Val Tyr Asp Tyr Gln Gln Leu Leu Ile Ala
                100                 105                 110

Tyr Lys Pro Ala Pro Gly Thr Cys Cys Tyr Ile Met Lys Ile Ala Pro
        115                 120                 125

Glu Ser Ile Pro Ser Leu Glu Ala Leu Asn Arg Lys Val His Asn Phe
130                 135                 140

Gln Met Glu Cys Ser Leu Gln Ala Lys Pro Ala Val Pro Thr Ser Lys
145                 150                 155                 160

Leu Gly Gln Ala Glu Gly Arg Asp Ala Gly Ser Ala Pro Ser Gly Gly
                165                 170                 175

Asp Pro Ala Phe Leu Gly Met Ala Val Asn Thr Leu Cys Gly Glu Val
        180                 185                 190

Pro Leu Tyr Tyr Ile
        195

<210> SEQ ID NO 8
<211> LENGTH: 174
<212> TYPE: PRT
<213> ORGANISM: Homo sapiens

<400> SEQUENCE: 8

Phe Gly Ile Pro Cys Cys Pro Val His Leu Lys Arg Leu Leu Ile Val
1               5                   10                  15

Val Val Val Val Leu Ile Val Val Ile Val Gly Ala Leu Leu
            20                  25                  30

Met Gly Leu His Met Ser Gln Lys His Thr Glu Met Val Leu Glu Met
            35                  40                  45

Ser Ile Gly Ala Pro Glu Ala Gln Gln Arg Leu Ala Leu Ser Glu His
    50                  55                  60

Leu Val Thr Thr Ala Thr Phe Ser Ile Gly Ser Thr Gly Leu Val Val
65                  70                  75                  80

Tyr Asp Tyr Gln Gln Leu Leu Ile Ala Tyr Lys Pro Ala Pro Gly Thr
                85                  90                  95

Cys Cys Tyr Ile Met Lys Ile Ala Pro Glu Ser Ile Pro Ser Leu Glu
                100                 105                 110

Ala Leu Asn Arg Lys Val His Asn Phe Gln Met Glu Cys Ser Leu Gln
            115                 120                 125

Ala Lys Pro Ala Val Pro Thr Ser Lys Leu Gly Gln Ala Glu Gly Arg
        130                 135                 140

Asp Ala Gly Ser Ala Pro Ser Gly Gly Asp Pro Ala Phe Leu Gly Met
145                 150                 155                 160

Ala Val Asn Thr Leu Cys Gly Glu Val Pro Leu Tyr Tyr Ile
```

<210> SEQ ID NO 9
<211> LENGTH: 1299
<212> TYPE: DNA
<213> ORGANISM: Homo sapiens

<400> SEQUENCE: 9

```
agtttgcttg gagctcctgg ggcctaacaa aaagaaacct gccatgctgc tcttcctcct      60
ctctgcactg gtcctgctca cacagccct gggctacctg gaagcagaaa tgaagaccta     120
ctcccacaga acaatgccca gtgcttgcac cctggtcatg tgtagctcag tggagagtgg     180
cctgcctggt cgcgatggac gggatgggag agagggccct cggggcgaga agggggaccc     240
aggtttgcca ggagctgcag gcaagcagg gatgcctgga caagctggcc cagttgggcc     300
caaaggggac aatggctctg ttggagaacc tggaccaaag ggagacactg gccaagtgg     360
acctccagga cctcccggtg tgcctggtcc agctggaaga aaggtcccc tggggaagca     420
ggggaacata ggacctcagg gcaagccagg cccaaaagga gaagctgggc caaaggaga     480
agtaggtgcc ccaggcatgc agggctcggc aggggcaaga ggcctcgcag gccctaaggg     540
agagcgaggt gtccctggtg agcgtggagt ccctggaaac acaggggcag cagggtctgc     600
tggagccatg ggtccccagg gaagtccagg tgccagggga ccccgggat gaaggggga     660
caaaggcatt cctggagaca aaggagcaaa gggagaaagt gggcttccag atgttgcttc     720
tctgaggcag caggttgagg ccttacaggg acaagtacag cacctccagg ctgctttctc     780
tcagtataag aaagttgagc tcttcccaaa tggccaaagt gtcggggaga agattttcaa     840
gacagcaggc tttgtaaaac catttacgga ggcacagctg ctgtgcacac aggctggtgg     900
acagttggcc tctccacgct ctgccgctga gaatgccgcc ttgcaacagc tggtcgtagc     960
taagaacgag gctgctttcc tgagcatgac tgattccaag acagagggca agttcaccta    1020
ccccacagga gagtccctgg tctattccaa ctgggcccca ggggagcca acgatgatgg    1080
cgggtcagag gactgtgtgg agatcttcac caatggcaag tggaatgaca gggcttgtgg    1140
agaaaagcgt cttgtggtct gcgagttctg agccaactgg ggtgggtggg gcagtgcttg    1200
gcccaggagt ttggccagaa gtcaaggctt agaccctcat gctgccaata tcctaataaa    1260
aaggtgacca tctgtgccgg gaaaaaaaaa aaaaaaaaa                           1299
```

<210> SEQ ID NO 10
<211> LENGTH: 375
<212> TYPE: PRT
<213> ORGANISM: Homo sapiens

<400> SEQUENCE: 10

```
Met Leu Leu Phe Leu Leu Ser Ala Leu Val Leu Thr Gln Pro Leu
1               5                  10                  15

Gly Tyr Leu Glu Ala Glu Met Lys Thr Tyr Ser His Arg Thr Met Pro
                20                  25                  30

Ser Ala Cys Thr Leu Val Met Cys Ser Ser Val Glu Ser Gly Leu Pro
            35                  40                  45

Gly Arg Asp Gly Arg Asp Gly Arg Glu Gly Pro Arg Gly Glu Lys Gly
        50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95
```

Gly Pro Lys Gly Asp Thr Gly Pro Ser Gly Pro Pro Gly Pro Pro Gly
            100                 105                 110

Val Pro Gly Pro Ala Gly Arg Glu Gly Pro Leu Gly Lys Gln Gly Asn
            115                 120                 125

Ile Gly Pro Gln Gly Lys Pro Gly Lys Glu Ala Gly Pro Lys
        130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Thr Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

Ile Pro Gly Asp Lys Gly Ala Lys Gly Glu Ser Gly Leu Pro Asp Val
        210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                245                 250                 255

Gly Gln Ser Val Gly Glu Lys Ile Phe Lys Thr Ala Gly Phe Val Lys
            260                 265                 270

Pro Phe Thr Glu Ala Gln Leu Leu Cys Thr Gln Ala Gly Gly Gln Leu
        275                 280                 285

Ala Ser Pro Arg Ser Ala Ala Glu Asn Ala Ala Leu Gln Gln Leu Val
        290                 295                 300

Val Ala Lys Asn Glu Ala Ala Phe Leu Ser Met Thr Asp Ser Lys Thr
305                 310                 315                 320

Glu Gly Lys Phe Thr Tyr Pro Thr Gly Glu Ser Leu Val Tyr Ser Asn
                325                 330                 335

Trp Ala Pro Gly Glu Pro Asn Asp Asp Gly Gly Ser Glu Asp Cys Val
            340                 345                 350

Glu Ile Phe Thr Asn Gly Lys Trp Asn Asp Arg Ala Cys Gly Glu Lys
        355                 360                 365

Arg Leu Val Val Cys Glu Phe
    370                 375

<210> SEQ ID NO 11
<211> LENGTH: 355
<212> TYPE: PRT
<213> ORGANISM: Homo sapiens

<400> SEQUENCE: 11

Ala Glu Met Lys Thr Tyr Ser His Arg Thr Met Pro Ser Ala Cys Thr
1               5                   10                  15

Leu Val Met Cys Ser Ser Val Glu Ser Gly Leu Pro Gly Arg Asp Gly
            20                  25                  30

Arg Asp Gly Arg Glu Gly Pro Arg Gly Glu Lys Gly Asp Pro Gly Leu
        35                  40                  45

Pro Gly Ala Ala Gly Gln Ala Gly Met Pro Gly Gln Ala Gly Pro Val
    50                  55                  60

Gly Pro Lys Gly Asp Asn Gly Ser Val Gly Glu Pro Gly Pro Lys Gly
65                  70                  75                  80

Asp Thr Gly Pro Ser Gly Pro Pro Gly Pro Pro Gly Val Pro Gly Pro

```
                        85                  90                  95
Ala Gly Arg Glu Gly Pro Leu Gly Lys Gln Gly Asn Ile Gly Pro Gln
                100                 105                 110

Gly Lys Pro Gly Pro Lys Gly Glu Ala Gly Pro Lys Gly Glu Val Gly
            115                 120                 125

Ala Pro Gly Met Gln Gly Ser Ala Gly Ala Arg Gly Leu Ala Gly Pro
        130                 135                 140

Lys Gly Glu Arg Gly Val Pro Gly Glu Arg Gly Val Pro Gly Asn Thr
145                 150                 155                 160

Gly Ala Ala Gly Ser Ala Gly Ala Met Gly Pro Gln Gly Ser Pro Gly
                165                 170                 175

Ala Arg Gly Pro Pro Gly Leu Lys Gly Asp Lys Gly Ile Pro Gly Asp
            180                 185                 190

Lys Gly Ala Lys Gly Glu Ser Gly Leu Pro Asp Val Ala Ser Leu Arg
        195                 200                 205

Gln Gln Val Glu Ala Leu Gln Gly Gln Val Gln His Leu Gln Ala Ala
210                 215                 220

Phe Ser Gln Tyr Lys Lys Val Glu Leu Phe Pro Asn Gly Gln Ser Val
225                 230                 235                 240

Gly Glu Lys Ile Phe Lys Thr Ala Gly Phe Val Lys Pro Phe Thr Glu
                245                 250                 255

Ala Gln Leu Leu Cys Thr Gln Ala Gly Gly Gln Leu Ala Ser Pro Arg
            260                 265                 270

Ser Ala Ala Glu Asn Ala Ala Leu Gln Gln Leu Val Val Ala Lys Asn
        275                 280                 285

Glu Ala Ala Phe Leu Ser Met Thr Asp Ser Lys Thr Glu Gly Lys Phe
290                 295                 300

Thr Tyr Pro Thr Gly Glu Ser Leu Val Tyr Ser Asn Trp Ala Pro Gly
305                 310                 315                 320

Glu Pro Asn Asp Asp Gly Gly Ser Glu Asp Cys Val Glu Ile Phe Thr
                325                 330                 335

Asn Gly Lys Trp Asn Asp Arg Ala Cys Gly Glu Lys Arg Leu Val Val
            340                 345                 350

Cys Glu Phe
        355

<210> SEQ ID NO 12
<211> LENGTH: 2037
<212> TYPE: DNA
<213> ORGANISM: Bos sp.

<400> SEQUENCE: 12
ggctatggag gcagggagca tgggctgtgt tcgtgcagga ggagctgctg gagcaggcgc     60
catgctgctg tgctctttga cccttaccct cctctggatg gtggcttctg gcctcgagtg    120
cgatgtcaag gaagtttgtc ttggaagccc tggcattcct ggcactcctg atcccatgg    180 cctgccagga agagatggga gagatggtat caaaggagac cctgggcctc aggccccat    240 gggccccct ggaggaatgc caggcctccc tgggcgtgat gggatgactg gagcccctgg    300
cctccctgga gagcgtggag aaaagggaga gcctggcgag agaggtcctc cagggtttcc    360
agcatatcta gatgaagagc tccagggcac actccatgag atcagacatc aagtcctgca    420
gtcacagggc gtcctccgtt tgcaggggtc cgtgctggcg gtgggagaga aggtcttctc    480
taccaatggg cagtcagtca attttgatgc cattaaagag ttatgtgcca gagtaggtgg    540
```

```
acatattgct gccccgagga gtccagagga gaatgaagcc attgtgagca tcgtgaagaa      600
gtacaacact tatgcttacc tgggcctggt cgaaggcccc accgctggag acttctatta      660
cctggatgga gcccctgtga attataccaa ttggtaccca ggggagccca ggggccgggg      720
taaagagaag tgtgtagaaa tatacacaga tggtcagtgg aatgacaaga actgcctgca      780
gtaccgactg gccatctgtg agttctgagc aggcaccaaa gccacaggat ggacacagtc      840
ctatctttcc ttttagcctc catcctgggg atccacctgg tctatgaatc aggtgctata      900
attcccttgt ggctatcaga attgaaggca ctcttgagca ctccactcct gggtggatcc      960
tgactcctcc ccaatgatca ctaatcagtc tgactccccc agaacccctt ctcagcattg     1020
cactcttggc agccactcta actttgccct tctgcaagag acagaggttt ctttcctcct     1080
tttcttgtcc agttccttta tttatagatg caacagtaa ggtcctgaga tgaaggttcc      1140
ctccacagca ccacactgcc tacttcctgg ccccctcta ctctgtcttt gcagctcact      1200
gcttgcccag cctcatcaag atttagcagt gctgctcaag cacaatgata gatgtacttc     1260
tgggaaattt cacatgtgtg gagctaagga tacatttggg tttatctatc aacctgagat     1320
ctgtggggag gcatcttgtt aggctctcca tgaagtcaga gggccaggtg gtgctccagc     1380
atgatgaag ccaacttatt cctagtgatt ggcaggtatt atccacttcc ttgagtctta      1440
gggtgtcagc caacacctct aaggaagatg tcacccccac catagacatt acccaagtac     1500
ctgcctgctg atgaacacat tccccacctc ttcagaaatc agtgaggagt tcacgctcct     1560
tgtcacacca ccgtttattg agcacatact atataccaag caccgtgaca tgcacttcta     1620
agacatatga tttaatcttc acacagtgtc atgggatgag catcattttc cccaatctt t    1680
tatacaagga cactgaaatt tagagaagtt aaatgttttg catttttttt ttttttaacat    1740
gaagcaattg gcagaggctg gtttcaaacc catctacctg gacctaaagc ttgtgctcat     1800
aattacctct ccttctcatt gaacagagat gattcacgtg taataaatca tgaatgtgtt     1860
aaaaaaaaaa aaaaaaata aaaaaaaaaa aaaaaaaaa aaaaaaaaaa aaaaaaaaa        1920
aaaaaaaaaa aaaaaaaaa aaaaaaaaaa aaaaaaaaa aaaaaaaaaa aaaaaaaaa        1980
aaaaaaaaaa aaaaaaaaa aaaaaaaaaa aaaaaaaaa aaaaaaaaa aaaaaaa           2037
```

<210> SEQ ID NO 13
<211> LENGTH: 248
<212> TYPE: PRT
<213> ORGANISM: Bos sp.

<400> SEQUENCE: 13

```
Met Leu Leu Cys Ser Leu Thr Leu Thr Leu Leu Trp Met Val Ala Ser
1               5                   10                  15

Gly Leu Glu Cys Asp Val Lys Glu Val Cys Leu Gly Ser Pro Gly Ile
            20                  25                  30

Pro Gly Thr Pro Gly Ser His Gly Leu Pro Gly Arg Asp Gly Arg Asp
        35                  40                  45

Gly Ile Lys Gly Asp Pro Gly Pro Gly Pro Met Gly Pro Pro Gly
    50                  55                  60

Gly Met Pro Gly Leu Pro Gly Arg Asp Gly Met Thr Gly Ala Pro Gly
65                  70                  75                  80

Leu Pro Gly Glu Arg Gly Glu Lys Gly Glu Pro Gly Glu Arg Gly Pro
                85                  90                  95

Pro Gly Phe Pro Ala Tyr Leu Asp Glu Glu Leu Gln Gly Thr Leu His
            100                 105                 110
```

Glu Ile Arg His Gln Val Leu Gln Ser Gln Gly Val Leu Arg Leu Gln
             115                 120                 125

Gly Ser Val Leu Ala Val Gly Glu Lys Val Phe Ser Thr Asn Gly Gln
        130                 135                 140

Ser Val Asn Phe Asp Ala Ile Lys Glu Leu Cys Ala Arg Val Gly Gly
145                 150                 155                 160

His Ile Ala Ala Pro Arg Ser Pro Glu Glu Asn Glu Ala Ile Val Ser
                165                 170                 175

Ile Val Lys Lys Tyr Asn Thr Tyr Ala Tyr Leu Gly Leu Val Glu Gly
            180                 185                 190

Pro Thr Ala Gly Asp Phe Tyr Tyr Leu Asp Gly Ala Pro Val Asn Tyr
        195                 200                 205

Thr Asn Trp Tyr Pro Gly Glu Pro Arg Gly Arg Gly Lys Glu Lys Cys
    210                 215                 220

Val Glu Ile Tyr Thr Asp Gly Gln Trp Asn Asp Lys Asn Cys Leu Gln
225                 230                 235                 240

Tyr Arg Leu Ala Ile Cys Glu Phe
            245

<210> SEQ ID NO 14
<211> LENGTH: 1581
<212> TYPE: DNA
<213> ORGANISM: Bos sp.

<400> SEQUENCE: 14
ggtccaggct gtggaggtgc catggccaag tcacacctgc ttccatggct tctgctgctg      60
cccatactct gtggtccggg cactgctgct gcgatcacct attccctggc ctgtgcccag     120
ggccccgagt ctggtgtcca agtctctgag caagcattgc agtgcagagc cctagggcac     180
tgcctgcagg aagtctgggg acatgtggaa gccgatgacc tgtgccagga atgtgagaac     240
atctcccgcc tcctcaccaa gatgccaag gaggccattt ccaggactc agtgcgcaaa     300 tttctggagc aggagtgcga tgtccttccg ctgaaactgt tggcgcccct gtgtcgccac     360
ctgctggaca cctatttccc tctgatcatt gagcacttcc agagccatat gaacccgaag     420
ttcatctgtc agcacgtggg cctatgcaag cccaggcacc agagccagg gaaggggcca     480 gagccatggg gccctctgct ggacaagctg gccctccccc tgctgccagg gtccccag     540 gccaagcctg ggcctcagac acaggacctc tctgagcagc tgttcccat cccatcccc     600 tactgctggc tctgccggac tctgatcaaa cggatccagg ctgtgattcc caagggtgtt     660
ctggccatga ctgtggccca ggtgtgccac gtggtccccc tgctggtggg cggcatctgc     720
cagtgcctgg ttgagcgcta ctcggtcatc ctcctggaca cgctgctagg ccgcatgctg     780
ccccagctgt tctgcggcct cgtcctccgg tgctccagtg aggacagcgc tggcccagcc     840
ctccctgccc tggggtccgt gcctggagaa tggctgccac aagactctga ctgccagctc     900
tgcatgtttg tgaccacca ggcagggaac agcagtgagc aggccacgcc acaggcaatg     960
cgccaggcct gcctgggcac ctggctggac aggcaaaagt gtgagcggtt cgtggaggag    1020
aacgcgcccc ggctgcagac tctggtgtcc agtggctggg atgcccacat ggcctgccag    1080
gccctgggga catgtgcggc tccgttcagt cctctccagt gtgtccacag cccccacttc    1140
tgatgagaat gcacagccat ggcagcctgg aaccagaggc acttccgtcc actttgggag    1200
tgaggggtgg ccaaggcctc gtcttctgga caaggaatgc agatggggct ccggcccag    1260 ggccacctgc acatcccacc agtgccagcc caactctcac cacacccca gcactgggct    1320

```
gatgggacct tgtcgtgggc ccccagtcct tctctaagtc ctggcatcaa gaggacagcg    1380
gagggagaat cctgtgctgg cgtcactccc atctccatgt gcatgagatg ctagctttta    1440
caatcactct gctaacgctt tcacaaaatt aagaattcgg aagaataaaa gtgggaacag    1500
aaagtcccag aaaagacaaa aaaaaaaaaa aaaaaaaaaa aaaaaaaaaa aaaaaaaaaa    1560
aaaaaaaaaa aaaaaaaaaa a                                              1581

<210> SEQ ID NO 15
<211> LENGTH: 373
<212> TYPE: PRT
<213> ORGANISM: Bos sp.

<400> SEQUENCE: 15
```

| | | | | | | | | | | | | | | |
|---|---|---|---|---|---|---|---|---|---|---|---|---|---|---|
| Met | Ala | Lys | Ser | His | Leu | Leu | Pro | Trp | Leu | Leu | Leu | Pro | Ile | Leu |
| 1 | | | | 5 | | | | | 10 | | | | | 15 |
| Cys | Gly | Pro | Gly | Thr | Ala | Ala | Ile | Thr | Tyr | Ser | Leu | Ala | Cys | Ala |
| | | | 20 | | | | | 25 | | | | | 30 | |
| Gln | Gly | Pro | Glu | Phe | Trp | Cys | Gln | Ser | Leu | Glu | Gln | Ala | Leu | Gln | Cys |
| | | | 35 | | | | 40 | | | | | 45 | | |
| Arg | Ala | Leu | Gly | His | Cys | Leu | Gln | Glu | Val | Trp | Gly | His | Val | Glu | Ala |
| | 50 | | | | | 55 | | | | | 60 | | | |
| Asp | Asp | Leu | Cys | Gln | Glu | Cys | Glu | Asn | Ile | Ser | Arg | Leu | Leu | Thr | Lys |
| 65 | | | | | 70 | | | | | 75 | | | | | 80 |
| Met | Ala | Lys | Glu | Ala | Ile | Phe | Gln | Asp | Ser | Val | Arg | Lys | Phe | Leu | Glu |
| | | | | 85 | | | | | 90 | | | | | 95 | |
| Gln | Glu | Cys | Asp | Val | Leu | Pro | Leu | Lys | Leu | Leu | Ala | Pro | Leu | Cys | Arg |
| | | | 100 | | | | | 105 | | | | | 110 | | |
| His | Leu | Leu | Asp | Thr | Tyr | Phe | Pro | Leu | Ile | Ile | Glu | His | Phe | Gln | Ser |
| | | | | 115 | | | | | 120 | | | | | 125 | |
| His | Met | Asn | Pro | Lys | Phe | Ile | Cys | Gln | His | Val | Gly | Leu | Cys | Lys | Pro |
| | 130 | | | | | 135 | | | | | 140 | | | | |
| Arg | His | Pro | Glu | Pro | Gly | Lys | Gly | Pro | Glu | Pro | Trp | Gly | Pro | Leu | Leu |
| 145 | | | | | 150 | | | | | 155 | | | | | 160 |
| Asp | Lys | Leu | Ala | Leu | Pro | Leu | Leu | Pro | Gly | Val | Pro | Gln | Ala | Lys | Pro |
| | | | | 165 | | | | | 170 | | | | | 175 | |
| Gly | Pro | Gln | Thr | Gln | Asp | Leu | Ser | Glu | Gln | Leu | Phe | Pro | Ile | Pro | Ile |
| | | | 180 | | | | | 185 | | | | | 190 | | |
| Pro | Tyr | Cys | Trp | Leu | Cys | Arg | Thr | Leu | Ile | Lys | Arg | Ile | Gln | Ala | Val |
| | | | | 195 | | | | | 200 | | | | | 205 | |
| Ile | Pro | Lys | Gly | Val | Leu | Ala | Met | Thr | Val | Ala | Gln | Val | Cys | His | Val |
| | 210 | | | | | 215 | | | | | 220 | | | | |
| Val | Pro | Leu | Leu | Val | Gly | Gly | Ile | Cys | Gln | Cys | Leu | Val | Glu | Arg | Tyr |
| 225 | | | | | 230 | | | | | 235 | | | | | 240 |
| Ser | Val | Ile | Leu | Leu | Asp | Thr | Leu | Leu | Gly | Arg | Met | Leu | Pro | Gln | Leu |
| | | | | 245 | | | | | 250 | | | | | 255 | |
| Val | Cys | Gly | Leu | Val | Leu | Arg | Cys | Ser | Ser | Glu | Asp | Ser | Ala | Gly | Pro |
| | | | 260 | | | | | 265 | | | | | 270 | | |
| Ala | Leu | Pro | Ala | Leu | Gly | Ser | Val | Pro | Gly | Glu | Trp | Leu | Pro | Gln | Asp |
| | | | | 275 | | | | | 280 | | | | | 285 | |
| Ser | Asp | Cys | Gln | Leu | Cys | Met | Phe | Val | Thr | Thr | Gln | Ala | Gly | Asn | Ser |
| | 290 | | | | | 295 | | | | | 300 | | | | |
| Ser | Glu | Gln | Ala | Thr | Pro | Gln | Ala | Met | Arg | Gln | Ala | Cys | Leu | Gly | Thr |
| 305 | | | | | 310 | | | | | 315 | | | | | 320 |
| Trp | Leu | Asp | Arg | Gln | Lys | Cys | Glu | Arg | Phe | Val | Glu | Glu | Asn | Ala | Pro |

```
                    325                 330                 335
Arg Leu Gln Thr Leu Val Ser Ser Gly Trp Asp Ala His Met Ala Cys
            340                 345                 350

Gln Ala Leu Gly Thr Cys Ala Ala Pro Phe Ser Pro Leu Gln Cys Val
            355                 360                 365

His Ser Pro His Phe
        370

<210> SEQ ID NO 16
<211> LENGTH: 724
<212> TYPE: DNA
<213> ORGANISM: Bos sp.

<400> SEQUENCE: 16
atggatgtgg gcagcaaaga ggtcttgatg gagagcccgc cggactacac agcagtccct      60
gggggccggc tcctcatccc ttgctgtccc gtgaacatca aacgccttct catcgtggtc     120
gtggttgtgg tccttgttgt cgtggtgatc gtaggggccc tgctcatggg ccttcacatg     180
agccagaaac atacagagat ggttctagag atgagcatca caggcccaga agcacagcaa     240
cgcctggccc tgagtgagcg tgtgggaacc actgccactt tctccattgg ctccactggc     300
actgtggttt atgactacca gcggctcctg attgcctaca gccagccccc cggaacctgc     360
tgctacatca tgaagatggc tccgcagaac atcccaagtc tcgaggctct caccagaaaa     420
ttgcagaact tccaggccaa gccccaagtg ccttcctcga agctgggcca ggagcagggc     480
catgacgccg gctcagcatt ctctggggac ctggccttcc tggcaggac cgtgagcacc     540 ctgtgtggcg aggtgcccct gtactacacc taggactggt cagggcctca ggaagcccca     600
gagggacagc ggagatccag gagcaaaggg tcttgtgcag actggcagga agcagatcct     660
gtcgacacca ctgggactgg ccctgcagaa atgggactgt gggggaggt gggcagagga     720 gaag                                                                 724

<210> SEQ ID NO 17
<211> LENGTH: 190
<212> TYPE: PRT
<213> ORGANISM: Bos sp.

<400> SEQUENCE: 17

Met Asp Val Gly Ser Lys Glu Val Leu Met Glu Ser Pro Pro Asp Tyr
  1               5                  10                  15

Thr Ala Val Pro Gly Gly Arg Leu Leu Ile Pro Cys Cys Pro Val Asn
            20                  25                  30

Ile Lys Arg Leu Leu Ile Val Val Val Val Leu Val Val Val
        35                  40                  45

Val Ile Val Gly Ala Leu Met Gly Leu His Met Ser Gln Lys His
    50                  55                  60

Thr Glu Met Val Leu Glu Met Ser Ile Thr Gly Pro Glu Ala Gln Gln
 65                  70                  75                  80

Arg Leu Ala Leu Ser Glu Arg Val Gly Thr Thr Ala Thr Phe Ser Ile
            85                  90                  95

Gly Ser Thr Gly Thr Val Val Tyr Asp Tyr Gln Arg Leu Leu Ile Ala
            100                 105                 110

Tyr Lys Pro Ala Pro Gly Thr Cys Cys Tyr Ile Met Lys Met Ala Pro
            115                 120                 125

Gln Asn Ile Pro Ser Leu Glu Ala Leu Thr Arg Lys Leu Gln Asn Phe
        130                 135                 140
```

Gln Ala Lys Pro Gln Val Pro Ser Ser Lys Leu Gly Gln Glu Gln Gly
145                 150                 155                 160

His Asp Ala Gly Ser Ala Phe Ser Gly Asp Leu Ala Phe Leu Gly Arg
            165                 170                 175

Thr Val Ser Thr Leu Cys Gly Glu Val Pro Leu Tyr Tyr Thr
        180                 185                 190

<210> SEQ ID NO 18
<211> LENGTH: 1454
<212> TYPE: DNA
<213> ORGANISM: Bos sp.

<400> SEQUENCE: 18

```
aattccgggt gctatagttg cttcctgtag gactgcagac tccagtacta gtctgtccag      60
agcaacaagt gataggaaac aagccagcat tgtaaggaga catgcttctc ctccctctct     120
ccgtgctgct cctgctcaca cagccctgga gatccctggg agcagaaatg aagatctatt     180
cccagaaaac aatggccaac gcctgtaccc tggtcatgtg tagccccccg gaggatggtt     240
tgcctggtcg tgatggacga gatgggagag aaggcccccg ggggagaag ggagatccag      300
gttcaccagg acctgcagga cgagcaggaa tgcctggacc agctggccct attgggctga     360
aaggagacaa tggctctgct ggagaacccg gaccaaaggg agacactgga ccacctgggc     420
ctccaggtat gcctggacca gctggaagag agggcccctc aggaagcag gggagcatgg      480
gacctccagg cacaccaggc cccaaggaga cactgggcc caaggagga gtgggtgccc       540
caggcattca gggctcccca ggccctgcag gtctcaaagg agagagagt gccctggtg       600
agcccggagc ccctggacgt gctggggcac cagggcctgc tggagccata ggtccacagg     660
ggccttcagg tgccaggggc cccccaggac tgaaggaga cagaggtact cctggagaaa      720
gaggagcaaa gggggagagt gggcttgcag aggtcaatgc tctcaggcag cgggtgggaa     780
tcttagaggg acaactacaa cggctccaga atgcccttctc tcagtataag aaagcgatgc    840
tcttccctaa tggccggagt gtcggggaga agatctttaa gacggtaggc tctgaaaaaa    900
cgtttcagga tgcccagcag atctgcacac aggctggagg acagttgccc tccccacgtt     960
ctggagctga aaacgaggcc ttgactcagc tggccacagc ccagaacaag gctgctttcc    1020
tgagcatgag cgacaccagg aaggagggta ctttcatcta ccccacgggg gagcccctgg    1080
tctattccaa ctgggccccc aggagcccca caatgatgg cggctcagag aactgtgtgg     1140
agatctttcc caatggcaag tggaatgaca agtctgcgg agagcagcgc tcgtgatct       1200
gcgagttctg agctcctcct gcacacacac acacacatag tgtgtgtgtt ggggcggtgg    1260
gggtcggggg gggggatggg cagtgcccag agctgcattt ttccagtgtt tgaataaaat    1320
agtgaccctc tactggccag ggcttctcca cagagccaca ggataaggcc agaggcaggg    1380
ctcctatgga atacatccct cagaataaag tttgaaactg gcttcacaca aaaaaaaaa    1440
aaaaaccgga attc                                                      1454
```

<210> SEQ ID NO 19
<211> LENGTH: 369
<212> TYPE: PRT
<213> ORGANISM: Bos sp.

<400> SEQUENCE: 19

Met Leu Leu Leu Pro Leu Ser Val Leu Leu Leu Thr Gln Pro Trp
1                 5                   10                  15

Arg Ser Leu Gly Ala Glu Met Lys Ile Tyr Ser Gln Lys Thr Met Ala
            20                  25                  30

Asn Ala Cys Thr Leu Val Met Cys Ser Pro Pro Glu Asp Gly Leu Pro
            35                  40                  45

Gly Arg Asp Gly Arg Asp Gly Arg Glu Gly Pro Arg Gly Glu Lys Gly
50                  55                  60

Asp Pro Gly Ser Pro Gly Pro Ala Gly Arg Ala Gly Met Pro Gly Pro
65                  70                  75                  80

Ala Gly Pro Ile Gly Leu Lys Gly Asp Asn Gly Ser Ala Gly Glu Pro
                85                  90                  95

Gly Pro Lys Gly Asp Thr Gly Pro Pro Gly Pro Pro Gly Met Pro Gly
            100                 105                 110

Pro Ala Gly Arg Glu Gly Pro Ser Gly Lys Gln Gly Ser Met Gly Pro
            115                 120                 125

Pro Gly Thr Pro Gly Pro Lys Gly Asp Thr Gly Pro Lys Gly Gly Val
            130                 135                 140

Gly Ala Pro Gly Ile Gln Gly Ser Pro Gly Pro Ala Gly Leu Lys Gly
145                 150                 155                 160

Glu Arg Gly Ala Pro Gly Glu Pro Gly Ala Pro Gly Arg Ala Gly Ala
                165                 170                 175

Pro Gly Pro Ala Gly Ala Ile Gly Pro Gln Gly Pro Ser Gly Ala Arg
            180                 185                 190

Gly Pro Pro Gly Leu Lys Gly Asp Arg Gly Thr Pro Gly Glu Arg Gly
            195                 200                 205

Ala Lys Gly Glu Ser Gly Leu Ala Glu Val Asn Ala Leu Arg Gln Arg
210                 215                 220

Val Gly Ile Leu Glu Gly Gln Leu Gln Arg Leu Gln Asn Ala Phe Ser
225                 230                 235                 240

Gln Tyr Lys Lys Ala Met Leu Phe Pro Asn Gly Arg Ser Val Gly Glu
                245                 250                 255

Lys Ile Phe Lys Thr Val Gly Ser Glu Lys Thr Phe Gln Asp Ala Gln
            260                 265                 270

Gln Ile Cys Thr Gln Ala Gly Gly Gln Leu Pro Ser Pro Arg Ser Gly
            275                 280                 285

Ala Glu Asn Glu Ala Leu Thr Gln Leu Ala Thr Ala Gln Asn Lys Ala
290                 295                 300

Ala Phe Leu Ser Met Ser Asp Thr Arg Lys Glu Gly Thr Phe Ile Tyr
305                 310                 315                 320

Pro Thr Gly Glu Pro Leu Val Tyr Ser Asn Trp Ala Pro Gln Glu Pro
                325                 330                 335

Asn Asn Asp Gly Gly Ser Glu Asn Cys Val Glu Ile Phe Pro Asn Gly
            340                 345                 350

Lys Trp Asn Asp Lys Val Cys Gly Glu Gln Arg Leu Val Ile Cys Glu
            355                 360                 365

Phe

<210> SEQ ID NO 20
<211> LENGTH: 353
<212> TYPE: DNA
<213> ORGANISM: Sus sp.

<400> SEQUENCE: 20
tggcagtggg agagaaggtc ttctccacca atgggcagtc agtcgctttt gatgtcatta      60
gagagttgtg tgccagagca ggtggacgca tcgctgcccc aaggagtcca gaggagaatg     120

```
aggccattgc aagcattgtg aagaaacaca acacttatgc ttacctcggc ctggttgagg      180
gccccactgc tggagacttc ttctacttgg atgaacccc tgtgaattac accaactggt      240
acccagggga acccagggt cggggcaaag agaagtgtgt ggagatgtac acagatggcc      300
agtggaatga caggaactgc cagcagtacc gactggccat atgtgagttt tga            353
```

```
<210> SEQ ID NO 21
<211> LENGTH: 116
<212> TYPE: PRT
<213> ORGANISM: Sus sp.

<400> SEQUENCE: 21
```

Ala Val Gly Glu Lys Val Phe Ser Thr Asn Gly Gln Ser Val Ala Phe
1               5                   10                  15

Asp Val Ile Arg Glu Leu Cys Ala Arg Ala Gly Gly Arg Ile Ala Ala
            20                  25                  30

Pro Arg Ser Pro Glu Glu Asn Glu Ala Ile Ala Ser Ile Val Lys Lys
        35                  40                  45

His Asn Thr Tyr Ala Tyr Leu Gly Leu Val Glu Gly Pro Thr Ala Gly
    50                  55                  60

Asp Phe Phe Tyr Leu Asp Gly Thr Pro Val Asn Tyr Thr Asn Trp Tyr
65                  70                  75                  80

Pro Gly Glu Pro Arg Gly Arg Gly Lys Glu Lys Cys Val Glu Met Tyr
                85                  90                  95

Thr Asp Gly Gln Trp Asn Asp Arg Asn Cys Gln Gln Tyr Arg Leu Ala
            100                 105                 110

Ile Cys Glu Phe
        115

```
<210> SEQ ID NO 22
<211> LENGTH: 244
<212> TYPE: DNA
<213> ORGANISM: Sus sp.

<400> SEQUENCE: 22
```

```
ctttccgctg gtcgttgatc acttccagag ccaaatgaac ctgaaggcca tctgcaagca      60
cttgggcctg tgcaaacctg agcatccaga gccaggccag gggccagagc tgacaggctc     120
tctgctggac aagctggccc tccccctgct gcccgcaggc ctccaggcga ggcctgggcc     180
tcagacacag gatctctcca agcagaagtt ccccattcct cttcccttct gctggctctg     240
cagg                                                                   244
```

```
<210> SEQ ID NO 23
<211> LENGTH: 81
<212> TYPE: PRT
<213> ORGANISM: Sus sp.

<400> SEQUENCE: 23
```

Phe Pro Leu Val Val Asp His Phe Gln Ser Gln Met Asn Leu Lys Ala
1               5                   10                  15

Ile Cys Lys His Leu Gly Leu Cys Lys Pro Glu His Pro Glu Pro Gly
            20                  25                  30

Gln Gly Pro Glu Leu Thr Gly Ser Leu Leu Asp Lys Leu Ala Leu Pro
        35                  40                  45

Leu Leu Pro Ala Gly Leu Gln Ala Arg Pro Gly Pro Gln Thr Gln Asp
    50                  55                  60

```
Leu Ser Lys Gln Lys Phe Pro Ile Pro Leu Pro Phe Cys Trp Leu Cys
 65                  70                  75                  80

Arg

<210> SEQ ID NO 24
<211> LENGTH: 867
<212> TYPE: DNA
<213> ORGANISM: Sus sp.

<400> SEQUENCE: 24
ctctccctcc tggtgcatat aagaccctgg tcacacttgg ggatgagcag gggaaggtgc      60
ctacagcaag atggatgtag gcagcaaaga agtcctgatg gagagcccgc cggactactc     120
agcagtccca gggggccggc tccgcatccc ctgctgtcct gtgaacctca aacgccttct     180
tgtcgtggtc gtggtggtgg ttcttgtcgt cgtggtgatt gtaggggccc tgctcatggg     240
tcttcacatg agccagaaac atactgagat ggtcctagag atgagcctcg cagggccaga     300
agcccagcaa cgcctggccc tgagtgagca tgtgggaacc actgccacct tctccattgg     360
ctctagtggc aatgtggtct atgactacca gcggctcctg attgcctaca gccagcccc      420 gggaacctgc tgctatgtca tgaagatgtc tccgcagagt atgccgagtc ttgaggctct     480
caccaaaaaa ttccagaact ccaggccaa gccctcgacg cctacctcta agctgggcca     540
ggaggagggc cgtgtcgctg gctcagcacc ctccggggac ctggccttcc tgggcagcac     600
catgagcacc ctgtgtggcg aagtgcccct cttgtacatc taggaaacat cagggcctca     660
ggaagcccca agaggacagc aaagatccag gagcaaagag tcttgtgcag actcacagga     720
agccgcttct gggacaccac ggggactggc cctggagaaa tgggagctgt ggggagaggt     780
gggcagagga gaagcagctg ttaggggccc gggggcttct accaccaaag aataaagcag     840
cctgattgaa aaaaaaaaaa aaaaaaa                                         867

<210> SEQ ID NO 25
<211> LENGTH: 190
<212> TYPE: PRT
<213> ORGANISM: Sus sp.

<400> SEQUENCE: 25

Met Asp Val Gly Ser Lys Glu Val Leu Met Glu Ser Pro Pro Asp Tyr
 1               5                  10                  15

Ser Ala Val Pro Gly Gly Arg Leu Arg Ile Pro Cys Cys Pro Val Asn
                 20                  25                  30

Leu Lys Arg Leu Leu Val Val Val Val Val Leu Val Val Val
             35                  40                  45

Val Ile Val Gly Ala Leu Leu Met Gly Leu His Met Ser Gln Lys His
         50                  55                  60

Thr Glu Met Val Leu Glu Met Ser Leu Ala Gly Pro Glu Ala Gln Gln
 65                  70                  75                  80

Arg Leu Ala Leu Ser Glu His Val Gly Thr Thr Ala Thr Phe Ser Ile
                 85                  90                  95

Gly Ser Ser Gly Asn Val Val Tyr Asp Tyr Gln Arg Leu Leu Ile Ala
                100                 105                 110

Tyr Lys Pro Ala Pro Gly Thr Cys Cys Tyr Val Met Lys Met Ser Pro
            115                 120                 125

Gln Ser Met Pro Ser Leu Glu Ala Leu Thr Lys Lys Phe Gln Asn Phe
        130                 135                 140

Gln Ala Lys Pro Ser Thr Pro Thr Ser Lys Leu Gly Gln Glu Glu Gly
```

```
                145                 150                 155                 160
Arg Val Ala Gly Ser Ala Pro Ser Gly Asp Leu Ala Phe Leu Gly Ser
                        165                 170                 175

Thr Met Ser Thr Leu Cys Gly Glu Val Pro Leu Leu Tyr Ile
            180                 185                 190

<210> SEQ ID NO 26
<211> LENGTH: 1385
<212> TYPE: DNA
<213> ORGANISM: Sus sp.

<400> SEQUENCE: 26
cgagtttgcc tggagattct gagctctaga ggacgcaact gacatgcttc tcctccctct     60
ctccgtgctg atcctgctca cacagccccc gaggtcactg ggagcagaaa tgaagaccta    120
ttcccagaga gcagtggcca acgcctgcgc cctggtcatg tgtagcccca tggagaatgg    180
cctgcctggt cgtgatggtc gggatggag  agagggccct cggggcgaga aggggggatcc    240
aggtttgcca ggagctgtag gcgagcggg  gatgcctgga ctggctggcc cagttgggcc    300
caaaggggac aacggctcta ctggagaacc cggagcaaag ggagacattg gaccatgcgg    360
gcctccagga cctccaggta tacctggtcc agccggaaaa gaaggtccct cagggcagca    420
ggggaacata ggacctccag gcacaccagg ccccaaagga gagactgggc caaaggaga     480
agtgggtgcc ctgggcatgc agggctctac aggggcaaga ggccctgcag gtcttaaagg    540
agagagaggt gcccccggtg agcgtggagc ccctggaagt gctgggcag  cagggcctgc    600
tggagccacg ggccctcagg gcccttcagg tgccaggggc cccccaggac tgaaagggga    660
cagaggtcct cctggagaaa gaggagccaa gggagagagt ggactcccag gcatcactgc    720
tctgaggcaa caggtggaga ccttacaggg gcaggtacaa cgcctccaga aggccttctc    780
tcagtataag aaagtggagc tcttccccaa tggccgaggt gtcggggaga agatcttcaa    840
gacgggaggc tttgaaaaga cttttcagga tgctcagcag gtatgcacac aggccgggg     900
acagatggcc tccccacgct ctgagactga aacgaggcc  ttgagccagc tggtcacagc    960
tcagaataag gctgcttc   tgagcatgac tgacatcaag acggaggca  atttcaccta    1020
ccccacgggg gagcccctgg tctatgccaa ctgggcccct ggggagccca caacaatgg     1080
tgcagcagc  ggagcagaga actgtgtgga gatctttccc aatggcaagt ggaatgacaa    1140
ggcctgcgga gaactgcgcc tcgtgatctg cgagttctga gcccctgggg agggaggggc    1200
ggtgtccaga gctgtgtgct accaacgtcc caataaatag gtgaccttct gctggccagg    1260
gcttctccac agagccgtgg gacgaggcca gaaggtaggg agcctatgga acgcctccct    1320
cagaataaag tacgaaactg gcctcacaaa aaaaaaaaa  aaaaaaaaa  aaaaaaaaa     1380
aaaaa                                                                1385

<210> SEQ ID NO 27
<211> LENGTH: 378
<212> TYPE: PRT
<213> ORGANISM: Sus sp.

<400> SEQUENCE: 27

Met Leu Leu Leu Pro Leu Ser Val Leu Ile Leu Leu Thr Gln Pro Pro
1               5                   10                  15

Arg Ser Leu Gly Ala Glu Met Lys Thr Tyr Ser Gln Arg Ala Val Ala
                20                  25                  30

Asn Ala Cys Ala Leu Val Met Cys Ser Pro Met Glu Asn Gly Leu Pro
```

```
                35                  40                  45
Gly Arg Asp Gly Arg Asp Gly Arg Glu Gly Pro Arg Gly Glu Lys Gly
 50                  55                  60

Asp Pro Gly Leu Pro Gly Ala Val Gly Arg Ala Gly Met Pro Gly Leu
 65                  70                  75                  80

Ala Gly Pro Val Gly Pro Lys Gly Asp Asn Gly Ser Thr Gly Glu Pro
                 85                  90                  95

Gly Ala Lys Gly Asp Ile Gly Pro Cys Gly Pro Gly Pro Pro Gly
            100                 105                 110

Ile Pro Gly Pro Ala Gly Lys Glu Gly Pro Ser Gly Gln Gln Gly Asn
            115                 120                 125

Ile Gly Pro Pro Gly Thr Pro Gly Pro Lys Gly Glu Thr Gly Pro Lys
            130                 135                 140

Gly Glu Val Gly Ala Leu Gly Met Gln Gly Ser Thr Gly Ala Arg Gly
145                 150                 155                 160

Pro Ala Gly Leu Lys Gly Glu Arg Gly Ala Pro Gly Glu Arg Gly Ala
                165                 170                 175

Pro Gly Ser Ala Gly Ala Ala Gly Pro Ala Gly Ala Thr Gly Pro Gln
            180                 185                 190

Gly Pro Ser Gly Ala Arg Gly Pro Pro Gly Leu Lys Gly Asp Arg Gly
            195                 200                 205

Pro Pro Gly Glu Arg Gly Ala Lys Gly Glu Ser Gly Leu Pro Gly Ile
210                 215                 220

Thr Ala Leu Arg Gln Gln Val Glu Thr Leu Gln Gly Gln Val Gln Arg
225                 230                 235                 240

Leu Gln Lys Ala Phe Ser Gln Tyr Lys Lys Val Glu Leu Phe Pro Asn
                245                 250                 255

Gly Arg Gly Val Gly Glu Lys Ile Phe Lys Thr Gly Phe Glu Lys
            260                 265                 270

Thr Phe Gln Asp Ala Gln Gln Val Cys Thr Gln Ala Gly Gly Gln Met
            275                 280                 285

Ala Ser Pro Arg Ser Glu Thr Glu Asn Glu Ala Leu Ser Gln Leu Val
290                 295                 300

Thr Ala Gln Asn Lys Ala Ala Phe Leu Ser Met Thr Asp Ile Lys Thr
305                 310                 315                 320

Glu Gly Asn Phe Thr Tyr Pro Thr Gly Glu Pro Leu Val Tyr Ala Asn
                325                 330                 335

Trp Ala Pro Gly Glu Pro Asn Asn Gly Gly Ser Ser Gly Ala Glu
            340                 345                 350

Asn Cys Val Glu Ile Phe Pro Asn Gly Lys Trp Asn Asp Lys Ala Cys
            355                 360                 365

Gly Glu Leu Arg Leu Val Ile Cys Glu Phe
370                 375

<210> SEQ ID NO 28
<211> LENGTH: 1901
<212> TYPE: DNA
<213> ORGANISM: Ovis sp.

<400> SEQUENCE: 28
agcatgggct gtgttcgtgc aggaggagcc gctggagcag gcgccatgct gctgtgctct    60 ttgacccta tgctcctctg gatggtggct tctggcctcg agtgcgacac aaaggaagtt    120
tgtcttggaa gccctggcat tcctggcact cccggatccc atggcctgcc aggaagagat   180
```

| | |
|---|---|
| gggagagatg gtatcaaagg agaccctggg cctccaggcc ccatgggccc cctggagga | 240 |
| atgccaggcc tccctgggcg tgatgggatg actggagccc ctggcctccc tggagaacgt | 300 |
| ggagaaaagg gagagcctgg cgagagaggt cctccagggt ttccagcgta tctagatgaa | 360 |
| gagctccagg gcacactcca tgagatcaga catcaagtcc tgcagtcaca gggcgtcctc | 420 |
| attttgcagg ggtccatgct ggaagtggga gagaaggtct tctctaccaa tgggcagtca | 480 |
| ctcaattttg atgccattaa agagttatgt gccagagcag gtggacacat cgctgcccca | 540 |
| aggagtccgg aggagaatga ggccattacc agcatcgtga agaagcacaa cacttatgct | 600 |
| tacctggggc tggctgaagg ccccaccgct ggagacttct attacctgga tggagcccct | 660 |
| gtgaattata ccaactggta cccaggggag cccaggggcc ggggtaaaga gaagtgtgta | 720 |
| gagatataca cagatggtca gtggaatgac aagaactgcc tgcagtaccg actggccatc | 780 |
| tgtgagttct gagcaggcac caaagccaca ggatggacag agtcctatct ttcctttcag | 840 |
| cctccatcct gggaatccac ctggtctatg gatcaggtgc tataattcct ttgtggctat | 900 |
| cagaagtgaa ggcactcttg atcactccac tcctgggtgg atcctaactc ctccccaatg | 960 |
| atcactaatc agtctgactc ccccagaacc ccttctcagc attgcactct ggcagccac | 1020 |
| tctaactttg cccttctgca agagacagag gtttctttcc tcctcttctt gtccagttcc | 1080 |
| tttatttata gatggcaaca gtaaggtcct gagatgaagg ttccctccat agcaccacac | 1140 |
| tgggtgcctg cttcctggcc ccctctactc tgtctttgca gctcactgct tgcccagcct | 1200 |
| catcaagatt tagcagttct gctcaagcac aatgataggt ggacttctgg gaaatttcac | 1260 |
| acatgtggag ctaaggatac atttgggttt atctatcaac ctgagatcta tggggaggca | 1320 |
| tcttgttagg ctctccatga agtcagaggg tcaggtggtg ctccagcatg atggaggcca | 1380 |
| atttattcct agtgattggc aggtattatc cacttccttg agtcttgggg tgtcagccag | 1440 |
| cgcctctaag gaagatctta ccccaccgt agacattacc caagtaactg cctgctgatg | 1500 |
| aacacattcc ccacctcttc agaactcagt gaggagttca caccacttgt cacaccacca | 1560 |
| tttattgagc acatactata caccaagcac cttgacatgc acttctaaaa catcttatgt | 1620 |
| gatttaatct tcacacagtg tcatgggatg agcattattt tccccaatct tttatataac | 1680 |
| aacgctgaaa tttagagaag ttaaatgttt tgagtttctt tttttaaaca tgaagcaatt | 1740 |
| ggcagaggct ggtttcaaac tcatctacct ggacctgaag cttgtgctca taaccacccc | 1800 |
| acctcactga acagagatga ttcaagtgta ataaatcatg actgtgttaa aaaaaaaaa | 1860 |
| aaaaaaaaa aaaaaaaaaa aaaaaaaaaa aaaaaaaaa a | 1901 |

<210> SEQ ID NO 29
<211> LENGTH: 248
<212> TYPE: PRT
<213> ORGANISM: Ovis sp.

<400> SEQUENCE: 29

Met Leu Leu Cys Ser Leu Thr Leu Met Leu Leu Trp Met Val Ala Ser
1               5                   10                  15

Gly Leu Glu Cys Asp Thr Lys Glu Val Cys Leu Gly Ser Pro Gly Ile
            20                  25                  30

Pro Gly Thr Pro Gly Ser His Gly Leu Pro Gly Arg Asp Gly Arg Asp
        35                  40                  45

Gly Ile Lys Gly Asp Pro Gly Pro Pro Gly Met Gly Pro Pro Gly
    50                  55                  60

Gly Met Pro Gly Leu Pro Gly Arg Asp Gly Met Thr Gly Ala Pro Gly

```
            65                  70                  75                  80
Leu Pro Gly Glu Arg Gly Glu Lys Gly Glu Pro Gly Glu Arg Gly Pro
                        85                  90                  95

Pro Gly Phe Pro Ala Tyr Leu Asp Glu Glu Leu Gln Gly Thr Leu His
                100                 105                 110

Glu Ile Arg His Gln Val Leu Gln Ser Gln Gly Val Leu Ile Leu Gln
            115                 120                 125

Gly Ser Met Leu Glu Val Gly Glu Lys Val Phe Ser Thr Asn Gly Gln
        130                 135                 140

Ser Leu Asn Phe Asp Ala Ile Lys Glu Leu Cys Ala Arg Ala Gly Gly
145                 150                 155                 160

His Ile Ala Ala Pro Arg Ser Pro Glu Glu Asn Glu Ala Ile Thr Ser
                165                 170                 175

Ile Val Lys Lys His Asn Thr Tyr Ala Tyr Leu Gly Leu Ala Glu Gly
            180                 185                 190

Pro Thr Ala Gly Asp Phe Tyr Tyr Leu Asp Gly Ala Pro Val Asn Tyr
        195                 200                 205

Thr Asn Trp Tyr Pro Gly Glu Pro Arg Gly Arg Gly Lys Glu Lys Cys
    210                 215                 220

Val Glu Ile Tyr Thr Asp Gly Gln Trp Asn Asp Lys Asn Cys Leu Gln
225                 230                 235                 240

Tyr Arg Leu Ala Ile Cys Glu Phe
                245

<210> SEQ ID NO 30
<211> LENGTH: 1660
<212> TYPE: DNA
<213> ORGANISM: Ovis sp.

<400> SEQUENCE: 30
gccaagtcac gcctgctgcc gtggctgctg ctgctgctgc ccatgctctg tggtctgggc      60
tctgcagctg tggggaccac ctactccctg acctgtgccc agggccccac attctggtgc     120
caaagtctgg agcaagcttt gcagtgcaga gccctagggc actgcctgca ggaagtctgg     180
ggacatgcgg aagccgatga cctgtgccag gaatgtgaga catctcccg catcctcacc      240 aagatggcca aggaggccat tttccaggac acagtgcgca aattcctgga gcaggagtgc     300
gatgttcttc cgctgaaact cttggtgccc agtgtcgcc acctgctgga cacctacttc      360
cctctgatca ttgaccactt ccagagccag atgaacccga agttcatctg tcagcatgtg     420
ggcctatgca agcccaggca cccagagcca gggaaggggc cagagccatg gggtcctctg     480
ctggacaaga tggccctccc cctgctgcca ggggccctcc aggccaagcc tgggcctcag     540
acacaggacc tctcccagca gcggttcccc atccctctcc ccttctgctg gctctgccgg     600
actctgatca aacgaatcca ggctgtgatt cccaagggtg tactggccat gactgtggcc     660
caggtgtgcc acgtggtccc cctgctggtg ggcggcatct gccagtgcct ggttgagcgc     720
tactctgtca tcctcctgga cacgctgcta ggccgcatgc tgcccagct ggtctgcggc      780 ctcgtcctcc ggtgctccag cgaggacagc gctggcccag ccctccctgc cctggggtcc     840
ctgcctggag aatggctgcc acaagactct gagtgccagc tctgcatgtt tgtgaccact     900
caggcaggga cagcagtga gcaggccatg ccacaggcaa tgcgccaggc ctgcctgggc     960
acctggctgg acaggcaaaa gtgtgagcag tttgtggagg agcatgcgcc ccggctacag    1020
actctggtgt ccagcggctg ggatgcccac atggcctgcc aggccctggg gacatgtgcg    1080
```

-continued

```
actccgttca gtcctctcca gtgtatccac agccccccact tctgatgaga acgcacagcc   1140
atggcaggct gaactcaagg ctcctgaggg ccccggcagc accatctcga ctgtcctctc   1200
tcaaacccgc tcacccctct gcccagaatc cccatggcgt tcagtgccag gcccggctcc   1260
cagcttgctg gccctccccc agcccagagg gaagcttccg tgcctgacca tggcttttcc   1320
ctcacagacc accctctgca tgcactgatc ctcagtacca aatgtgcttg caccaagccc   1380
tgcctttcct gaaactcagg ggacaccaga cattgctccc caaagatgcc aggaactcct   1440
ccatcgcctg actcctccta cctgagactc ctccctgtct ccctcaatgt cactgggtca   1500
gaggtgaccc cttaggacag agtggggtc agaggcagac tccatgccag gtgcctccgg   1560
agagggaagc gccctgaga agagacctgg caacttcaca gttctgtcca gagcaagccc   1620
ccaacatgaa ggtcatgtat tcaaaaaaaa aaaaaaaaa                          1660
```

<210> SEQ ID NO 31
<211> LENGTH: 374
<212> TYPE: PRT
<213> ORGANISM: Ovis sp.

<400> SEQUENCE: 31

```
Ala Lys Ser Arg Leu Leu Pro Trp Leu Leu Leu Leu Pro Met Leu
  1               5                  10                  15

Cys Gly Leu Gly Ser Ala Ala Val Gly Thr Thr Tyr Ser Leu Thr Cys
             20                  25                  30

Ala Gln Gly Pro Thr Phe Trp Cys Gln Ser Leu Glu Gln Ala Leu Gln
         35                  40                  45

Cys Arg Ala Leu Gly His Cys Leu Gln Glu Val Trp Gly His Ala Glu
     50                  55                  60

Ala Asp Asp Leu Cys Gln Glu Cys Glu Asn Ile Ser Arg Ile Leu Thr
 65                  70                  75                  80

Lys Met Ala Lys Glu Ala Ile Phe Gln Asp Thr Val Arg Lys Phe Leu
                 85                  90                  95

Glu Gln Glu Cys Asp Val Leu Pro Leu Lys Leu Leu Val Pro Gln Cys
            100                 105                 110

Arg His Leu Leu Asp Thr Tyr Phe Pro Leu Ile Ile Asp His Phe Gln
        115                 120                 125

Ser Gln Met Asn Pro Lys Phe Ile Cys Gln His Val Gly Leu Cys Lys
    130                 135                 140

Pro Arg His Pro Glu Pro Gly Lys Gly Pro Glu Pro Trp Gly Pro Leu
145                 150                 155                 160

Leu Asp Lys Met Ala Leu Pro Leu Leu Pro Gly Ala Leu Gln Ala Lys
                165                 170                 175

Pro Gly Pro Gln Thr Gln Asp Leu Ser Gln Gln Arg Phe Pro Ile Pro
            180                 185                 190

Leu Pro Phe Cys Trp Leu Cys Arg Thr Leu Ile Lys Arg Ile Gln Ala
        195                 200                 205

Val Ile Pro Lys Gly Val Leu Ala Met Thr Val Ala Gln Val Cys His
    210                 215                 220

Val Val Pro Leu Leu Val Gly Gly Ile Cys Gln Cys Leu Val Glu Arg
225                 230                 235                 240

Tyr Ser Val Ile Leu Leu Asp Thr Leu Leu Gly Arg Met Leu Pro Gln
                245                 250                 255

Leu Val Cys Gly Leu Val Leu Arg Cys Ser Ser Glu Asp Ser Ala Gly
            260                 265                 270
```

Pro Ala Leu Pro Ala Leu Gly Ser Leu Pro Gly Glu Trp Leu Pro Gln
                275                 280                 285

Asp Ser Glu Cys Gln Leu Cys Met Phe Val Thr Thr Gln Ala Gly Asn
        290                 295                 300

Ser Ser Glu Gln Ala Met Pro Gln Ala Met Arg Gln Ala Cys Leu Gly
305                 310                 315                 320

Thr Trp Leu Asp Arg Gln Lys Cys Glu Gln Phe Val Glu Glu His Ala
                325                 330                 335

Pro Arg Leu Gln Thr Leu Val Ser Ser Gly Trp Asp Ala His Met Ala
            340                 345                 350

Cys Gln Ala Leu Gly Thr Cys Ala Thr Pro Phe Ser Pro Leu Gln Cys
        355                 360                 365

Ile His Ser Pro His Phe
    370

<210> SEQ ID NO 32
<211> LENGTH: 809
<212> TYPE: DNA
<213> ORGANISM: Ovis sp.

<400> SEQUENCE: 32
gtctacagca agatggatgt gggcagcaaa gaggtcttga tggagagccc gccggactac      60
tcagcagtcc ccgggggccg gctccgcatc ccctgctgtc ccgtgaacat caaacgcctt     120
ctcatcgtgg ttgtggttgt ggtccttgtc gtcgtggtga tcgtaggagc cctgctcatg     180
ggtcttcaca tgagccagaa acatacagag atggttctag atgagcat cgcaggcccg       240 gaagcacagc aacgcctggc cctgagtgag cgtgtgggaa ccactgccac tttctccatc     300
ggctccactg gcactgtggt gtatgactac cagcggctcc tgattgccta caagccagcc     360
cccggaacct gctgctacat tatgaaggtg gctccgcaga gcatcccaag tctcgaggct     420
ctcactagaa aattgccgaa cttccaggcc aagcccccag tgccttcctc gaagctgggc     480
caggagcagg gccgtgacgc cggctcagca ttctctgggg acctggcctt cctgggcagg     540
accgtgagca ccctgtgtgg cgaggtgccc ctgtactaca cttaggactg gtcagggcct     600
caggaagccc caaagggaca gtggagatcc aggagcaaag gtcttgtgc agattggcag      660 gaagtggata ctgtcgacac cactgggact ggccctggag aaatgggagc tgtggggaga     720
ggtgggcaga ggagaagcag ttcctagggc ccaaggggc tcctaccacc aaagattaaa      780
gcatcctgat tgcaaaaaaa aaaaaaaaa                                       809

<210> SEQ ID NO 33
<211> LENGTH: 190
<212> TYPE: PRT
<213> ORGANISM: Ovis sp.

<400> SEQUENCE: 33

Met Asp Val Gly Ser Lys Glu Val Leu Met Glu Ser Pro Pro Asp Tyr
1               5                   10                  15

Ser Ala Val Pro Gly Gly Arg Leu Arg Ile Pro Cys Cys Pro Val Asn
            20                  25                  30

Ile Lys Arg Leu Leu Ile Val Val Val Val Val Leu Val Val Val Val
        35                  40                  45

Val Ile Val Gly Ala Leu Leu Met Gly Leu His Met Ser Gln Lys His
    50                  55                  60

Thr Glu Met Val Leu Glu Met Ser Ile Ala Gly Pro Glu Ala Gln Gln
65              70                  75                  80

```
Arg Leu Ala Leu Ser Glu Arg Val Gly Thr Thr Ala Thr Phe Ser Ile
                85                  90                  95

Gly Ser Thr Gly Thr Val Val Tyr Asp Tyr Gln Arg Leu Leu Ile Ala
            100                 105                 110

Tyr Lys Pro Ala Pro Gly Thr Cys Cys Tyr Ile Met Lys Val Ala Pro
        115                 120                 125

Gln Ser Ile Pro Ser Leu Glu Ala Leu Thr Arg Lys Leu Pro Asn Phe
    130                 135                 140

Gln Ala Lys Pro Pro Val Pro Ser Ser Lys Leu Gly Gln Glu Gln Gly
145                 150                 155                 160

Arg Asp Ala Gly Ser Ala Phe Ser Gly Asp Leu Ala Phe Leu Gly Arg
                165                 170                 175

Thr Val Ser Thr Leu Cys Gly Glu Val Pro Leu Tyr Tyr Thr
                180                 185                 190

<210> SEQ ID NO 34
<211> LENGTH: 304
<212> TYPE: DNA
<213> ORGANISM: Ovis sp.

<400> SEQUENCE: 34
ttccctgatg gccggagtgt cgggaagaag atctttaaga cggcaggctc tgaaaaaacg      60
tttcaggatg cccagcaggt ctgcacacag gctggaggac agctgccctc cccacgttct    120
gcagctgaga atgaggcttt gactcagctg ccacagccc agaacaagac tgctttcctg    180
agcatgaccg ataccaggaa ggagggtact ttcatctacc ccacggggga gcccctggtc    240
tattccaact gggccccccca ggagcccaac aatgatggcg gctcagagaa ctgtgtggag    300
atct                                                                  304

<210> SEQ ID NO 35
<211> LENGTH: 101
<212> TYPE: PRT
<213> ORGANISM: Ovis sp.

<400> SEQUENCE: 35

Phe Pro Asp Gly Arg Ser Val Gly Lys Lys Ile Phe Lys Thr Ala Gly
1               5                   10                  15

Ser Glu Lys Thr Phe Gln Asp Ala Gln Gln Val Cys Thr Gln Ala Gly
                20                  25                  30

Gly Gln Leu Pro Ser Pro Arg Ser Ala Ala Glu Asn Glu Ala Leu Thr
            35                  40                  45

Gln Leu Ala Thr Ala Gln Asn Lys Thr Ala Phe Leu Ser Met Thr Asp
    50                  55                  60

Thr Arg Lys Glu Gly Thr Phe Ile Tyr Pro Thr Gly Glu Pro Leu Val
65                  70                  75                  80

Tyr Ser Asn Trp Ala Pro Gln Glu Pro Asn Asn Asp Gly Gly Ser Glu
                85                  90                  95

Asn Cys Val Glu Ile
            100

<210> SEQ ID NO 36
<211> LENGTH: 77
<212> TYPE: PRT
<213> ORGANISM: Homo sapiens

<400> SEQUENCE: 36
```

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys
65                  70                  75

<210> SEQ ID NO 37
<211> LENGTH: 76
<212> TYPE: PRT
<213> ORGANISM: Homo sapiens

<400> SEQUENCE: 37

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg
65                  70                  75

<210> SEQ ID NO 38
<211> LENGTH: 75
<212> TYPE: PRT
<213> ORGANISM: Homo sapiens

<400> SEQUENCE: 38

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu
65                  70                  75

<210> SEQ ID NO 39
<211> LENGTH: 74
<212> TYPE: PRT
<213> ORGANISM: Homo sapiens

<400> SEQUENCE: 39

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg

```
                    50                  55                  60
Met Leu Pro Gln Leu Val Cys Arg Leu Val
 65                  70
```

<210> SEQ ID NO 40
<211> LENGTH: 73
<212> TYPE: PRT
<213> ORGANISM: Homo sapiens

<400> SEQUENCE: 40

```
Phe Pro Ile Pro Leu Pro Tyr Cys Trp Leu Cys Arg Ala Leu Ile Lys
  1               5                  10                  15
Arg Ile Gln Ala Met Ile Pro Lys Gly Ala Leu Ala Val Ala Val Ala
                 20                  25                  30
Gln Val Cys Arg Val Val Pro Leu Val Ala Gly Gly Ile Cys Gln Cys
             35                  40                  45
Leu Ala Glu Arg Tyr Ser Val Ile Leu Leu Asp Thr Leu Leu Gly Arg
         50                  55                  60
Met Leu Pro Gln Leu Val Cys Arg Leu
 65                  70
```

<210> SEQ ID NO 41
<211> LENGTH: 72
<212> TYPE: PRT
<213> ORGANISM: Homo sapiens

<400> SEQUENCE: 41

```
Phe Pro Ile Pro Leu Pro Tyr Cys Trp Leu Cys Arg Ala Leu Ile Lys
  1               5                  10                  15
Arg Ile Gln Ala Met Ile Pro Lys Gly Ala Leu Ala Val Ala Val Ala
                 20                  25                  30
Gln Val Cys Arg Val Val Pro Leu Val Ala Gly Gly Ile Cys Gln Cys
             35                  40                  45
Leu Ala Glu Arg Tyr Ser Val Ile Leu Leu Asp Thr Leu Leu Gly Arg
         50                  55                  60
Met Leu Pro Gln Leu Val Cys Arg
 65                  70
```

<210> SEQ ID NO 42
<211> LENGTH: 71
<212> TYPE: PRT
<213> ORGANISM: Homo sapiens

<400> SEQUENCE: 42

```
Phe Pro Ile Pro Leu Pro Tyr Cys Trp Leu Cys Arg Ala Leu Ile Lys
  1               5                  10                  15
Arg Ile Gln Ala Met Ile Pro Lys Gly Ala Leu Ala Val Ala Val Ala
                 20                  25                  30
Gln Val Cys Arg Val Val Pro Leu Val Ala Gly Gly Ile Cys Gln Cys
             35                  40                  45
Leu Ala Glu Arg Tyr Ser Val Ile Leu Leu Asp Thr Leu Leu Gly Arg
         50                  55                  60
Met Leu Pro Gln Leu Val Cys
 65                  70
```

<210> SEQ ID NO 43
<211> LENGTH: 70
<212> TYPE: PRT
<213> ORGANISM: Homo sapiens

<400> SEQUENCE: 43

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val
65                  70

<210> SEQ ID NO 44
<211> LENGTH: 69
<212> TYPE: PRT
<213> ORGANISM: Homo sapiens

<400> SEQUENCE: 44

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu
65

<210> SEQ ID NO 45
<211> LENGTH: 68
<212> TYPE: PRT
<213> ORGANISM: Homo sapiens

<400> SEQUENCE: 45

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln
65

<210> SEQ ID NO 46
<211> LENGTH: 67
<212> TYPE: PRT
<213> ORGANISM: Homo sapiens

<400> SEQUENCE: 46

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys

```
                35                  40                  45
Leu Ala Glu Arg Tyr Ser Val Ile Leu Leu Asp Thr Leu Leu Gly Arg
 50                  55                  60
Met Leu Pro
 65

<210> SEQ ID NO 47
<211> LENGTH: 66
<212> TYPE: PRT
<213> ORGANISM: Homo sapiens

<400> SEQUENCE: 47

Phe Pro Ile Pro Leu Pro Tyr Cys Trp Leu Cys Arg Ala Leu Ile Lys
 1               5                  10                  15
Arg Ile Gln Ala Met Ile Pro Lys Gly Ala Leu Ala Val Ala Val Ala
                20                  25                  30
Gln Val Cys Arg Val Val Pro Leu Val Ala Gly Gly Ile Cys Gln Cys
                35                  40                  45
Leu Ala Glu Arg Tyr Ser Val Ile Leu Leu Asp Thr Leu Leu Gly Arg
 50                  55                  60
Met Leu
 65

<210> SEQ ID NO 48
<211> LENGTH: 65
<212> TYPE: PRT
<213> ORGANISM: Homo sapiens

<400> SEQUENCE: 48

Phe Pro Ile Pro Leu Pro Tyr Cys Trp Leu Cys Arg Ala Leu Ile Lys
 1               5                  10                  15
Arg Ile Gln Ala Met Ile Pro Lys Gly Ala Leu Ala Val Ala Val Ala
                20                  25                  30
Gln Val Cys Arg Val Val Pro Leu Val Ala Gly Gly Ile Cys Gln Cys
                35                  40                  45
Leu Ala Glu Arg Tyr Ser Val Ile Leu Leu Asp Thr Leu Leu Gly Arg
 50                  55                  60
Met
 65

<210> SEQ ID NO 49
<211> LENGTH: 64
<212> TYPE: PRT
<213> ORGANISM: Homo sapiens

<400> SEQUENCE: 49

Phe Pro Ile Pro Leu Pro Tyr Cys Trp Leu Cys Arg Ala Leu Ile Lys
 1               5                  10                  15
Arg Ile Gln Ala Met Ile Pro Lys Gly Ala Leu Ala Val Ala Val Ala
                20                  25                  30
Gln Val Cys Arg Val Val Pro Leu Val Ala Gly Gly Ile Cys Gln Cys
                35                  40                  45
Leu Ala Glu Arg Tyr Ser Val Ile Leu Leu Asp Thr Leu Leu Gly Arg
 50                  55                  60

<210> SEQ ID NO 50
<211> LENGTH: 63
<212> TYPE: PRT
<213> ORGANISM: Homo sapiens
```

<400> SEQUENCE: 50

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly
    50                  55                  60

<210> SEQ ID NO 51
<211> LENGTH: 62
<212> TYPE: PRT
<213> ORGANISM: Homo sapiens

<400> SEQUENCE: 51

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu
    50                  55                  60

<210> SEQ ID NO 52
<211> LENGTH: 61
<212> TYPE: PRT
<213> ORGANISM: Homo sapiens

<400> SEQUENCE: 52

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu
    50                  55                  60

<210> SEQ ID NO 53
<211> LENGTH: 60
<212> TYPE: PRT
<213> ORGANISM: Homo sapiens

<400> SEQUENCE: 53

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr
    50                  55                  60

<210> SEQ ID NO 54
<211> LENGTH: 59
<212> TYPE: PRT

<213> ORGANISM: Homo sapiens

<400> SEQUENCE: 54

Phe Pro Ile Pro Leu Pro Tyr Cys Trp Leu Cys Arg Ala Leu Ile Lys
1               5                   10                  15
Arg Ile Gln Ala Met Ile Pro Lys Gly Ala Leu Ala Val Ala Val Ala
            20                  25                  30
Gln Val Cys Arg Val Val Pro Leu Val Ala Gly Gly Ile Cys Gln Cys
        35                  40                  45
Leu Ala Glu Arg Tyr Ser Val Ile Leu Leu Asp
    50                  55

<210> SEQ ID NO 55
<211> LENGTH: 58
<212> TYPE: PRT
<213> ORGANISM: Homo sapiens

<400> SEQUENCE: 55

Phe Pro Ile Pro Leu Pro Tyr Cys Trp Leu Cys Arg Ala Leu Ile Lys
1               5                   10                  15
Arg Ile Gln Ala Met Ile Pro Lys Gly Ala Leu Ala Val Ala Val Ala
            20                  25                  30
Gln Val Cys Arg Val Val Pro Leu Val Ala Gly Gly Ile Cys Gln Cys
        35                  40                  45
Leu Ala Glu Arg Tyr Ser Val Ile Leu Leu
    50                  55

<210> SEQ ID NO 56
<211> LENGTH: 57
<212> TYPE: PRT
<213> ORGANISM: Homo sapiens

<400> SEQUENCE: 56

Phe Pro Ile Pro Leu Pro Tyr Cys Trp Leu Cys Arg Ala Leu Ile Lys
1               5                   10                  15
Arg Ile Gln Ala Met Ile Pro Lys Gly Ala Leu Ala Val Ala Val Ala
            20                  25                  30
Gln Val Cys Arg Val Val Pro Leu Val Ala Gly Gly Ile Cys Gln Cys
        35                  40                  45
Leu Ala Glu Arg Tyr Ser Val Ile Leu
    50                  55

<210> SEQ ID NO 57
<211> LENGTH: 56
<212> TYPE: PRT
<213> ORGANISM: Homo sapiens

<400> SEQUENCE: 57

Phe Pro Ile Pro Leu Pro Tyr Cys Trp Leu Cys Arg Ala Leu Ile Lys
1               5                   10                  15
Arg Ile Gln Ala Met Ile Pro Lys Gly Ala Leu Ala Val Ala Val Ala
            20                  25                  30
Gln Val Cys Arg Val Val Pro Leu Val Ala Gly Gly Ile Cys Gln Cys
        35                  40                  45
Leu Ala Glu Arg Tyr Ser Val Ile
    50                  55

<210> SEQ ID NO 58
<211> LENGTH: 55

```
<212> TYPE: PRT
<213> ORGANISM: Homo sapiens

<400> SEQUENCE: 58

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val
    50                  55

<210> SEQ ID NO 59
<211> LENGTH: 54
<212> TYPE: PRT
<213> ORGANISM: Homo sapiens

<400> SEQUENCE: 59

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser
    50

<210> SEQ ID NO 60
<211> LENGTH: 53
<212> TYPE: PRT
<213> ORGANISM: Homo sapiens

<400> SEQUENCE: 60

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr
    50

<210> SEQ ID NO 61
<211> LENGTH: 52
<212> TYPE: PRT
<213> ORGANISM: Homo sapiens

<400> SEQUENCE: 61

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg
    50

<210> SEQ ID NO 62
```

<211> LENGTH: 51
<212> TYPE: PRT
<213> ORGANISM: Homo sapiens

<400> SEQUENCE: 62

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu
    50

<210> SEQ ID NO 63
<211> LENGTH: 50
<212> TYPE: PRT
<213> ORGANISM: Homo sapiens

<400> SEQUENCE: 63

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala
    50

<210> SEQ ID NO 64
<211> LENGTH: 49
<212> TYPE: PRT
<213> ORGANISM: Homo sapiens

<400> SEQUENCE: 64

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu

<210> SEQ ID NO 65
<211> LENGTH: 48
<212> TYPE: PRT
<213> ORGANISM: Homo sapiens

<400> SEQUENCE: 65

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

<210> SEQ ID NO 66
<211> LENGTH: 47
<212> TYPE: PRT
<213> ORGANISM: Homo sapiens

```
<400> SEQUENCE: 66

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln
        35                  40                  45

<210> SEQ ID NO 67
<211> LENGTH: 46
<212> TYPE: PRT
<213> ORGANISM: Homo sapiens

<400> SEQUENCE: 67

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys
        35                  40                  45

<210> SEQ ID NO 68
<211> LENGTH: 45
<212> TYPE: PRT
<213> ORGANISM: Homo sapiens

<400> SEQUENCE: 68

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile
        35                  40                  45

<210> SEQ ID NO 69
<211> LENGTH: 44
<212> TYPE: PRT
<213> ORGANISM: Homo sapiens

<400> SEQUENCE: 69

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly
        35                  40

<210> SEQ ID NO 70
<211> LENGTH: 43
<212> TYPE: PRT
<213> ORGANISM: Homo sapiens

<400> SEQUENCE: 70

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly
        35                  40
```

```
<210> SEQ ID NO 71
<211> LENGTH: 42
<212> TYPE: PRT
<213> ORGANISM: Homo sapiens

<400> SEQUENCE: 71

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala
        35                  40

<210> SEQ ID NO 72
<211> LENGTH: 41
<212> TYPE: PRT
<213> ORGANISM: Homo sapiens

<400> SEQUENCE: 72

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val
        35                  40

<210> SEQ ID NO 73
<211> LENGTH: 40
<212> TYPE: PRT
<213> ORGANISM: Homo sapiens

<400> SEQUENCE: 73

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu
        35                  40

<210> SEQ ID NO 74
<211> LENGTH: 39
<212> TYPE: PRT
<213> ORGANISM: Homo sapiens

<400> SEQUENCE: 74

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro
        35

<210> SEQ ID NO 75
<211> LENGTH: 38
<212> TYPE: PRT
<213> ORGANISM: Homo sapiens

<400> SEQUENCE: 75

Phe Pro Ile Pro Leu Pro Tyr Cys Trp Leu Cys Arg Ala Leu Ile Lys
1               5                   10                  15
```

Arg Ile Gln Ala Met Ile Pro Lys Gly Ala Leu Ala Val Ala Val Ala
            20                  25                  30

Gln Val Cys Arg Val Val
        35

<210> SEQ ID NO 76
<211> LENGTH: 37
<212> TYPE: PRT
<213> ORGANISM: Homo sapiens

<400> SEQUENCE: 76

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val
        35

<210> SEQ ID NO 77
<211> LENGTH: 36
<212> TYPE: PRT
<213> ORGANISM: Homo sapiens

<400> SEQUENCE: 77

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg
        35

<210> SEQ ID NO 78
<211> LENGTH: 35
<212> TYPE: PRT
<213> ORGANISM: Homo sapiens

<400> SEQUENCE: 78

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys
        35

<210> SEQ ID NO 79
<211> LENGTH: 34
<212> TYPE: PRT
<213> ORGANISM: Homo sapiens

<400> SEQUENCE: 79

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val

<210> SEQ ID NO 80
<211> LENGTH: 33
<212> TYPE: PRT
<213> ORGANISM: Homo sapiens

<400> SEQUENCE: 80

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln

<210> SEQ ID NO 81
<211> LENGTH: 32
<212> TYPE: PRT
<213> ORGANISM: Homo sapiens

<400> SEQUENCE: 81

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

<210> SEQ ID NO 82
<211> LENGTH: 31
<212> TYPE: PRT
<213> ORGANISM: Homo sapiens

<400> SEQUENCE: 82

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val
            20                  25                  30

<210> SEQ ID NO 83
<211> LENGTH: 30
<212> TYPE: PRT
<213> ORGANISM: Homo sapiens

<400> SEQUENCE: 83

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala
            20                  25                  30

<210> SEQ ID NO 84
<211> LENGTH: 29
<212> TYPE: PRT
<213> ORGANISM: Homo sapiens

<400> SEQUENCE: 84

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val
            20                  25

<210> SEQ ID NO 85
<211> LENGTH: 28
<212> TYPE: PRT
<213> ORGANISM: Homo sapiens

<400> SEQUENCE: 85

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala

```
                20                  25

<210> SEQ ID NO 86
<211> LENGTH: 27
<212> TYPE: PRT
<213> ORGANISM: Homo sapiens

<400> SEQUENCE: 86

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu
                20                  25

<210> SEQ ID NO 87
<211> LENGTH: 26
<212> TYPE: PRT
<213> ORGANISM: Homo sapiens

<400> SEQUENCE: 87

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala
                20                  25

<210> SEQ ID NO 88
<211> LENGTH: 25
<212> TYPE: PRT
<213> ORGANISM: Homo sapiens

<400> SEQUENCE: 88

Phe Pro Ile Pro Leu Pro Tyr Cys Trp Leu Cys Arg Ala Leu Ile Lys
1               5                   10                  15

Arg Ile Gln Ala Met Ile Pro Lys Gly
                20                  25

<210> SEQ ID NO 89
<211> LENGTH: 24
<212> TYPE: PRT
<213> ORGANISM: Homo sapiens

<400> SEQUENCE: 89

Phe Pro Ile Pro Leu Pro Tyr Cys Trp Leu Cys Arg Ala Leu Ile Lys
1               5                   10                  15

Arg Ile Gln Ala Met Ile Pro Lys
                20

<210> SEQ ID NO 90
<211> LENGTH: 23
<212> TYPE: PRT
<213> ORGANISM: Homo sapiens

<400> SEQUENCE: 90

Phe Pro Ile Pro Leu Pro Tyr Cys Trp Leu Cys Arg Ala Leu Ile Lys
1               5                   10                  15

Arg Ile Gln Ala Met Ile Pro
                20

<210> SEQ ID NO 91
<211> LENGTH: 22
<212> TYPE: PRT
<213> ORGANISM: Homo sapiens

<400> SEQUENCE: 91
```

Phe Pro Ile Pro Leu Pro Tyr Cys Trp Leu Cys Arg Ala Leu Ile Lys
1               5                   10                  15

Arg Ile Gln Ala Met Ile
            20

<210> SEQ ID NO 92
<211> LENGTH: 21
<212> TYPE: PRT
<213> ORGANISM: Homo sapiens

<400> SEQUENCE: 92

Phe Pro Ile Pro Leu Pro Tyr Cys Trp Leu Cys Arg Ala Leu Ile Lys
1               5                   10                  15

Arg Ile Gln Ala Met
            20

<210> SEQ ID NO 93
<211> LENGTH: 20
<212> TYPE: PRT
<213> ORGANISM: Homo sapiens

<400> SEQUENCE: 93

Phe Pro Ile Pro Leu Pro Tyr Cys Trp Leu Cys Arg Ala Leu Ile Lys
1               5                   10                  15

Arg Ile Gln Ala
            20

<210> SEQ ID NO 94
<211> LENGTH: 21
<212> TYPE: PRT
<213> ORGANISM: Artificial sequence
<220> FEATURE:
<223> OTHER INFORMATION: Synthetic peptide

<400> SEQUENCE: 94

Lys Leu Leu Leu Leu Lys Leu Leu Leu Lys Leu Leu Leu Leu Lys
1               5                   10                  15

Leu Leu Leu Leu Lys
            20

<210> SEQ ID NO 95
<211> LENGTH: 13
<212> TYPE: PRT
<213> ORGANISM: Artificial Sequence
<220> FEATURE:
<223> OTHER INFORMATION: Synthetic peptide

<400> SEQUENCE: 95

Gly Gly Ser Gly Gly Ser Gly Gly Gly Ser Gly Ser
1               5                   10

<210> SEQ ID NO 96
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: This sequence may encompass 1, 2, or 3
      'Gly-Gly-Gly-Gly-Ser' repeating units

<400> SEQUENCE: 96

-continued

```
Gly Gly Gly Gly Ser
1               5
```

METHODS AND COMPOSITIONS FOR DELIVERY OF MEDICAMENTS TO THE LUNGS

CROSS-REFERENCE TO RELATED APPLICATIONS

This application is the national stage of International (PCT) Patent Application Serial No. PCT/US2009/067499, filed Dec. 10, 2009, which claims the benefit of and priority to U.S. provisional patent application Ser. No. 61/121,405, filed Dec. 10, 2008; the entire contents of each application are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 17, 2014, is named GUA-002_SL.txt and is 98,304 bytes in size.

BACKGROUND OF INVENTION

In pulmonary disorders including chronic obstructive pulmonary disease (COPD), chronic bronchitis, and emphysema, there is a chronic obstruction of air flow in and out of the lungs. The obstruction that manifests in these disorders is often permanent and progresses over time. Exacerbations, which are an acute worsening of respiratory function, result in increased morbidity and mortality.

Over the last few decades, research to treat chronic pulmonary disorders such as COPD has focused on identifying inhibitors of human neutrophil elastase (HNE). HNE is a protease capable of degrading numerous proteins including the structural proteins fibronectin, collagen, and elastin. When aberrantly expressed, HNE is one of the most destructive enzymes in the body. HNE is associated with tissue destruction and inflammation and is implicated in numerous pulmonary diseases including COPD, cystic fibrosis, and acute respiratory distress syndrome (ARDS) as well as other diseases of the body. However, the development of HNE inhibitors has been difficult and despite decades of research only one HNE treatment is currently on the market with approval for use only in Japan.

The development of HNE inhibitors and other drugs designed for lung treatment has focused on systemic treatments. A major obstacle with such an approach, whether the drug is delivered orally, parenterally, or by inhalation, is achieving meaningful residence times in the lungs. Thus, there remains an unmet need for effective lung treatments.

SUMMARY OF THE INVENTION

The disclosure provides methods and compositions for delivering medicaments to the lungs. It is now appreciated that a key problem associated with treating lung diseases is the difficulty in obtaining sufficient residence times of active drug molecules in the lungs. The lungs are very adept at clearing foreign matter, such that active drug molecules may be cleared from the lung before the desired medicinal effect is achieved.

Pulmonary surfactants are secreted by Type II pneumocytes in the lungs to reduce surface tension within the alveoli therefore preventing alveolar collapse during expiration. Pulmonary surfactants, which are a complex of lipids and proteins, spread across the alveolar surface to lower surface tension and are maintained in the lung for extended periods. Therefore, the residence time of active drug molecules in the lung can be increased by covalently linking the active drug molecule to a surfactant lipid or protein. Administering active drug molecules covalently linked to a surfactant lipid or protein provides increased duration of action in the lung resulting in substantially fewer doses and better patient compliance, localization of the active drug molecule to the lung resulting in decreased in systemic toxicity, and significantly higher localized lung concentrations for enhanced efficacy.

In one aspect, the invention provides a drug composition, formulated for inhalation, comprising a surface active agent that has an affinity for the human alveolar/gas interface. The surface active agent comprises at least a portion of a mammalian lung surfactant polypeptide or mimic thereof that is substantially non-immunogenic to humans.

The surface active agent is associated with a pulmonary active drug, and preferably covalently bonded to the drug, which binds to an extracellular or cell-surface target or other target accessible to the pulmonary/gas interface. The extracellular or cell-surface target may be, by way of example, an elastase, a TNF receptor, an EGF receptor, an adrenergic receptor, a P2X or P2Y purinergic receptor, or an endothelin receptor. In certain embodiments, the surface active agent covalently bonded to a pulmonary active drug, which binds to an extracellular or cell surface target is administered to a subject suffering from lung disease, including, but not limited to emphysema, chronic bronchitis and acute exacerbation of chronic bronchitis (AECB), chronic obstructive pulmonary disease (COPD), asthma, respiratory distress disorder (RDS), pneumonia (including ventilator associated pneumonia (VAP)), tuberculosis or other bacterial infection, cystic fibrosis, pulmonary arterial hypertension (PAH), and lung cancer.

For example, the intracellular parasite responsible for tuberculosis (TB) is harbored in macrophages. Macrophages normally have a short life ingesting foreign organisms and undergo apoptosis to remove foreign organisms from the body. The TB microorganism corrupts the intracellular suicide communications leaving macrophages essentially immortal, thus permitting the mycoplasm to persist. A signature of immortalized macrophages harboring tuberculosis is the overexpression of P2X purinergic receptor (e.g., P2X7 purinergic receptor) on the macrophage membrane (Placido et al., *Cell Immunol*. 244:10-8 (2006)). P2X receptor agonists, such as ATP and ATP analogues, will induce apoptosis in these macrophages and thus kill the parasitic TB (Pfeiffer et al., *J. Leukoc. Biol*. 75:1173 (2004)). Also see, for example: Mokrousov et al., "*Mycobacterium Tuberculosis* Coexistence with Humans-making an imprint on the macrophage P2X7 gene?," *J. Medical Microbiology*, 2008, 57, 581. Benzoyl derivatives of ATP are potent extracellular agonists of P2X receptors (e.g., P2X7 purinergic receptors) and can be covalently linked to the surface active agent and delivered via inhalation as a long duration TB treatment.

ATP and ATP analogues may also be used to agonize P2Y receptors implicated in cystic fibrosis. Cystic fibrosis is a recessive genetic disorder caused by a mutation in the cystic fibrosis transmembrane regulator (CFTR) gene, which encodes a chloride channel. The defective chloride channel results in aberrant ion transport which leads to a reduced mucosal hydration and mucus clearing and ultimately chronic infection of the respiratory tract. P2Y receptors (e.g., P2Y$_2$ receptor) are expressed on the luminal surface of epithelial cells lining bronchial and lung surfaces. P2Y agonists stimulate chloride secretion, inhibit sodium absorption and enhance airway clearance (Deterding et al., *Am. J. Respira-*

*tory & Crit. Care Med.*, 176:362-369 (2007)). Daily administration of an ATP analogue agonizing P2Y receptors provides positive results, but only for a short period of time as systemic side effects arise after a few months of treatment. Covalent linkage of P2Y receptor agonists, such as ATP, ATP analogues, and denufosol tetrasodium, to a surface active agent will increase the residence time of the P2Y agonist in the lungs and reduce the systemic side effects associated with increased levels of ATP in the bloodstream.

Agonists for the β2-adrenergic receptor are well-established bronchodilators for the treatment of asthma (Anderson, Clin. Rev. Allergy Immunol. 31:119-30 (2006). The β2-adrenergic receptor, however, is ubiquitously expressed and thus repeated dosing will likely have deleterious systemic side effects. Covalently linking a β2-adrenergic receptor agonist, for example, albuterol, to a surface active peptide will essentially isolate the active agent to the lung, thus avoiding or diminishing the potential systemic toxicities.

Steriods are also well-established treatments for asthma. The corticosteroid, fluticasone proprionate, is frequently used to treat asthma, but in cases of severe asthma attacks prednisolone is typically more effective. Prednisolone, however, can only be used for a short period of time (e.g., 3-4 days or 2-3 weeks depending on the severity of the asthma attack) due to serious side effects that preclude its chronic use. Covalently linking a steroid, for example, prednisolone, to a surface active agent will increase the residence time of the steroid in the lung converting its use from an acute treatment to a chronic treatment.

Endothelin receptor antagonism is an important therapeutic strategy in PAH, which is an increase in blood pressure in the pulmonary arteries (Leuchte et al., Am. J. Physiol. Lung Cell Mol. Physiol., 2008, 294, L772-L776). PAH is characterized by vasoconstriction and abnormal proliferation of the pulmonary smooth muscle cells. Endothelin receptors A and B are expressed on pulmonary smooth muscle cells and mediate the mitogenic and vasoconstrictive effects of endothlin. Endothlin receptor antagonists, such as bosentan and sitaxentan, induce vasodilation, block the abnormal proliferation of smooth muscle cells, and have been shown to improve the pulmonary hemodynamics of patients with PAH. However, administration of endothlin receptor antagonists also results in serious side effects such as hepatocellular injury. Covalently linking an endothlin receptor antagonist, for example, bosentan, to a surface active agent will isolate the active agent in the lung thus reducing systemic toxicities. Other drugs used in the treatment of PAH include prostacyclin analogues and phosphodiesterase type 5 (PDE5) inhibitors. In particular, most prostacyclin analogues, for example, epoprostenol, are administered by continuous infusion or by injection, which can be painful and dangerous. Covalently linking a prostacyclin analogue to a surface active agent coupled with inhalation delivery will have the advantage of selective deposition in the lungs with less systemic side effects and potentially better patient compliance.

The epidermal growth factor receptor (EGFR) has been validated as an anticancer target (Carney, Expert Rev. Mol. Diagn. 7:309-19 (2007)) with products such as herceptin on the market to treat breast cancer. Inhibiting the activation of EGFR is a potential treatment for nonsmall cell lung cancer (Y. H. Ling et al., *Molecular Pharmacology* 72:248-58 (2007)). One hurdle in targeting the EGFR family (which includes HER1, HER2, HER3, and HER4) is that when one receptor is inactivated that the other receptors compensate for the inactivated receptor. In addition, there are eleven known endogenous ligands for the EGFR family. Matrix metalloproteinase (e.g., ADAM10 and ADAM17, also known as shed-dases) have been shown to release endogenous ligands of EGFR via a cell surface shedding mechanism (Horiuchi et al., *Mol. Biol. Cell* 18:176-188 (2007); Gazdar & Minna, *Cancer Prev Res*, 1(3):156-160 (2008); Zhou et al., *Cancer Cell*, 10:39-50 (2006)). Non-selective inhibitors of matrix metalloproteinase enzymes have been identified, however, ubiquitous inhibition of this enzyme class will likely have deleterious systemic side effects. Covalently linking a non-selective inhibitor of matrix metalloproteinase (e.g., marimastat) to a surface active agent will isolate the active agent to the lungs and deactivate all four EGFR pathways in the lungs.

These examples including emphysema, tuberculosis, cystic fibrosis, asthma, pulmonary arterial hypertension (PAH), and nonsmall cell lung cancer demonstrate the generality of covalently linking therapeutic molecules to agents that preferentially reside in the lung with inhalation delivery.

In another embodiment, the surface active agent is covalently bonded to a pulmonary active drug and a cell membrane permeable transport molecule that enters the lung cells. Agents that function within the cell include, but are not limited to retinoids, survivin inhibitors, and caspase promoters.

In another embodiment, the surface active agent comprises a human lung surfactant or a non-human mammalian lung surfactant or a fraction thereof. Exemplary non-human mammalian lung surfactants include bovine, porcine, or ovine lung surfactants or a fraction thereof. The agent may comprise or be derived from a mammalian lung surfactant harvested from the lungs of a human or non-human mammal.

In another embodiment, the surface active agent comprises at least a portion of a mammalian lung surfactant polypeptide, an allelic variant thereof, or a synthetic mimic thereof. The agent may comprise a natural surfactant polypeptide, such as SP-A, SP-B, SP-C, SP-D, portions thereof, or mixtures thereof. The agent may comprise a mixture of SP-A, SP-B, SP-C, SP-D or portions thereof. Exemplary peptides include at least about a 5, 10, 15, 20, 25, 30, 35, 40, 45, or 50 amino acid fragment of a natural surfactant polypeptide. The surface active agent may comprise at least a portion of SP-B. Exemplary SP-B polypeptides include at least about a 5, 10, 15, 20, 25, 30, 35, 40, 45, or 50 amino acid fragment of SP-B. An SP-B peptide may be an amino-terminal peptide or a carboxy-terminal peptide. An exemplary SP-B peptide may be a 25-amino acid amino terminal peptide.

In another embodiment, the surface active agent comprises a synthetically produced peptide. A peptidomimetic may comprise at least one deletion or amino acid substitution mutant of a mammalian lung surfactant polypeptide. A peptidomimetic may comprise at least one deletion or amino acid substitution mutant of a human lung surfactant polypeptide.

In another embodiment, the surface active agent may comprise a surfactant polypeptide that is recombinantly produced. A recombinant mammalian lung surfactant polypeptide, such as SP-A, SP-B, SP-C, SP-D, or a portion thereof may be produced by expressing the DNA coding for SP-A, SP-B, SP-C, SP-D, or a portion thereof in a prokaryotic or eukaryotic expression system. Recombinant surfactant polypeptides may be the same or differ from mammalian lung surfactant polypeptides. A recombinant polypeptide may comprise at least one deletion or amino acid substitution mutant of a mammalian, preferably a human lung surfactant polypeptide.

In another embodiment, the surface active agent comprises both a surfactant polypeptide and a lipid.

The surface active agent preferably is covalently bonded to a pulmonary active drug. The pulmonary active drug may be covalently linked to a surfactant protein or lipid. The pulmonary active drug may be covalently bonded to an amino- or carboxy-terminal amino acid or an internal amino acid of a surfactant polypeptide. In certain embodiments, more than one pulmonary active drug is bound to a surface active agent. In other embodiments, a single pulmonary active drug is bound to a surface active agent and mixed with at least one other pulmonary active drug bound to a surface active agent.

In one embodiment, the a pulmonary active drug molecule is extended with an amino acid or mimetic linker, such as a glycine linker, to create an unnatural amino acid that can be used in automatic peptide synthesis. The extended molecule (i.e., the drug plus the amino acid linker) can then be attached to the surface active agent through an amino- or hydroxyl-group.

The pulmonary active drug binds to an extracellular or cell-surface bound target that is accessible to the pulmonary/gas interface. Generally, the pulmonary active drug portion of the conjugate may be any drug that has utility in the management or treatment of lung disease and, preferably are those characterized by a molecular weight below about 10,000 KD. Such small molecule drugs, as opposed to high molecular weight biologics, are particularly well-suited for delivery by inhalation in accordance with the teachings of this invention. Indeed, many drug moieties having a molecular weight below about 5,000 KD, or about 2000 KD may be used. In certain embodiments, the pulmonary active drug may be an elastase inhibitor, corticosteroid, bronchodilator, antihistamine, antibiotic, P2X agonist, P2Y agonist, chemotherapeutic agent, matrix metalloproteinase inhibitor, ADAM inhibitor, kinase inhibitor, endothelin receptor antagonist, prostacyclin analogue, or phosphodiesterase type 5 inhibitor.

In other embodiments, the pulmonary active drug may be a polypeptide such as an antibody (e.g., an intact antibody, an antigen binding fragment such as a Fab, Fab', $(Fab')_2$, Fv fragment, or a biosynthetic antibody such as a single Fv or SFv molecule) directed against any targets disclosed herein or addressed by the drugs disclosed herein, a fusion protein or a peptidomimetic.

In certain embodiments, more than one pulmonary active drug may be covalently bonded to a surface active agent and administered in combination. When more than one pulmonary active drug is covalently bonded to a surface active agent, the drug may be the same drug, a member of the same drug class, or a member of a different drug class.

The drug composition is delivered to the lungs of a human patient by an inhalation device. Exemplary inhalation devices include fixed dose inhalers, metered dose inhalers, and nebulizers.

In one embodiment, the invention provides a drug composition formulated for inhalation. The drug composition comprises a surface active agent characterized by an affinity for the human alveolar/gas interface, wherein the surface active agent comprises at least a portion of a mammalian lung surfactant polypeptide or a mimic thereof, and covalently bonded to said agent is a pulmonary active drug which binds to an extracellular or cell surface-bound target accessible to the pulmonary/gas interface. The pulmonary active drug may be an antihistamine, a P2Y agonist, a matrix metalloproteinase inhibitor, an ADAM inhibitor, a kinase inhibitor, an endothelin receptor antagonist, a prostacyclin analogue, and a phophodiesterase type 5 inhibitor.

In another aspect, the invention provides a method for treating a subject suffering from or at risk of a lung disease. The method comprises administering a conjugate comprising a pulmonary active drug covalently bonded to a surface active agent characterized by an affinity for the human alveolar/gas interface, wherein the surface active agent comprises at least a portion of a mammalian lung surfactant polypeptide or a mimic thereof that is substantially non-immunogenic to humans. The conjugate is administered to the subject by inhalation in an amount effective to induce a drug effect in the lungs.

The method of administration targets the pulmonary active drug to the lungs of a subject in need thereof. The modified compositions of matter and the methods of administration have the dual advantage that they reduce the systemic bioavailability and distribution of the pulmonary active drug relative to inhalation administration of an unconjugated drug, and this provides an advantage in dealing with off target toxicities. The modified compositions of matter and the methods of administration also increase the residence time of the drug in the lung relative to inhalation administration of an unconjugated drug, and therefore very significantly improve lung bioavailability. The result can be a reformulation or redesign of a drug that has unacceptable toxicity and/or poor efficacy, even though it binds and inhibits the target well to produce a clinically valuable modified drug.

The method of administration targets the pulmonary active drug to the lungs of a subject in need thereof. The method of administration reduces the systemic bioavailability of the drug relative to inhalation administration of an unconjugated drug. The method of administration increases the residence time of the drug in the lung relative to inhalation administration of an unconjugated drug.

In one embodiment, the administration of a pulmonary active drug-surface active agent conjugate reduces the dosing frequency relative to administration of an unconjugated drug. The administration step may be repeated once daily, every other day, every three days, every four days, every five days, biweekly, or weekly. The administration step may be conducted using an inhaler, an aerosol, particulates with or without propellants, metered dosages, or a nebulizer.

In certain embodiments, the subject in need of treatment is suffering from lung inflammation or disease or is at risk of suffering from a lung disease. The subject in need of treatment may be suffering from emphysema, chronic bronchitis and acute exacerbation of chronic bronchitis (AECB), chronic obstructive pulmonary disease (COPD), asthma, respiratory distress disorder (RDS), pneumonia (including ventilator associated pneumonia (VAP)), tuberculosis or other bacterial infection, cystic fibrosis, pulmonary arterial hypertension (PAH), and/or lung cancer.

BRIEF DESCRIPTION OF THE DRAWINGS

FIG. 1A shows the nucleic acid sequence that encodes human surfactant protein A (SEQ ID NO: 1). FIG. 1B shows the amino acid sequence for human surfactant protein A (SEQ ID NO: 2).

FIG. 2A shows the nucleic acid sequence that encodes human surfactant protein B (SEQ ID NO: 3). FIG. 2B shows the amino acid sequence for human surfactant protein B (SEQ ID NO: 4). FIG. 2C shows the amino acid sequence for mature human surfactant protein B (SEQ ID NO: 5).

FIG. 3A shows the nucleic acid sequence that encodes human surfactant protein C (SEQ ID NO: 6). FIG. 3B shows the amino acid sequence for human surfactant protein C (SEQ ID NO: 7). FIG. 3C shows the amino acid sequence for mature human surfactant protein C (SEQ ID NO: 8).

FIG. 4A shows the nucleic acid sequence that encodes human surfactant protein D (SEQ ID NO: 9). FIG. 4B shows the amino acid sequence for human surfactant protein D (SEQ ID NO: 10). FIG. 4C shows the amino acid sequence for mature human surfactant protein D (SEQ ID NO: 11).

FIG. 5A shows the nucleic acid sequence that encodes bovine surfactant protein A (SEQ ID NO: 12). FIG. 5B shows the amino acid sequence for bovine surfactant protein A (SEQ ID NO: 13).

FIG. 6A shows the nucleic acid sequence that encodes bovine surfactant protein B (SEQ ID NO: 14). FIG. 6B shows the amino acid sequence for bovine surfactant protein B (SEQ ID NO: 15).

FIG. 7A shows the nucleic acid sequence that encodes bovine surfactant protein C (SEQ ID NO: 16). FIG. 7B shows the amino acid sequence for bovine surfactant protein C (SEQ ID NO: 17).

FIG. 8A shows the nucleic acid sequence that encodes bovine surfactant protein D (SEQ ID NO: 18). FIG. 8B shows the amino acid sequence for bovine surfactant protein D (SEQ ID NO: 19).

FIG. 9A shows the nucleic acid sequence that encodes porcine surfactant protein A (SEQ ID NO: 20). FIG. 9B shows the amino acid sequence for porcine surfactant protein A (SEQ ID NO: 21).

FIG. 10A shows the nucleic acid sequence that encodes a partial porcine surfactant protein B (SEQ ID NO: 22). FIG. 10B shows a partial amino acid sequence for porcine surfactant protein B (SEQ ID NO: 23).

FIG. 11A shows the nucleic acid sequence that encodes porcine surfactant protein C (SEQ ID NO: 24). FIG. 11B shows the amino acid sequence for porcine surfactant protein C (SEQ ID NO: 25).

FIG. 12A shows the nucleic acid sequence that encodes porcine surfactant protein D (SEQ ID NO: 26). FIG. 12B shows the amino acid sequence for porcine surfactant protein D (SEQ ID NO: 27).

FIG. 13A shows the nucleic acid sequence that encodes ovine surfactant protein A (SEQ ID NO: 28). FIG. 13B shows the amino acid sequence for ovine surfactant protein A (SEQ ID NO: 29).

FIG. 14A shows the nucleic acid sequence that encodes ovine surfactant protein B (SEQ ID NO: 30). FIG. 14B shows the amino acid sequence for ovine surfactant protein B (SEQ ID NO: 31).

FIG. 15A shows the nucleic acid sequence that encodes ovine surfactant protein C (SEQ ID NO: 32). FIG. 15B shows the amino acid sequence for ovine surfactant protein C (SEQ ID NO: 33).

FIG. 16A shows the nucleic acid sequence that encodes a partial ovine surfactant protein D (SEQ ID NO: 34). FIG. 16B shows a partial amino acid sequence for ovine surfactant protein D (SEQ ID NO: 35).

FIG. 17 is a table depicting exemplary human neutrophil elastase (HNE) inhibitors. The reference numbers listed in the table correspond to the compound identifiers referred to in Philip D. Edwards and Peter R. Bernstein in "Synthetic Inhibitors of Elastase," Medicinal Research Reviews, Vol. 14, No. 2, 127-194 (1994).

Figure 18:
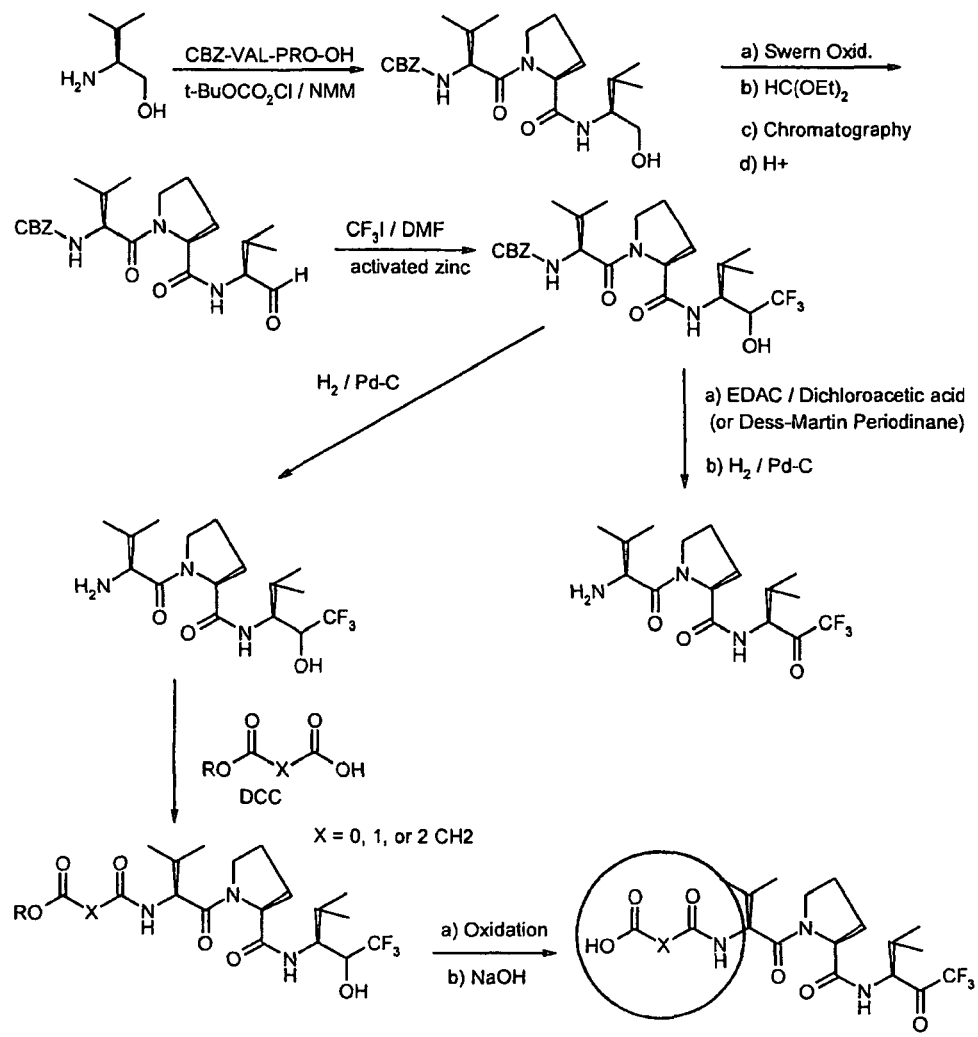

FIG. 18 is a schematic diagram depicting the chemical synthesis of a representative emphysema inhibitor. The emphysema inhibitor as shown contains a glycine linker. The glycine linker (circled) converts the compound to an unnatural amino acid that may be used in a standard peptide synthesis reaction for covalent coupling to the N-terminal 1-25 amino acids of SP-B.

FIG. 19 is a table depicting exemplary targets for use as HNE inhibitors. Target 2 attached to the N-terminus of the first 25 residues of the human surfactant B peptide forms target C. Similarly, target 3 attached to the N-terminus of the first 25 residues of the human surfactant B peptide forms target B.

FIG. 20 is a schematic diagram depicting the chemical structures of antihistamine drugs. Circled side chains depict exemplary positions where a lung surfactant moiety may be linked.

FIG. 21 is a schematic diagram depicting the chemical structure of marimastat, a nonselective matrix metalloproteinase inhibitor, derivatized with glycine linker.

FIG. 22 provides photographs (A-D) of lung histology sections from four mice with HNE induced emphysema.

FIG. 23 shows photographs (A-D) of lung histology sections from four mice with HNE induced emphysema treated with a Zeneca inhibitor (target 2).

FIG. 24 shows photographs (A-D) of lung histology sections from four mice from four mice instilled with saline.

FIG. 25 shows photographs (A-D) of lung histology sections from four mice with HNE induced emphysema treated with a Zeneca HNE inhibitor linked to a lung surfactant B peptide (target C).

DETAILED DESCRIPTION OF THE INVENTION

Surfactant Proteins

The surface active agent comprises at least a portion of a mammalian lung surfactant polypeptide that is substantially non-immunogenic to humans. The polypeptide or portion thereof may be a mammalian lung surfactant moiety or a synthetic mimic thereof. Exemplary surfactant polypeptides may be animal-derived, recombinant, synthetic, analogs, or peptide mimetics.

Natural lung surfactant proteins include SP-A, SP-B, SP-C, SP-D, or portions thereof, alone or in combination with lipids (U.S. Pat. No. 5,302,581). In some embodiments, the surface active agent comprises the full length surfactant polypeptide. In other embodiments, the surface active agent comprises a portion of a surfactant polypeptide. For example, human SP-B is a 79 amino acid residue polypeptide, however, the N-terminal 25 amino acid residues of SP-B possess therapeutic effects comparable to the whole peptide (Kurutz and Lee, Biochem., 41, 9627-36 (2002)). Exemplary peptides of natural lung surfactant proteins may be at least about 5, 10, 15, 20, 25, 30, 35, 40, 45, or 50 amino acids in length. Exemplary peptides of human SP-B are shown in Table 1.

In one embodiment, the surface active agent comprises human lung surfactant obtained by lung lavage of human cadavers at autopsy or by lung lavage of consenting adults.

In certain embodiments, the surface active agent comprises a non-human mammalian lung surfactant or a fraction thereof. Exemplary non-human surfactants include bovine, porcine or ovine lung surfactants or a fraction thereof. The non-human surfactant may be harvested from the lungs of a non-human mammal using techniques that are well known in the art. For example, porcine surfactant may be obtained from newborn and/or adult pigs harvesting the bronchoalveolar lavage (BAL) of the lungs with saline as described in Bernhard et al., *Am. J. Respir. Cell Mol. Biol.* 17:41-50 (1997), which is incorporated herein by reference. Harvested BAL fluid is centrifuged to remove cells and then the cell-free BAL fluid is further centrifuged to generate a raw surfactant pellet. Ovine surfactant may be obtained from whole lung lavages of adult sheep as described by Brackenbury et al., *Am. J. Respir Cir. Care Med.* 163:1135-1142 (2001), which is incorporated herein by reference. The harvested alveolar lavage is centrifuged to remove cellular debris, followed by further centrifugation to obtain a pellet corresponding to a surfactant aggregate pellet. Bovine surfactant may also be obtained from the lung lavages of adult cows as described by Panda et al. (*J Colloid Interface Sci.,* 311:551-5 (2007)), which is incorporated herein by reference. Alveofact®, a natural bovine surfactant extract containing phospholipids, neutral lipids, SP-B and SP-C polypeptides may also be used.

Proteins and polypeptides derived from or having characteristics similar to those human lung surfactant may also be used. For example, SP-B may be isolated from bovine surfactant using differential organic extraction, column chromatography, and/or preparative SDS-PAGE as described by Beers et al., *Am. J. Physiol Lung Cell Mol. Physiol.* 262: L773-L778 (1992), which is incorporated herein by reference.

The mammalian lung surfactant polypeptides or portion thereof can also be recombinantly produced. Recombinant SP-A, SP-B, SP-C, SP-D, or a portion thereof is obtainable by expression of a DNA sequence coding for SP-A, SP-B, SP-C, SP-D, or a portion thereof in a suitable prokaryotic or eukaryotic expression system using various known techniques. Recombinant vectors, which are readily adapted to include a isolated nucleic acid encoding a surfactant polypeptide or a portion thereof, host cells containing the recombinant vectors, and methods of making such vectors and host cells as well as using them for the production of the encoded polypeptides by recombinant techniques are well-known. The nucleic acids encoding a surfactant polypeptide or a portion thereof may be provided in an expression vector comprising a nucleotide sequence encoding a surfactant polypeptide that is operably linked to at least one regulatory sequence. It should be understood that the design of the expression vector may depend on such factors as the choice of the host cell to be transformed and/or the type of protein desired to be expressed. The vector copy number, the ability to control that copy number, and the expression of any other protein encoded by the vector, such as antibiotic markers, should be considered. The subject nucleic acids may be used to cause expression and over-expression of a kinase or phosphatase polypeptide in cells propagated in culture, e.g., to produce proteins or polypeptides, including fusion proteins or polypeptides.

Host cells may be transfected with a recombinant gene in order to express a surfactant polypeptide or portion thereof. The host cell may be any prokaryotic or eukaryotic cell. For example, a polypeptide may be expressed in bacterial cells, such as *E. coli*, insect cells (baculovirus), yeast, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the polypeptide will be known to those in the art.

Methods of producing polypeptides are well-known in the art. For example, a host cell transfected with an expression vector encoding a surfactant polypeptide or portion thereof may be cultured under appropriate conditions to allow expression of the polypeptide to occur. The polypeptide may be secreted and isolated from a mixture of cells and medium containing the polypeptide. Alternatively, the polypeptide may be retained cytoplasmically. Cells are then harvested, lysed, and the protein is isolated from the cell lysates.

A cell culture includes host cells, media, and other by-products. Suitable media for cell culture are well known in the art. The polypeptide may be isolated from cell culture medium, host cells, or both using techniques known in the art for purifying proteins, including ammonium sulfate or ethanol precipitation, acid extraction, anion or cation exchange chromatography, gel filtration chromatography, phosphocellulose chromatography, hydrophobic interaction chromatography, affinity chromatography, hydroxylapatite chromatography, lectin chromatography, ultrafiltration, electrophoresis, immunoaffinity purification with antibodies specific for particular epitopes of a polypeptide of the invention, and high performance liquid chromatography ("HPLC") is employed for purification. Thus, a nucleotide sequence encoding all or a selected portion of a surfactant polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant polypeptides of the invention by microbial means or tissue-culture technology.

Expression vehicles for production of a recombinant protein include plasmids and other vectors. For instance, suitable vectors for the expression of a polypeptide of the invention include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-I), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the [beta]-gal containing pBlueBac III).

In another embodiment, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, IU.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs. When expression of a carboxy terminal fragment of a polypeptide is desired, i.e., a truncation mutant, it may be necessary to add a start codon (ATG) to the oligonucleotide fragment containing the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J Bacteriol.* 169:751-757) and *Salmonella typhimurium* and its in vitro activity has been demonstrated on recombinant proteins (Miller et al., (1987) *PNAS USA* 54:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al).

Polypeptides of the invention may also be subject to various changes, such as insertions, deletions, and substitutions, either conservative or non-conservative, where such changes provide for certain advantages in their use. Conservative substitutions are those in which one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

Polypeptides of the invention may also be truncated relative to the full-length mature polypeptide. Polypeptides may be truncated at either the amino-terminus, carboxy-terminus, or both termini. Polypeptides may be truncated by at least one amino acid, or at least 5, 10, 15, 20, 25, 30, 35, 40, 45, 50, 55, 60, 65 or 70 amino acids.

A mammalian lung surfactant polypeptide or a portion thereof can be synthesized from amino acids by techniques that are known to those skilled in the polypeptide art. A summary of the many techniques available may be found in J. M. Steward and J. D. Young, "Solid Phase Peptide Synthesis", W.H. Freeman Co., San Francisco, 1969, and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group (e.g., lysine).

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and any solid support) are removed sequentially or concurrently, to afford the final polypeptide. That polypeptide is then washed by dissolving in a lower aliphatic alcohol, and dried. The dried surfactant polypeptide can be further purified by known techniques, if desired.

In certain embodiments, commonly used methods such as t-BOC or f-MOC protection of alpha-amino groups can be used. Both methods involve stepwise syntheses whereby a single amino acid is added at each step starting from the C-terminus of the peptide (See, Coligan et al., *Current Protocols in Immunology*, Wiley Interscience, 1991, Unit 9). Peptides of the invention can be synthesized, for example, by the well known solid phase peptide synthesis methods described in Merrifield, *J. Am. Chem. Soc.* 85: 2149, 1962, and Stewart & Young, 1969, Solid Phase Peptides Synthesis, pp. 27-62, using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

In one embodiment, recombinant and/or synthetic SP-B peptides contain amino acids 2, 4, 6, and 9 of SEQ ID NO:5. Prolines 2, 4, and 6 and tryptophan 9 of SEQ ID NO:5 may constitute essential structural motifs for protein function. In some embodiments, SP-B peptides may be substituted at any amino acid residue other than tryptophan 9 amino acid (relative to SEQ ID NO:5).

A lung surfactant polypeptide mimic is generally a polypeptide that is engineered to mimic the essential attributes of human surfactant protein. An exemplary mimetic peptide mimics SP-B. One example of a SP-B mimic is KL4, a 21 amino acid residue peptide comprising the sequence KLLLLKLLLLKLLLLKLLLLK (SEQ ID NO: 94). This SP-B mimetic protein is also known as Lucinactant (Surfaxin®, Discovery Laboratories).

Surfactant Lipids

In certain embodiments, a surface active agent for use in the invention comprises a surfactant protein, a portion thereof, or a mixture thereof, which associates with natural surfactant lipids in vivo. In other embodiments, a surface active agent for use in the invention comprises a lipid or a lipid-protein complex.

Natural mammalian lung surfactant is a complex of phospholipids, neutral phospholipids, and proteins. Surface active agent for use in the invention disclosed herein may comprise one or more lipids. In some embodiments, the surface active agent can comprise, for example, from as little as about 0.05 to 100% weight percent lipid, so long as the resulting composition has surfactant activity. By weight percent is meant the percentage of a compound by weight in a composition by weight. Thus, a composition having 50 weight percent lipid contains, for example, 50 grams lipids per 100 grams total composition. A surface active agent may contain 0.1 to 50 weight percent lipid, although higher concentrations of lipid can be used. Surface active agents containing both phospholipid and a surfactant polypeptide or portion thereof can contain, therefore, 0.1, 1, 10, 50, 80, to almost 100 weight percent lipid and about 50, 20, 10, to less than 1 weight percent surfactant polypeptide. Alternatively, surface active agents may contain the reverse ratios of lipid to surfactant polypeptide.

The term "lipid" as used herein refers to a naturally occurring, synthetic or semi-synthetic (i.e., modified natural) compound which is generally amphipathic. The lipids typically comprise a hydrophilic component and a hydrophobic component. Exemplary lipids include, but are not limited, phospholipids, fatty acids, fatty alcohols, neutral fats, phosphatides, oils, glycolipids, aliphatic alcohols, waxes, terpenes and steroids. The phrase semi-synthetic (or modified natural) denotes a natural compound that has been chemically modified in some fashion.

Examples of phospholipids include native and/or synthetic phospholipids. Phospholipids that can be used include, but are not limited to, phosphatidylcholines (saturated and unsaturated), phospatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidylserine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, and egg phosphatidylcholine (EPC).

Examples of fatty acids and fatty alcohols include, but are not limited to, sterols, palmitic acid, cetyl alcohol, lauric acid, myristic acid, stearic acid, phytanic acid, dipamlitic acid, and the like. Exemplary fatty acids include palmitic acid.

Examples of fatty acid esters include, but are not limited to, methyl palmitate, ethyl palmitate, isopropyl palmitate, cholesteryl palmitate, palmityl palmitate sodium palmitate, potassium palmitate, tripalmitin, and the like.

Surfactant polypeptide and surfactant lipids interact by hydrostatic interactions. Charged amino acids interact with the lipid polar head groups and hydrophobic amino acids interact with phospholipid acyl side chains. For example, SP-B and SP-C are hydrophobic proteins. Both SP-B and SP-C preferentially bind anionic lipids, such as phosphatidylglycerol (PG), and not DPPC. SP-A and SP-D are hydrophilic proteins and interact with a broad range of amphipathic lipids, including glycerophospholipids, sphingophospholipids, glycosphingolipids, lipid A, and lipoglycans. SP-A binds DPPC. By way of example, hydrostatic interactions are observed with the SP-B mimetic, KL4, and lipids in natural surfactant or lipids comprised in the surface active agent. For example, the lysine residues in the KL4 peptide interact with the charge head groups of DPPC and the hydrophobic leucine resides interact with the phospholipid acyl side chains of phosphatidylglycerol.

In certain embodiments, a drug composition as disclosed herein comprises a surface active agent comprising a portion of a mammalian lung surfactant polypeptide or mimic thereof and does not additionally comprise a lipid or a mixture of lipids. Drug compositions administered by inhalation comprising surface active agents comprising only a portion of a mammalian lung surfactant polypeptide or mimic thereof can interact with natural surfactant in the lungs through hydrostatic interactions. For example, recombinant SP-B can interact with natural surfactant in the lungs by binding anionic phospholipids, such as phosphatidylglycerol.

In other embodiments, a drug composition as disclosed herein comprises a surface active agent comprising both a portion of a mammalian lung surfactant polypeptide or a mimic thereof and at least one lipid. To facilitate absorption of drug compositions comprising both a polypeptide or mimic thereof and at least one lipid into natural surfactant in the lungs, phopholipid monolayers mimicking those found in natural surfactant can be used. Exemplary lipid mixtures include dipalmitoylphosphatidylcholine/palmitoyloleoylphosphatidylglycerol, for example at a 7:3 w/w ratio. The mammalian lung surfactant polypeptide can be inserted into the phosphoplipid monolayer and the protein/lipid mix can be absorbed into the natural surfactant at the alveolar/gas interface in the lungs following inhalation.

Pulmonary Active Drugs

The pulmonary active drug portion of the conjugate may be any drug that has utility in the management or treatment of lung disease and, preferably are those characterized by a molecular weight below about 10,000 KD, e.g., a drug moiety having a molecular weight below about 5,000 KD, or about 2000 KD.

Pulmonary active drugs may include, but are not limited to elastase inhibitors, corticosteroids, bronchodilators, antihistamines, antibiotics, P2X and P2Y agonists, chemotherapeutic agents, matrix metalloproteinase inhibitors, ADAM inhibitors, kinase inhibitors, endothelin receptor antagonists, prostacyclin analogues, and phosphodiesterase type 5 inhibitors.

Exemplary elastase inhibitors include the compounds shown in FIG. 17. Other exemplary elastase inhibitors include the compounds described by Philip D. Edwards and Peter R. Bernstein in "Synthetic Inhibitors of Elastase," Medicinal Research Reviews, Vol. 14, No. 2, 127-194 (1994), which is incorporated herein by reference. Two or more elastase inhibitors may be linked to a surface active agent of the invention and administered in combination. Alternatively, an elastase inhibitor may be linked to a surface active agent and administered in combination with a second elastase inhibitor linked to a surface active agent.

Exemplary corticosteroids that may be delivered to the lung include, but are not limited to, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, fluticasone propionate, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, and ulobetasol. Two or more corticosteroids may be linked to a surface active agent of the invention and administered in combination. Alternatively, a corticosteroid may be linked to a surface active agent and administered in combination with a second corticosteroid linked to a surface active agent.

Pulmonary active drugs may also include bronchodilators such as short-acting β2-adrenergicreceptor agonists, long-acting β2-adrenergic receptor agonists, short-acting anti-cholinergics, and long-acting anti-cholinergics. Non-limiting short-acting β2-adrenergic receptor agonists include salbutamol or albuterol, terbutaline, fenoterol, fenoterol hydrobromide, rimiterol, reproterol, pirbuterol, isoprenaline, orciprenaline, bitolterol, and broxaterol. Non-limiting long-acting β2-adrenergic receptor agonists include salmeterol, salmeterol xinafoate, formoterol, formoterol fumarate, clenbuterol, and procaterol. Non-limiting short-acting anti-cholinergics include ipratropium, ipratropium bromide, oxitropium and its salts. Non-limiting long-acting anti-cholinergics include tiotropium and tiotropium bromide monohydrate. Other bronchodialators may include, but are not limited to, aminophyliline, iorciprenaline, oxtriphylline, terbutaline sulfate, and theophylline. Two or more bronchodilators may be linked to a surface active agent of the invention and administered in combination. Alternatively, a bronchodilator may be linked to a surface active agent and administered in combination with a second bronchodilator linked to a surface active agent.

Pulmonary active drugs may also include antihistamines. Exemplary antihistamines include, but are not limited to as acrivastine, astemizole, azatadine, azelastine, brompheniramine, cetirizine, chlorpheniramine, cyclizine, cyproheptadine, diphehydramine, desloratidine, fexofenadine, hydroxyzine, levocetirizine, loratidine, meclizine, mepyramine, methscopolamine, misolastine, phenidamine, promethazine, pyrilamine, tecastemizole, and terfenadine. Two or more antihistamines may be linked to a surface active agent of the invention and administered in combination. Alternatively, an antihistamine may be linked to a surface active agent and administered in combination with a second antihistamine linked to a surface active agent.

U.S. Pat. No. 7,173,102, the disclosure of which is incorporated herein by reference, discloses anti-microbial polymers that are designed to possess amphiphilic properties in the presence of microbial cell walls and to disrupt the membrane and kill the organism. The polymeric materials are further designed to have low toxicity to mammalian cells. These facially amphiphilic polymers are capable of adopting repeating secondary structural motifs that allow for the segregation of polar and nonpolar regions of the molecule into different spatial regions. The anti-microbial polymers adopt amphiphilic conformations when placed in contact with the cell walls of microorganisms and the amphiphilic molecules are capable of disrupting essential cell wall functions resulting in the death of the microorganism with a much smaller death rate or no death rate for animal cells, thus providing a useful therapeutic margin for the treatment of infections. Many of these amphiphilic polymers are beta peptides. They can be synthesized as a leader or trailer sequence to the full length or a portion of a mammalian lung surfactant polypeptide or a mimic thereof to produce a potent lung targeted antimicrobial inhalant for the treatment of microbial lung infections including MRSA infections and various dangerous nosocomial infections.

Exemplary antibiotics that may be delivered to the lung include, but are not limited to penicillins, penicillins and beta-lactamase inhibitors, cephalosporins (generation I, II, III, and IV), macrolides and lincosamines, quinolones and fluoroquinoloes, carbepems, monbactams, aminoglycosides, glycopeptides, tetracylines, sulfonamides, rifampin, oxazolidones, streptogramins, sulfanomides, and others. Two or more antibiotics may be linked to a surface active agent of the invention and administered in combination. Alternatively, an antibiotic may be linked to a surface active agent and administered in combination with a second antibiotic linked to a surface active agent.

Exemplary penicillins include, but are not limited to, amoxicillin, ampicillin, bacampicillin, carbenicillin, carbenicillin indanyl, mezlocilin, piperacillin, and ticarcilin.

Exemplary penicillins and beta-lactamase inhibitors include, but are not limited to, amoxicillin-clavulanic acid, ampicillin-sulbactam, benzylpenicillin, cloxacilin, dicloxacilin, phenoxymethylpenicillin, carbenicillin, methicillin, oxacilin, penicillin G (benzathine, potassium, procaine), penicilin V, propicillin, epicillin, cyclacillin, piperacilin plus tazobactam, ticarcilllin plus clavulanic acid, and naficillin.

Exemplary cephalosporins (generation I) include, but are not limited to, cefadroxil, cefazolin, cephalexin, cephalothin, cephapirin, and cephradine. Cephalosporins (generation II) include, but are not limited to, cefaclor, cefamandole, cefoicid, ceforanide, cefoxitin, cefprozil, ceftmetazole, cefuroxime, cefuoxime axetil, and loracarbef. Cephalosporins (generation III) include, but are not limited to, cefdinir, ceftibuten, cefditoren, cefatamet, cefoperazone, cefixime, cefotaxime, cefpodoxime, ceftazidime, ceftibuten, ceftizoxime, and ceftriaxone. Cephalosporins (generation IV) include, but are not limited to, cefepime.

Exemplary marcolides and lincosamine include, but are not limited to, azithromycin, clarithromycin, clindamycin, dirithromycin, erythromycin, lincomycin, telithromycine, and troleandomycin.

Monobactams include, but are not limited to, include aztreonam. Carbepenems include, but are not limited to, doripenem, imipenem-cilastatin, and meropenem.

Aminoglycosides include, but are not limited to, amikacin, amikacin sulfate, gentamicin, genatmicin sulfate, kanamycin, metilmicin, neomycin, netilmicin, streptomycin, tobramycin, and paromycin.

Glycopeptides include, but are not limited to, dalbavancin, oritavancin, telavancin, teicoplanin, and vancomycin.

Tetracylines include, but are not limited to, demclocylline, doxycycline, methacyline, minocyline, oxytetracycline, tetracyline, and chloretracycline.

Oxazolidonones include, but are not limited to linezolid. Streptogramins include but are not limited to quinoprisitin plus dalfopristin.

Sulfonamides include, but are not limited to mafenide, silver sulfadiazine, sulfacetamide, sulfadiazine, sulfamethoxazole, sulfasalzine, sulfanilamide, sulfisoxazole, trimethoprim-sulfamethoxazole, and sulfamethizole.

Other antibiotics include, but are not limited to, bacitracin, chloramphenical, Colistemetate, Fosfomycin, Isoniazid, Methenamine, Metronidazol, Mupirocin, Nitrofurantoin, Nitrofurazone, Novobiocin, Polymyxin (for example, Polymyxin B), Spectinomycin, Trimethoprim, Colistin, Cycloserine, Capreomycin, Pyrazinamide, Para-aminosalicyclic acid, Erythromycin ethylsuccinate plus sulfisoxazole, and tigecycline.

P2X agonists that may be delivered to the lung include, but are not limited to, ATP, and an ATP analogue (e.g., benzoyl derivatives of ATP). In one embodiment, ATP or an ATP analogue may be linked to a lung surfactant peptide for treatment as a tuberculosis-treating antibiotic. This will persist in the lung, bind to a P2X receptor expressed by macrophages harboring TB, and drive the macrophages along an apoptotic pathway, thus treating the latent TB. For disclosure of established techniques for chemically linking ATP or its analogs peptides, see, for example, Ahn, et al., "ATP-Conjugated Peptide Inhibitors for Calmodulin-Dependent Protein Kinase II," *Bioorganic and Medicinal Chemistry Letters*, 2007. Two or more P2X agonists may be linked to a surface active agent of the invention and administered in combination. Alternatively, a P2X agonist may be linked to a surface active agent and administered in combination with a second P2X agonist linked to a surface active agent.

P2Y agonists that may be delivered to the lung include, but are not limited to denufosol tetrasodium, ATP, and an ATP analogue. P2Y agonists may be linked to a lung surfactant peptide for the treatment of cystic fibrosis. Two or more P2Y agonists may be linked to a surface active agent of the invention and administered in combination. Alternatively, a P2Y agonist may be linked to a surface active agent and administered in combination with a second P2Y agonist linked to a surface active agent.

Chemotherapeutic drugs that may delivered to the lung include, but are not limited to, alkylating agents, antiestrogens, aclarubicin, actinomycin D, aldesleukin, alemtuzumab, alitertinoin, allopurinol, altretamine, amifostine, anastrozole, asparaginase, bexarotene, bisantrene, bleomycin, busulfan, BCNU (carmustine), calusterone, capecitabine, carboplatin, celecoxib, chlorambucil, cisplatin, cladribine, cyclophosphamide, cyclooxygenase-2 inhibitor, cytarabine, CCNU (lomustine), dacarbazine, daunorubine, daunomycin, denileukin diftitox, dexrazoxane, diaziquone, docetaxel, doxorubicin, epirubicin, epoetin alfa, esorubicin. estramustine, etoposide (VP-16), exemestane, Filgrastim, floxuridine, fludarabine, 5-fluorouracil, fulvestrant, galactitol, gemcitabine, gemtuzumab, goserelin acetate, hydroxyurea, ibritumomab tiuxetan, idarubicin, ifosfamide, imatinib mesylate, interferon alpha, interferon gamma, iriniotecan, iroplatin, letrozole, leucovorin, levamisole, lonidamine, megrestrol acetate, melphalan, mercaptopurine, mesna, methotrexate, methoxsalen, mitomycin C, mitotane, mitoxantrone, mitoguazone, nandrolone phenpropionate, Nofetumomab, nitrogen mustard, oprelvekin, oxaliplatin, paclitaxel, pamidronate, pegademase, pegaspargase, pegfilgrastim, pentostatin, pipobroman, plicamycin, porfimer sodium, procarbazine, progestins, prednimustine, PCNU, quinacrine, rasburicase, rituximab, sargramostim, streptozocin, talc, tamoxifen, temozolomide, teniposide (VM-26), testolactone, thioguanine, thiotepa, topotecan, toremifene, tositumomab, trastuzumab, tertinoin, uracil mustard, valrubicin, vinblastine, vincristine, vindesine, vinorelbine, and zoledronate.

Two or more chemotherapeutic agents may be linked to a surface active agent of the invention and administered in combination. Alternatively, a chemotherapeutic agent may be linked to a surface active agent and administered in combination with a second chemotherapeutic agent linked to a surface active agent. Exemplary combination therapies include paclitaxel and carboplatin, cisplatin and vinorelbline tartrate, cisplatin and etoposide, and carboplatin and etoposide.

Pulmonary active drugs may include endothelin receptor antagonists. Exemplary endothelin receptor antagonists include, but are not limited to, tezosentan and bosentan, which are dual receptor antagonists affecting both endothelin A and endothlin B receptors, and sitaxentan, ambrisentan, and atrasentan, which affect endothelin A receptors.

Exemplary prostacylin analogues include, but are not limited to, Beraprost, Epoprostenol, Iloprost, and Treprostinil.

Exemplary phosphodiesterase type 5 inhibitors include, but are not limited to, sildenafil, tadalafil, and vardenafil.

Salts or solvates of the above identified pulmonary active drugs for use in the conjugates described herein are also contemplated.

Other exemplary inhibitors that may be linked to a surface active agent of the invention include, but are not limited to marimastat (a nonselective inhibitor of sheddase and matrix metalloproteinase enzymes), selective ADAM inhibitors such as INCB3619 (see Zhou et al., *Cancer Cell*, 10:39-50 (2006)), and EGFR tyrosine kinase inhibitors such as gefitinib and erlotinib. Two or more matrix metalloproteinase or kinase inhibitors may be linked to a surface active agent of the invention and administered in combination. Alternatively, a matrix metalloproteinase inhibitor (e.g., marimastat) may be linked to a surface active agent and administered in combination with a second agent (e.g., a second matrix metalloproteinase inhibitor, a kinase inhibitor, or a chemotherapeutic agent) linked to a surface active agent.

In other embodiments, the pulmonary active drug may be a polypeptide such as an antibody (e.g., an intact antibody, an antigen binding fragment such as a Fab, Fab', (Fab')$_2$, Fv fragment, or a biosynthetic antibody such as a single Fv or SFv molecule), a fusion protein, or a peptidomimetic, that binds an extracellular or cell surface target, e.g., an elastase, a TNF receptor, an EGF receptor, an adrenergic receptor, a P2X or P2Y purinergic receptor, or an endothelin receptor, or other target accessible to the pulmonary/gas interface. It is further contemplated that such polypeptide drugs may be directed against any target which is addressed by the drugs disclosed herein.

Linkage

Many strategies can be employed to link a pulmonary active drug to a surface active agent for use in the invention. Preferably, the pulmonary active drug can be attached to the surface active agent covalently either directly or using a linker that preserves the biological activity of the drug and retains significant dwell time of the surface active agent at the lung/air interface. In this case, at least one additional residue can be added at the amino- or carboxy-terminus or at an internal amino acid residue of a surfactant polypeptide of the type disclosed herein to generate a linker for covalently bonding a drug molecule. In an exemplary embodiment, SP-A, SP-B, SP-C, SP-D, or portions thereof, may be extended by at least one amino acid to create an unnatural amino acid or short amino acid sequence, e.g., four to eight amino acids long, by automated peptide synthesis. Alternatively, the native sequence of the human or animal form of these protein domains beyond these regions displaying the surfactant activity may be included as a natural linker.

A drug can be conjugated to the C-terminal or N-terminal amino acid of the surface active agent by bonding with the carboxyl group of the C-terminal amino acid or the amino group of the N-terminal amino acid. The drug may be bonded directly to the amino acid or via a linker. Representative covalent linkages include an ester, an amide, urea, carbamate, sulfonamide, ether, thioether, disubstituted amino, or a trisubstituted amine. (March, Advanced Organic Chemistry, 4th Ed., John Wiley & Sons, 1992.) Other linkage types could also be used. One strategy is to synthesize a derivative of the pulmonary active drug as may be necessary in specific cases to create a selectively reactive chemical group in a region of the molecule chemically separate from its active region at locations suggested by structure function analysis studies.

One type of covalent linker comprises amino acid residues. Such linkers may comprise at least one residue or can be 40 or more residues, more often 1 to 10 residues, and most often 1 to 5 or 5-10 amino acid residues in length. The linker is usually a small, water-soluble, neutral polar or non-polar amino acid or unstructured peptide. Typical amino acid residues used for linking are glycine, tyrosine, cysteine, lysine, glutamic acid, and aspartic acid, or the like. One linker frequently used where linked moieties each are intended to retain their independent function is a glycine rich sequence comprising between one to five glycine residues. Another linker frequently used in similar contexts where linked moieties each are intended to retain their independent function is Glycine and Serine rich synthetic sequences such as Gly Gly Ser Gly Gly Ser Gly Gly Gly Gly Ser Gly Ser (SEQ ID NO: 95), or [Gly Gly Gly Gly Ser]$_n$(SEQ ID NO: 96) where n is one, two, or three.

In another embodiment, a pulmonary active drug may can be chemically linked to a surfactant moiety through a succinic acid-peptide linker. For example, a steroid, such as prednisone, can be bonded to succinic acid to form a steroid-succinate (e.g., a prednisone-succinate) then conjugated to a peptide linker, such as a glycine linker (e.g., [Gly]$_n$, where n is 1-5), as described by Penugonda et al. (*J. Pharm. Sci.* 2008, 97(7):2649-2664), which is incorporated herein by reference. The steroid-succinate-peptide conjugate can then be further conjugated with a surfactant moiety through the carboxyl group on the terminus of the glycine linker.

Other strategies for attaching a pulmonary active agent to a surface active agent are contemplated including by chelation, ionic attraction, or non-covalent association such as hydrophobic-hydrophobic interaction.

Figure 20:
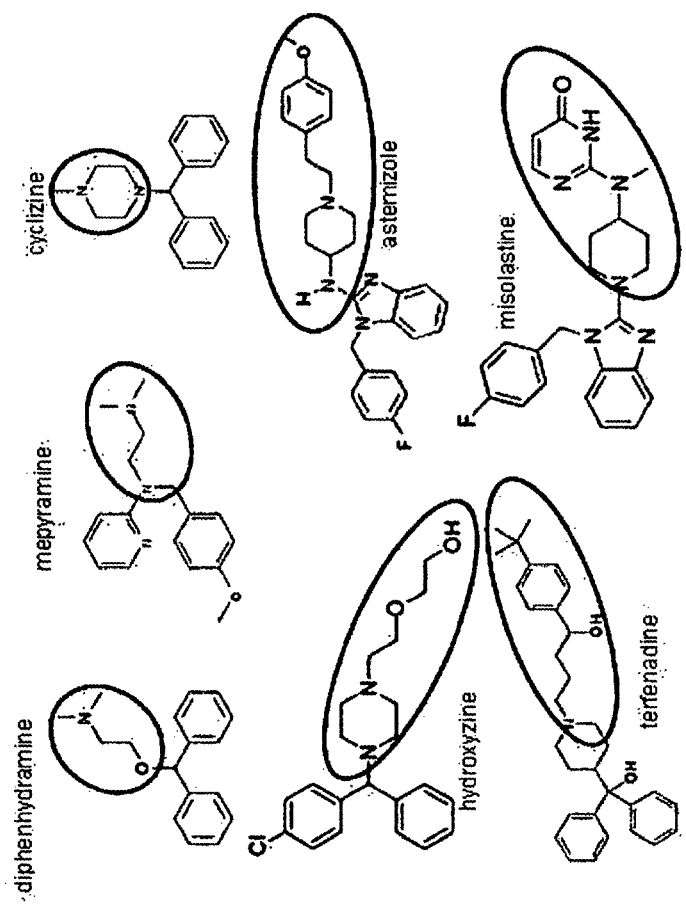
Figure 21:
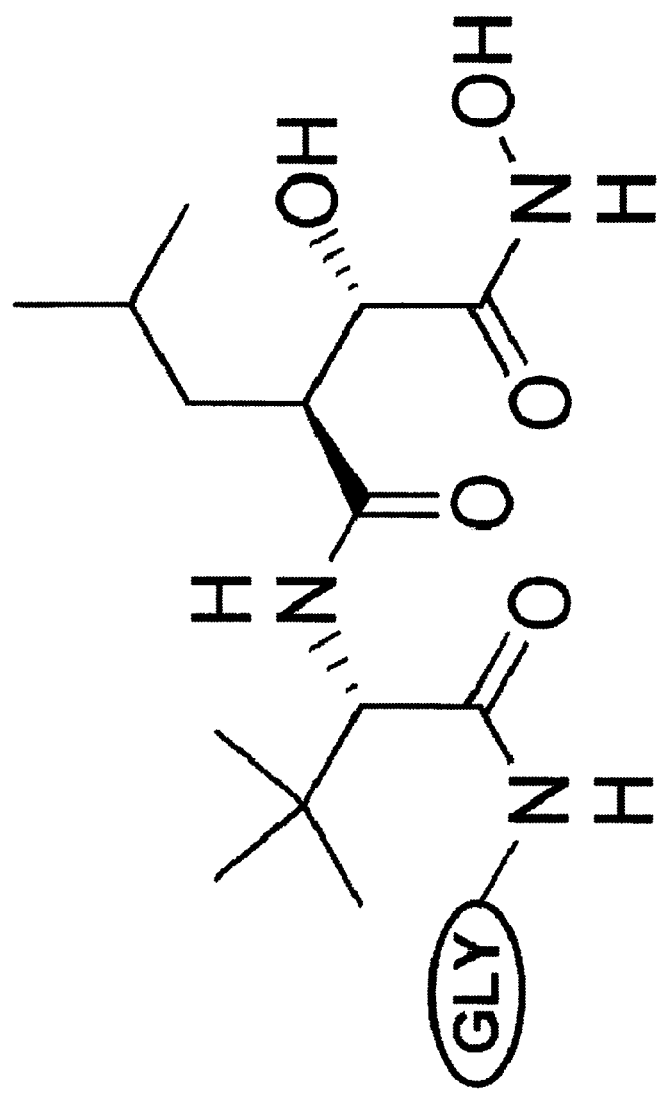

The chemical structure of the pulmonary active drug may also guide the site of attachment to a surfactant moiety. For example, many antihistamines have a biphenyl-like aromatic core with a basic nitrogen spaced about four atoms from the center of the aromatic core. Early generation antihistamines have short side chains, whereas newer generation antihistamines have longer side chains extending from the aromatic core. FIG. 20 is an exemplary collection of antihistamines, which demonstrates that large variations are well-tolerated on the antihistamine side chains, both short and long. As such, it is contemplated that attaching the surfactant moiety to the side chain of the antihistamine should not significantly impact the therapeutic properties of the antihistamine. For example, it is contemplated that attaching a surfactant moiety to the side chain hydroxyl group in hydroxyzine or terfenadine using a succinate-peptide linker will not significantly impact the therapeutic properties of these antihistamines. Similarly, it is contemplated that a surfactant moiety may be attached to the terminal carboxyl group of certirizine either directly or using a glycine linker. Further, it is contemplated that a surfactant moiety may be attached to the nitrogen atom of the terminal amide group of marimastat using a glycine linker as illustrated in FIG. 21.

Representative synthetic procedures for attaching various pulmonary active drugs to a polypeptide surfactant moiety either directly or using a linker are shown below in Scheme A.

Scheme A

A)

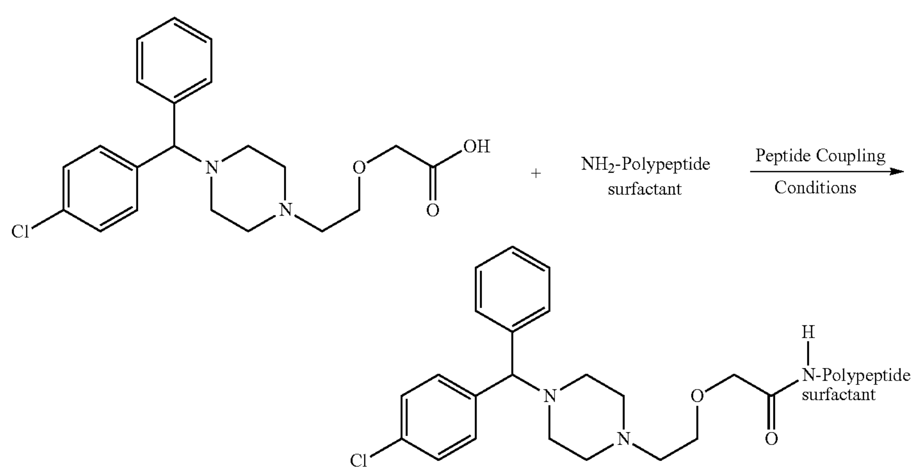

B)

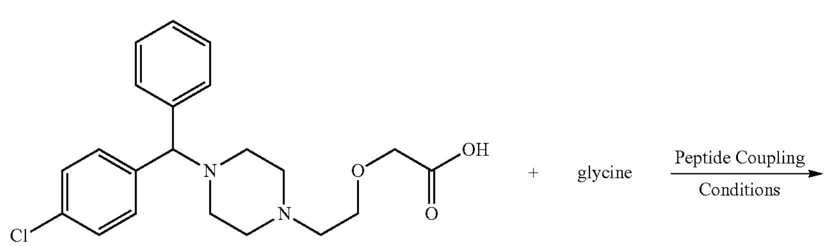

Further, one of skill in the art will appreciate, based on the teachings herein, that minor structure changes can be made to various pulmonary active drugs to make them more suitable for attachment to the surfactant moiety. For example, it is contemplated that one of the N-methyl groups of diphenhydramine could be replaced with a hydroxy ethylene group suitable for attachment to the surfactant moiety. Similarly, it is contemplated that one of the methoxy group of astemizole can be replaced with a hydroxyl group suitable for attachment to the surfactant moiety.

Once a pulmonary active drug and surfactant moiety have been selected, a library of fusion constructs may then be created, comprising individual species exploiting different points of attachment on the chemical structure of the drug and on the peptide, different length linkers, different linker chemistries, different length surfactant peptides, etc., all with a view to improving the binding constant of the drug to its target, improving activity, reducing immunogenicity, or for other purposes. The desired combination of different surfactant polypeptide domains, linkers, and attachment points can be generated, for example, by brute force construction of a desired number of candidate constructs. A library of such constructs may be generated using standard molecular biology protocols. As noted, the drug may be attached at either the N-terminal or the C-terminal, or at an intermediate location. The size/length, and amino acid sequence of the mammalian lung surfactant polypeptide or a mimic thereof may be varied. Nucleic acids encoding the various mammalian lung surfactant polypeptide or a mimic thereof can be recombinantly fused and cloned in suitable expression vectors, under the control of operatively linked promoters and transcription regulators. The construct may also be post translationally modified as may be necessary or desirable in specific instances, e.g., glycosylated or pegylated.

The resulting library can be screened for the ability to modify the specific target of interest in the lungs of experimental animals. An assay for the appropriate biological function can be used to quantitate the potency of the drug in vivo. For example, the assay to screen the library of fusion constructs can be one which measures the biological activity of the target molecule or a downstream molecule that is regulated by the target molecule such as a protocol described in the examples disclosed below.

Once one or a group of surfactant active agents are optimized for safety, distribution and dwell time within the lungs, by appropriate screening or otherwise, its properties may be further enhanced by one or more rounds of mutagenesis and additional selection/screening according to art known methods. This will lead to a functionally optimized structure, which can be used repeatedly to enhance the efficacy within the lungs of a wide variety of different pulmonary active drug classes and individual species for the treatment of various lung diseases.

Methods of Administration

Compositions of the invention are delivered to the lungs by inhalation. Inhalation devices, such as inhalers (including dry powder inhaler and metered dose inhalers) and nebulizers (also known as atomizers) may be used to deliver the disclosed compositions to the lungs. Exemplary dry powder inhalers can be obtained from Inhale Therapeutic Systems as described in U.S. Pat. Nos. 5,458,135; 5,740,794; 5,785,049, which are herein incorporated by reference. Dry powder inhalers can also be obtained from 3M as described in U.S. Pat. No. 6,029,661, which is incorporated herein by reference.

The compositions disclosed herein may also be administered using a metered dose inhaler (MDI) containing a solution or suspension of drug in a pharmaceutically inert liquid propellant, e.g., a chlorofluorocarbon (CFC) or fluorocarbon, as described in U.S. Pat. Nos. 5,320,094 and 5,672,581, both incorporated herein by reference. Metered dose inhalers are designed to deliver a fixed unit dosage of medicament per actuation or "puff", for example in the range of 10 to 5000 microgram medicament per puff. Exemplary metered dose inhibitors can be obtained from 3M as described in U.S. Pat. Nos. 5,224,183; 5,290,534; 5,511,540; 6,454,140; and 6,615,826, which are incorporated herein by reference. Metered dose inhalers may also be CFC-free. Drug compositions to be used with an inhaler may be in the form of aerosolized solid particles or droplets of liquid or suspension.

Alternatively, the compositions described herein may be dissolved or suspended in a solvent, e.g., water or saline, and administered by nebulization. Exemplary nebulizers for delivering an aerosolized solution include the AERx™ (Aradigm), the Ultravent®(Mallinkrodt), the Pari LC Plus™ or the Pari LC Star™ (Pari GmbH, Germany), the DeVilbiss Pulmo-Aide, and the Acorn II® (Marquest Medical Products).

Drug Formulation

Drug compositions disclosed herein can be formulated into a solution and/or a suspension of particles in a carrier appropriate for inhalation into the respiratory tract and the lungs. Such carriers are also well known to the ordinary artisan familiar with inhalants for the delivery of fine droplets and insufflations for the delivery of inhalable fine particles, on the order of, for example, from about 0.5 to 1 micron, and preferably from about 0.5 to about 0.7 micron, comprised of powders, mists or aerosols, into the respiratory tract as described in Remington's Pharmaceutical Sciences, 16th edition, 1980, Ed. By Arthur Osol, which is incorporated herein by reference.

In one embodiment, drug compositions for inhalation administration can be administered as powders. The powdered drug or composition is normally located within a container such as a hard gelatin capsule or a blister package, or a multi-dose devise. The capsule or blister is ruptured or broached within in an inhaler device, thereby enabling the powder to be inhaled. Generally, the mean particle size of the drug used for inhalation is between 1 and 10 micron with the size range between 2 and 5 microns being particularly suitable for penetrating the peripheral airways of the lungs. Such particle size ranges are commonly achieved by micronisation or spray drying.

A powdered drug composition is often administered as a composition comprising a blend or mixture of the medicament with an inert carrier. Usually the inert carrier has a mean particle size substantially larger than that of the drug. This provides, among other advantages, an improvement in the flow properties and dispensing accuracy of the composition.

Commonly described carrier materials for produced drug, include calcium carbonate and sugars, for example sucrose, mannitol or dextrose or, more particularly, lactose, which are pharmaceutically acceptable and pose no problems of toxicity, since any residues imbibed during dosing are well tolerated upon digestion or may be easily eliminated by disillusion (e.g., in the case of the sugars) or mucocilliary clearance from the lung.

The composition in the capsule or blister is frequently about 25 mgs. This weight probably represents the maximum quantity of powder that may be comfortably inhaled without undue side effects, such as coughing, and also corresponds to the minimum quantity that is usually dispensed by filling machines.

In certain embodiments, compositions formulated for powder inhalation comprise a carrier present at a concentration of about 95.0 to 99.99%. More particularly, from 97.0 to 99.9%, especially from 98.0 to 99.8%, by weight. Processes for preparing such powders, by the application or adaptation of known methods, also constitute features of the invention.

In other embodiments, the drug composition may be formulated as an aerosol formulation using methods well known in the art. One widely used method for dispensing such an aerosol formulation involves making a suspension formulation of the drug as a finely divided powder in a liquefied propellant gas. Alternatively a solution formulation can be prepared where the drug is dissolved in a propellant system, perhaps containing solubilizers and co-solvents to aid dissolution of the drug. Pressurized metered dose inhalers (pMDI) are normally used to dispense such formulations to a patient. Propellants may include chlorofluorocarbon (CFC), fluorocarban (FC), or hydrofluoroalkane (HFA) propellants.

Methods of Treatment

The disclosure also provides methods for treating a subject suffering from lung inflammation or lung disease. In another embodiment, the disclosure provides a method for treating a subject who is at risk of suffering from a lung disorder. The method comprises administering to the subject a conjugate comprising a pulmonary active drug covalently bonded to a surface active agent, which has an affinity for the human alveolar/gas interface and which comprises at least a portion of a mammalian lung surfactant polypeptide or a mimic thereof that is substantially non-immunogenic to humans. The conjugate is administered to the subject by inhalation in an amount effective to induce a drug effect in the lungs. The subject may be a human, monkey, chimpanzee, horse, dog, cat, cow, sheep, pig, rat or mouse. In exemplary embodiments, the subject is a human.

The subject in need of treatment is suffering from lung inflammation or is suffering from or at risk of suffering from lung disease. Exemplary lung diseases that may be treated with the drug composition described herein include, but are not limited to, emphysema, chronic bronchitis and acute exacerbation of chronic bronchitis (AECB), chronic obstructive pulmonary disease (COPD), asthma, respiratory distress disorder (RDS), pneumonia (including ventilator associated pneumonia), tuberculosis or other bacterial infection, cystic fibrosis, pulmonary arterial hypertension, and/or lung cancer.

Dosage

The administration of pulmonary active drugs conjugated to a surface active agent reduces the dosing frequency relative to administration of an unconjugated drug. In certain embodiments, the administration step may be repeated once daily, every other day, every three days, every four days, every five days, biweekly, or weekly.

EXAMPLES

The invention is further illustrated by the following examples. The examples are provided for illustrative purposes only, and are not to be construed as limiting the scope or content of the invention in any way.

Example 1

Conjugation of Human Neutrophil Elastase Inhibitors to a SP-B peptide

A panel of potent small molecule human neutrophil elastase (HNE) inhibitors can be conjugated to a SP-B peptide comprising the amino terminal 25 amino acids of SP-B (FPIPLPYCWLCRALIKRIQAMIPKG) (SEQ ID NO: 88). The total molecular weight of the SP-B peptide comprising the amino terminal 25 amino acids is 2926.97 after water molecule elimination. The HNE inhibitors are conjugated to the SP-B N-terminal 25-mer using a glycine linker similar to the linkage depicted in FIG. 18.

Example 2

Synthesis of Target B

All solvents used for the reaction were LR grade solvents. Room temperature (RT) indicates temperature ranging from 27-32° C. All the reactions were monitored by TLC unless specified. Solutions were evaporated under reduced pressure using rotary evaporator. NMR was taken on Varian 400 MHz. Column chromatography was done using silica gel 100-200 mesh unless specified.

Synthesis of Stage 1

Scheme 1

A solution of Cbz-Val-Pro-OH (5 g, 14 mmol) in dry tetrahydrofuran (85 mL) was cooled to −20° C. under nitrogen. N-methylmorpholine (1.74 mL, 15 mmol) followed by isobutyl chloroformate (2 mL, 15 mmol) was added to the reaction mixture. The reaction mixture was stirred at −20° C. for 15 min and then cooled to −40° C. A solution of L-Valinol (1.62 g, 15 mmol) in tetrahydrofuran (25 mL) was added drop wise to the reaction mixture. The reaction mixture was allowed to warm to room temperature overnight. The reaction mixture was filtered and the filtrate was diluted with ethyl acetate (60 mL). The combined organic layers were washed successively with 1N HCl (60 mL), NaHCO₃ (30 mL) and brine (30 mL). The organic layer was dried over sodium sulphate, filtered and concentrated to give the desired product (5.7 g). HPLC Rt: 5.76; LCMS (M+1): 434; Yield: 92.5%.

Synthesis of Stage 2

Scheme 2

Swern oxidation

A solution of oxalyl chloride (2.45 mL, 28 mmol) in dry dichloromethane (110 mL) was cooled to −60° C. and a solution of DMSO (4.09 mL, 57.7 mmol) in dichloromethane (35 mL) was added drop wise over a period of 1 h, maintaining the reaction mixture temperature at −45° C. The reaction mixture was allowed to warm to −30° C. and a solution of stage-1 (6.1 g, 14 mmol) in dichloromethane (35 mL) was added drop wise over a period of 1 h. The reaction mixture was stirred at −25° C. for 1 h. The reaction mixture was cooled to −40° C. and diisopropylethylamine (10 mL, 57.7 mmol)

was added drop wise over a period of 1 h. The reaction was warmed to room temperature and then washed with 1 N HCl (60 mL) and brine (60 mL). The organic layer was dried over sodium sulphate, filtered and the filtrate was concentrated under reduced pressure to give the desired product (5.7 g). HPLC Rt: 6.81; LCMS (M+1): 432; Yield: 94%.

Synthesis of Stage 3

Scheme 3

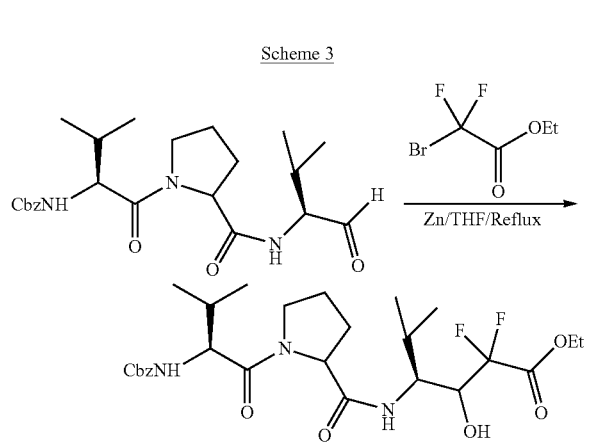

A suspension of Zinc (2.5 g, 39 mmol) and stage-2 (5.64 g, 13 mmol) in dry tetrahydrofuran (100 mL) was heated to 60° C. under nitrogen atmosphere. Ethyl bromodifluoroacetate (7.93 g, 39 mmol) was added and the reaction was heated to 60° C. for 1 h. The reaction mixture was cooled to room temperature, tetrahydrofuran was removed under reduced pressure and ethyl acetate (100 mL) was added. The reaction mixture was washed with 1M $KHSO_4$ (50 mL) and brine (50 mL) and dried over sodium sulphate. The organic layer was filtered and concentrated under reduced pressure to give the crude product, which was then purified by preparative HPLC to give the desired product (2.9 g). HPLC Rt: 7.44; LCMS (M+1): 556; Yield: 40%.

Synthesis of Stage 4

Scheme 4

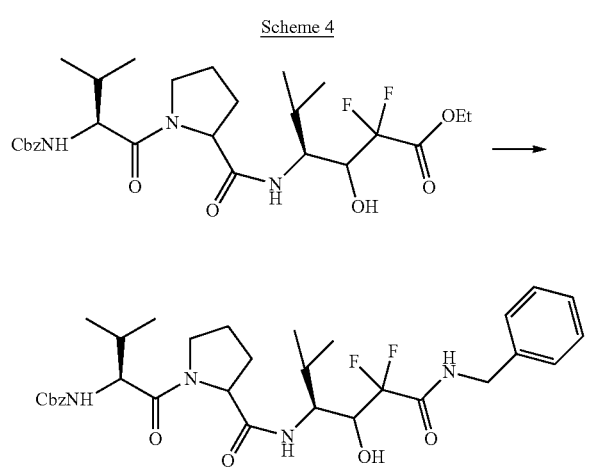

A solution of stage-3 (1.8 g, 3.2 mmol) and benzyl amine (1.06 mL, 9.7 mmol) in ethanol (40 mL) was stirred at reflux for 4 h. The reaction mixture was cooled to room temperature and stirred for an additional 48 h under nitrogen atmosphere. The solvent was removed under reduced pressure. The residue was dissolved in ethyl acetate (50 mL) and the solution was washed with 1N HCl (20 mL) and brine (20 mL). The organic layer was dried over sodium sulphate, filtered and the solvent was removed under vacuum to give the desired product (1.7 g). HPLC Rt: 7.56; LCMS (M+1): 616; Yield: 88%.

Stage-5

Scheme 5

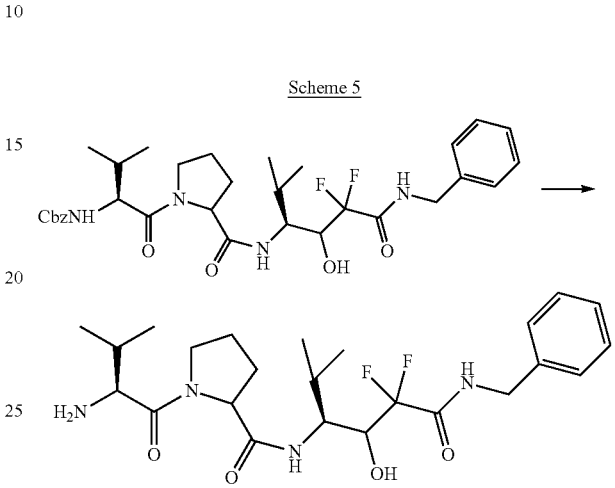

A mixture of stage-4 (1.85 g, 3 mmol) and 20% palladium hydroxide (1 g) in ethyl acetate (50 mL) was placed in a pressure vessel at 200 psi for 20 h. The reaction mixture was filtered through celite and the filtrate was concentrated under vacuum to give the desired product along with some starting material, which was used as such for further reaction without any purification (1.1 g). HPLC Rt: 4.90; LCMS (M+1): 482; Yield: 80%.

Stage-6

Scheme 6

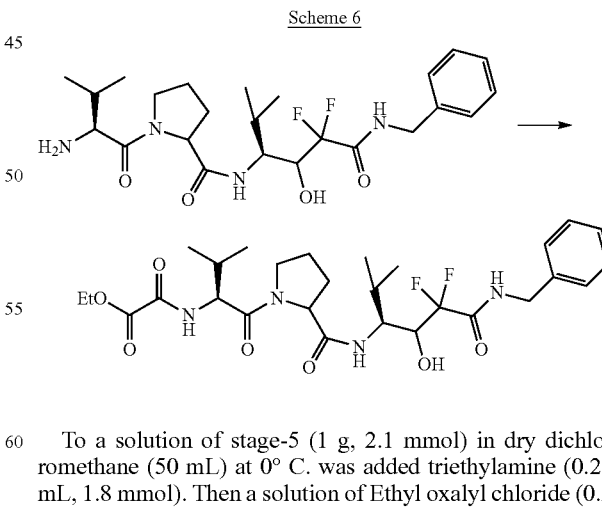

To a solution of stage-5 (1 g, 2.1 mmol) in dry dichloromethane (50 mL) at 0° C. was added triethylamine (0.25 mL, 1.8 mmol). Then a solution of Ethyl oxalyl chloride (0.2 mL, 1.87 mmol) in dichloromethane (20 mL) was added drop wise. The reaction mixture was allowed to warm to room temperature and stirred for further 2 h. The reaction mixture was quenched with water (25 mL). The organic layer was separated, dried over sodium sulphate and evaporated under reduced pressure to give the desired product, which was then purified by preparative HPLC. HPLC Rt: 6.72; LCMS (M+1): 583; Yield: 0.5 g (42%).

Stage-7

Scheme 7

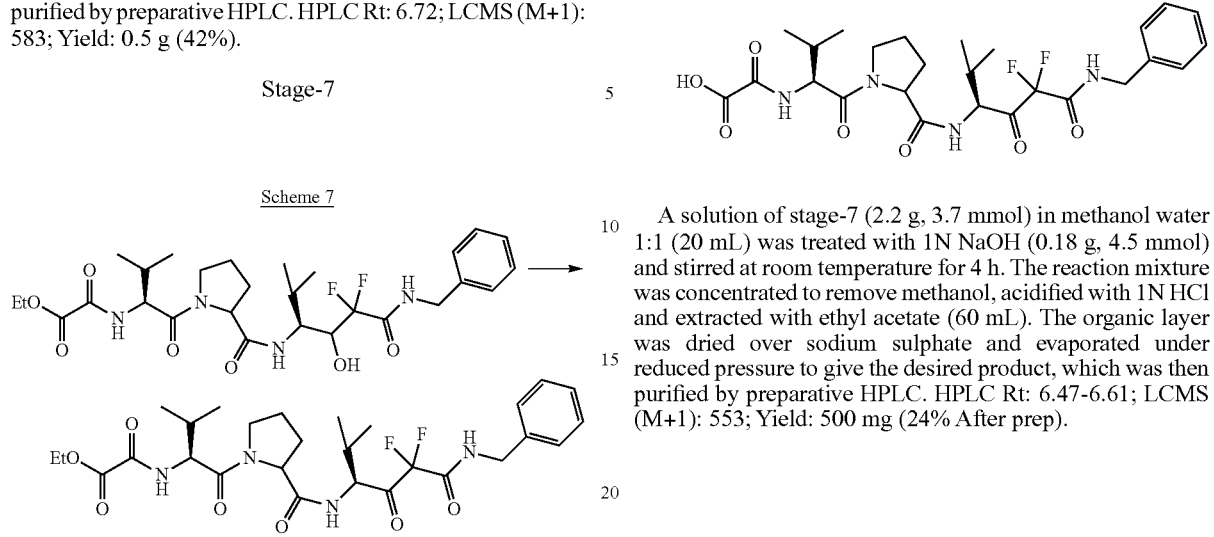

Trifluoroacetic acid (0.92 mL, 12.02 mmol) was added to a stirred solution of stage-6 (1.75 g, 3 mmol) and Dess-Martin periodinane (5.1 g, 12.02 mmol) in dry dichloromethane (25 mL). The mixture was stirred for 4 h at room temperature under nitrogen atmosphere. Ethyl acetate (100 mL) was added and the mixture was washed with saturated sodium thiosulphate (60 mL), saturated NaHCO$_3$ (60 mL) and brine (60 mL). The organic layer was dried over sodium sulphate, filtered and evaporated under reduced pressure to give the desired product, which was used as such for the further step. HPLC Rt: 7.32; LCMS (M+1): 581; Yield: 1.7 g (97%).

Stage-8

Scheme 8

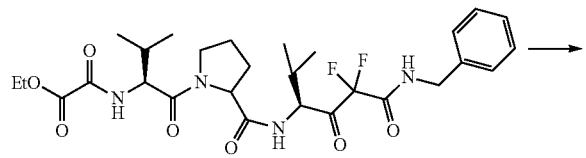

A solution of stage-7 (2.2 g, 3.7 mmol) in methanol water 1:1 (20 mL) was treated with 1N NaOH (0.18 g, 4.5 mmol) and stirred at room temperature for 4 h. The reaction mixture was concentrated to remove methanol, acidified with 1N HCl and extracted with ethyl acetate (60 mL). The organic layer was dried over sodium sulphate and evaporated under reduced pressure to give the desired product, which was then purified by preparative HPLC. HPLC Rt: 6.47-6.61; LCMS (M+1): 553; Yield: 500 mg (24% After prep).

Stage-9

Scheme 9

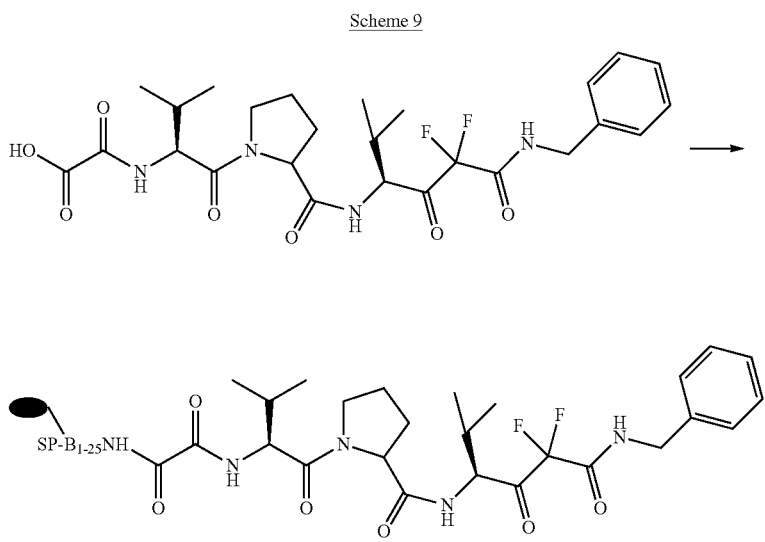

Wang resin (2.5 g, 0.5 eq) was treated with 20% piperidine in DMF (15 mL) and stirred for about an hour. It was then washed with DMF (2 times, 15 mL), DCM (3 times, 15 mL) and then dried under vacuum. Kaiser test was performed on the resin to ensure complete removal of F-moc group. Then it was used for coupling with the stage –8 product. To a solution of the resin in DMF was added a solution of the above acid (97 mg, 0.176 mmol) in DMF (5 mL), followed by the addition of PyBoP (91 mg, 0.176 mmol) and N-methyl morpholine (0.24 mL, 0.22 mmol). The reaction mixture was allowed to shake on a shaker for about 3 h. The solution was decanted, fresh lot of the above reagents was again added and it was further allowed to shake for 3 h. This process was repeated for about 4 times. The solution was decanted, and the resin was washed with DMF (3 times, 15 mL), DCM (3 times, 15 mL) dried under vacuum. Kaiser test was performed on the resin to ensure that the coupling has taken place.

Stage-10

Scheme 10

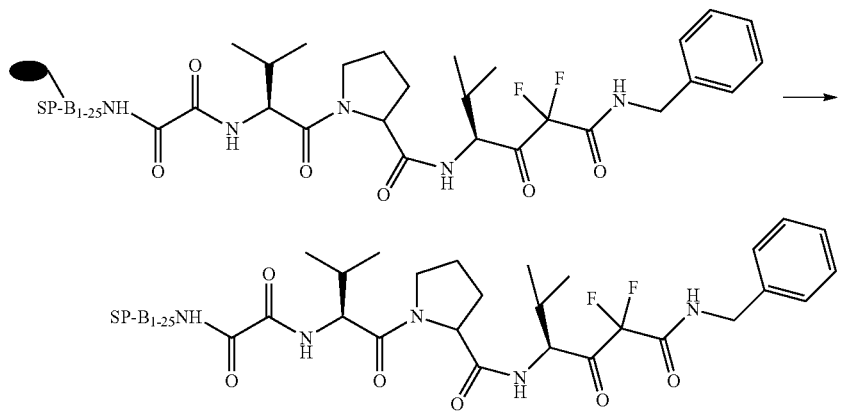

Procedure for making the cleavage solution. TFA (81%), Phenol (5%), Thioanisole (5%), 1,2,Ethanedithiol (2.5%), Water (3%), Dimethylsulphide (2%), ammonium iodide (1.5%). To the resin was added the cleavage solution and was allowed to shake on a shaker for about 3 h. The resin was filtered through cotton and washed with TFA. The filtrate was then concentrated under vacuum and triturated with cold ether to give a white solid, which was then purified by preparative HPLC to give the desired product. LCMS (M/3): 1155; Yield: 46 mg (1.84%).

Example 3

Synthesis of Target C

Stage-6

Scheme 11

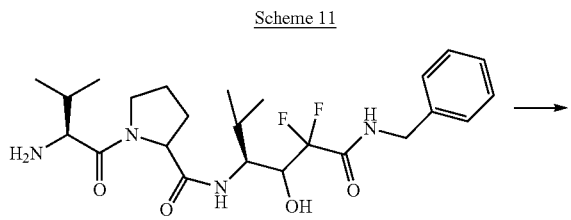

-continued

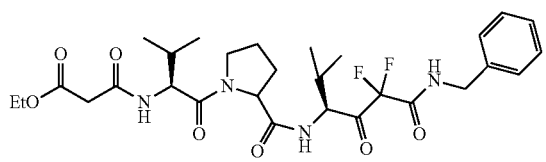

To a solution of stage-5 (3.2 g, 6.6 mmol) in dry THF (50 mL) at room temperature was added mono ethyl malonate (0.7 mL, 6 mmol) followed by HOBT (1.63 g, 12 mmol), EDCI (1.27 g, 6.6 mmol) and N-methyl morpholine (1.6 mL, 15 mmol). The reaction mixture was then allowed to stir at room temperature for 4 h. The reaction mixture was then quenched with water and evaporated under reduced pressure in order to remove THF. The aqueous layer was then extracted with ethyl acetate (100 mL). The organic layer was dried over sodium sulphate and concentrated to give the crude product which was then purified by preparative HPLC (0.98 g). HPLC Rt: 6.44; LCMS (M+1): 596; Yield: 25% After prep.

Stage-7

Scheme 12

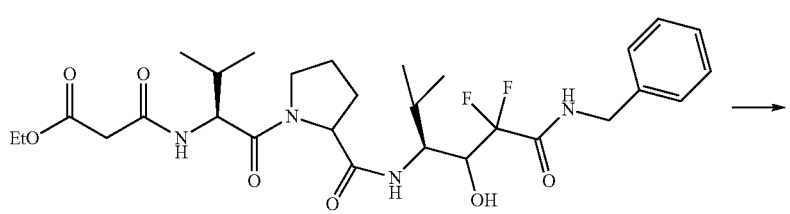

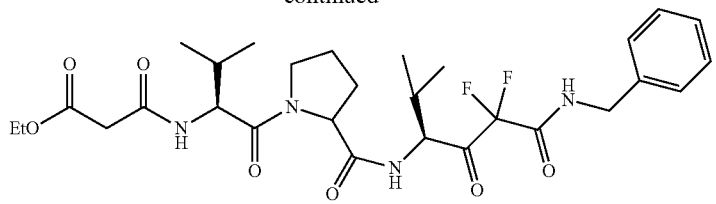

Trifluoroacetic acid (0.45 mL, 5.7 mmol) was added to a stirred solution of stage-6 (0.86 g, 1.45 mmol) and Dess-Martin periodinane (2.46 g, 5.7 mmol) in dry dichloromethane (30 mL). The mixture was stirred for 4 h at room temperature under nitrogen atmosphere. Ethyl acetate (50 mL) was added and the mixture was washed with saturated sodium thiosulphate (20 mL), saturated NaHCO$_3$ (20 mL) and brine (20 mL). The organic layer was dried over sodium sulphate, filtered, and the solvent was removed under vacuum to give the desired product (0.74 g). HPLC Rt: 7.05; LCMS (M+1): 595; Yield: 86%.

Stage-8

Scheme 13

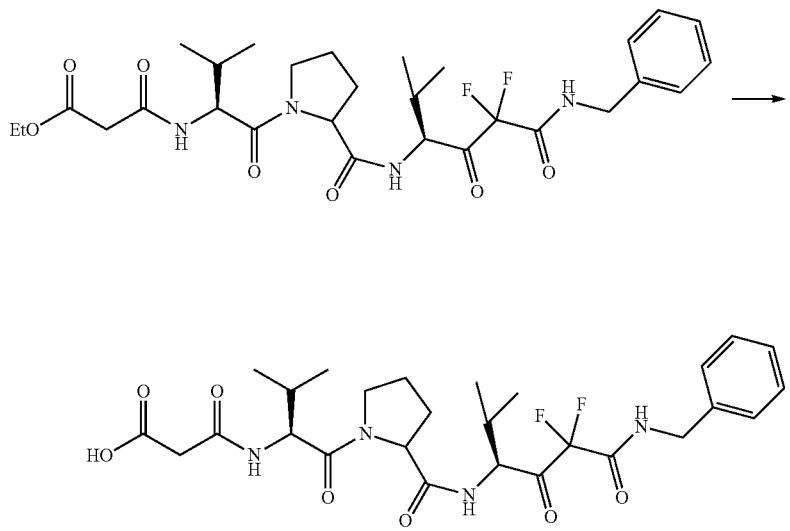

A solution of stage-7 (0.75 g, 1.2 mmol) in methanol water 1:1 (5 mL:5 mL) was treated with 1N NaOH (0.060 g, 1.5 mmol) and stirred at room temperature for 4 h. The reaction mixture was concentrated to remove methanol, acidified with 1N HCl (till pH 2) and extracted with ethyl acetate (50 mL). The organic layer was dried over sodium sulphate and concentrated under reduced pressure to give the desired product, which was then purified by preparative HPLC (0.4 g). HPLC Rt: 6.01-6.51; LCMS (M+1): 567; Yield: 56% After prep.

Stage-9

Scheme 14

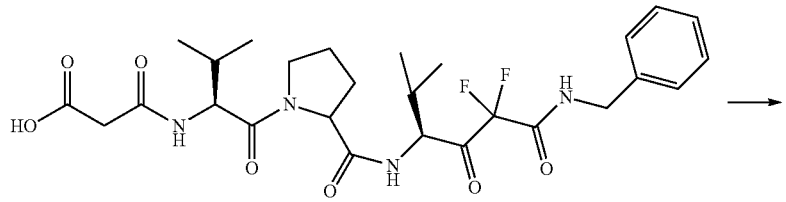

Wang resin (2 g, 0.08 mmol) was treated with 20% piperidine in DMF (20 mL) and stirred for about an hour. It was then washed with DMF (2 times), DCM (3 times) and then dried under reduced pressure. Kaiser test was performed on the resin to ensure complete removal of F-moc group. Then it was used for coupling with the stage -8. To a solution of the resin (2 g, 0.08 mmol) in DMF (5 mL) was added a solution of the above acid (0.1 g, 0.16 mmol) in DMF (3 mL), followed by the addition of PyBoP(0.83 g, 0.16 mmol) and N-methyl morpholine (0.2 mL, 0.2 mmol). The reaction mixture was allowed to shake on a shaker for about 3 h. The solution was decanted, fresh lots of the above reagents were again added and it was further allowed to shake for 3 h. This process was repeated for about 4 times. The solution was decanted, and the resin was washed with DMF (3 times), DCM (3 times) dried under reduced pressure. Kaiser test was performed on the resin to ensure that the coupling has taken place.

Stage-10

Procedure for making the cleavage solution. TFA (81%), Phenol (5%), Thioanisole (5%), 1,2,Ethanedithiol (2.5%), Water (3%), Dimethylsulphide (2%), ammonium iodide (1.5%). To the resin was added the cleavage solution (25 mL) and was allowed to shake on a shaker for about 3 h. The resin was filtered through cotton and washed with TFA. The filtrate was then concentrated under reduced pressure and triturated with cold ether to give a white solid, which was then purified by preparative HPLC to give the desired product (0.080 g). LCMS (M/3): 1160; Yield: 2.4%.

Example 4

Bronchoaveolar Lavage of the Lungs following HNE Exposure

A total of 14 animals were used in this study. Anesthetized mice received 0.1 ml of solution delivered by a blunt tip catheter to the opening of the trachea and the animals allowed to aspirate the solution into their lungs (this method is also referred to as intratracheal instillation). All animals were exposed to the treatment for 2 hours and re-anesthetized. Bronchoalveolar lavage of the lungs was performed as described below. The four animals given HNE (the causative agent of emphysema) had an average lung blood cell level by weight of 0.053 grams. Target 2 (a potent HNE inhibitor developed by Zeneca in the early 1990s) when given with the HNE, reduced the average blood level in the lungs by 34% to 0.035 grams. Target C (the Zeneca molecule covalently attached to the N-terminus of the first 25 residues of the human surfactant B peptide) when given with the HNE reduced the average blood level in the lungs by 87% to 0.007 grams.

A set of animals was used to determine the optimal concentration of HNE for the study. An initial sample exposed to 50 micrograms of HNE did not survive exposure. The amount of HNE was reduced to 40 micrograms to maintain a maximal detrimental but survivable effect. The animals exposed to 40 micrograms of HNE were able to survive long enough to perform the complete study. All animals remaining in the complete study were exposed to 40 micrograms of HNE.

Target 2 (the Zeneca molecule) was given in a 70-fold molar excess relative to HNE. In the kinetic studies, Target 2 has 2 nM affinity. Target C (the Zeneca molecule covalently attached to the first 25 residues of the human surfactant peptide B) loses approximately two orders of magnitude of potency as compared to Target 2 in the kinetic studies and thus Target C has approximately 200 nM affinity for HNE. Accordingly, the Target C was given to the animals in a 100 fold molar excess relative to HNE in these studies.

Bronchio-Alveolar lavage (BAL) is performed by 1) anesthetizing the animals; 2) performing a tracheotomy on the animals and cutting open the chest and spreading the ribs to enable full lung expansion; 3) pressurizing 1 ml of PBS buffer solution into the lungs through the tracheotomy catheter; 4)

sucking the solution out of the lungs; 5) centrifuging the recovered solution to separate the red blood cell fraction from the liquid fraction; and 6) weighing the red blood cell fraction.

TABLE 2

Lung Blood Cell Level Measurements

| Treatment | Mouse group 1 | Mouse group 2 | Mouse group 3 | Mouse Group 4 | Group mean |
|---|---|---|---|---|---|
| PBS/DMSO | 0 | 0 | 0 | Not done | 0 |
| HNE/DMSO | 0.09 g | 0.049 g | 0.021 g | 0.051 g | 0.053 g |
| Target 2 + HNE | 0.03 g | 0.041 g | 0.03 g | 0.039 g | 0.035 g |
| Target C + HNE | 0 | 0.007 g | 0.014 g | Not done | 0.007 g |

Example 5

Intratracheal Delivery of HNE, HNE mixed with Zeneca Inhibitor, and HNE mixed with Zeneca Inhibitor Linked to a Lung Surfactant Peptide A total of 42 animals were used in this study. Anesthesized mice received 0.1 ml of solution delivered by intratracheal instillation as described above in Example 4. Animals were divided into the following treatment groups: four animals received saline only; ten animals received HNE only; four animals received the Zeneca inhibitor (target 2) only; eight animals received HNE mixed with the Zeneca inhibitor (target 2); eight animals received Zeneca inhibitor linked to a lung surfactant peptide (target C) only; and eight animals received HNE mixed with Zeneca inhibitor linked to a lung surfactant peptide (target C). Animals receiving HNE were instilled with 40 micrograms HNE. Target 2 (Zeneca inhibitor) was administered in a 70-fold molar excess relative to HNE and Target C (Zeneca inhibitor linked to a lung surfactant peptide) was administered in a 100 fold molar excess relative to HNE as described in Example 4.

All animals were observed a four week period prior to sacrifice following IRB approved protocols and the lungs from each animal were removed for sectioning. The Hilar and central region was sectioned from the left lung and the caudal region was sectioned from the right lung of each animal. Lung sections were scored using blind-scoring by an expert as "E" for emphysema and "N" for no emphysema.

Figure 22:
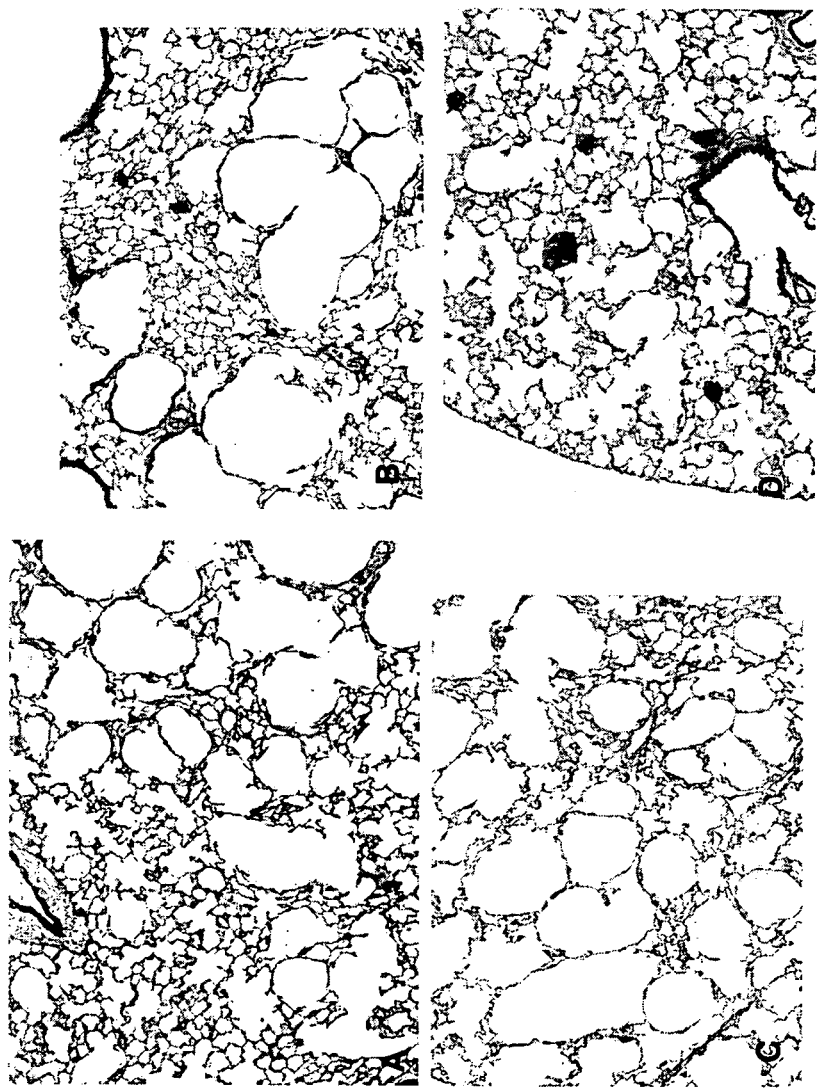
Figure 23:
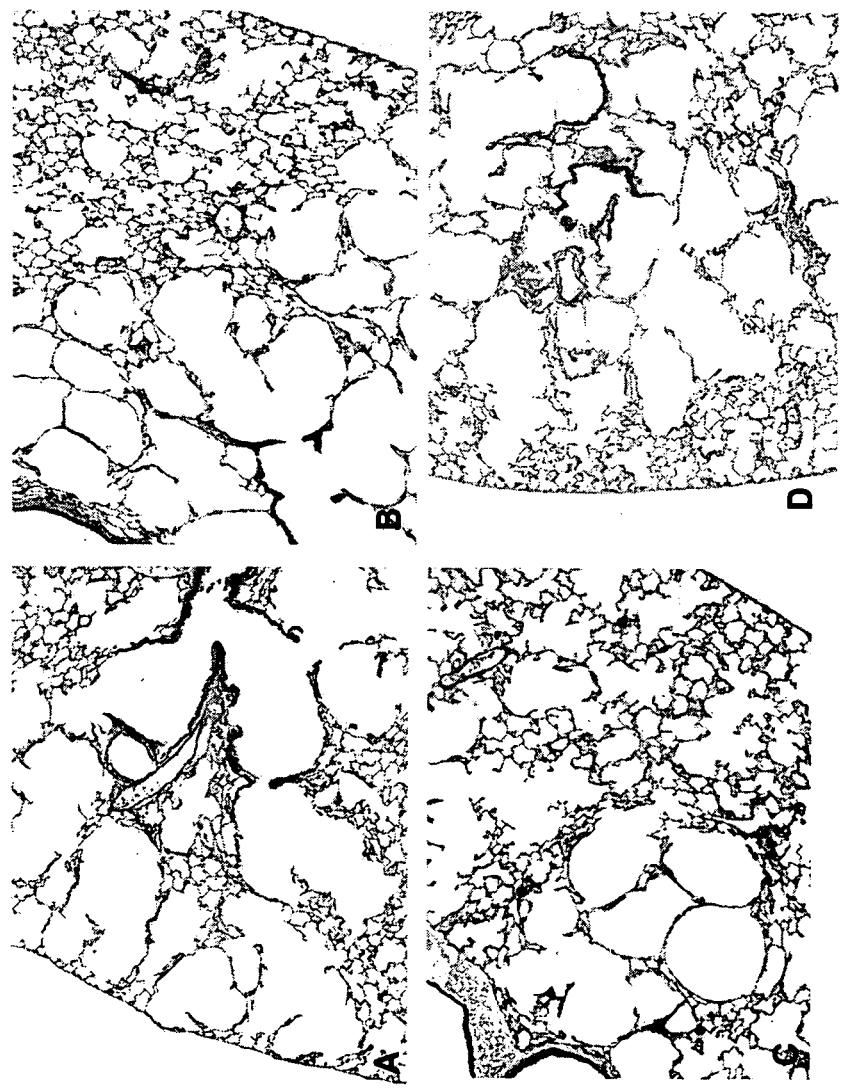
Figure 24:
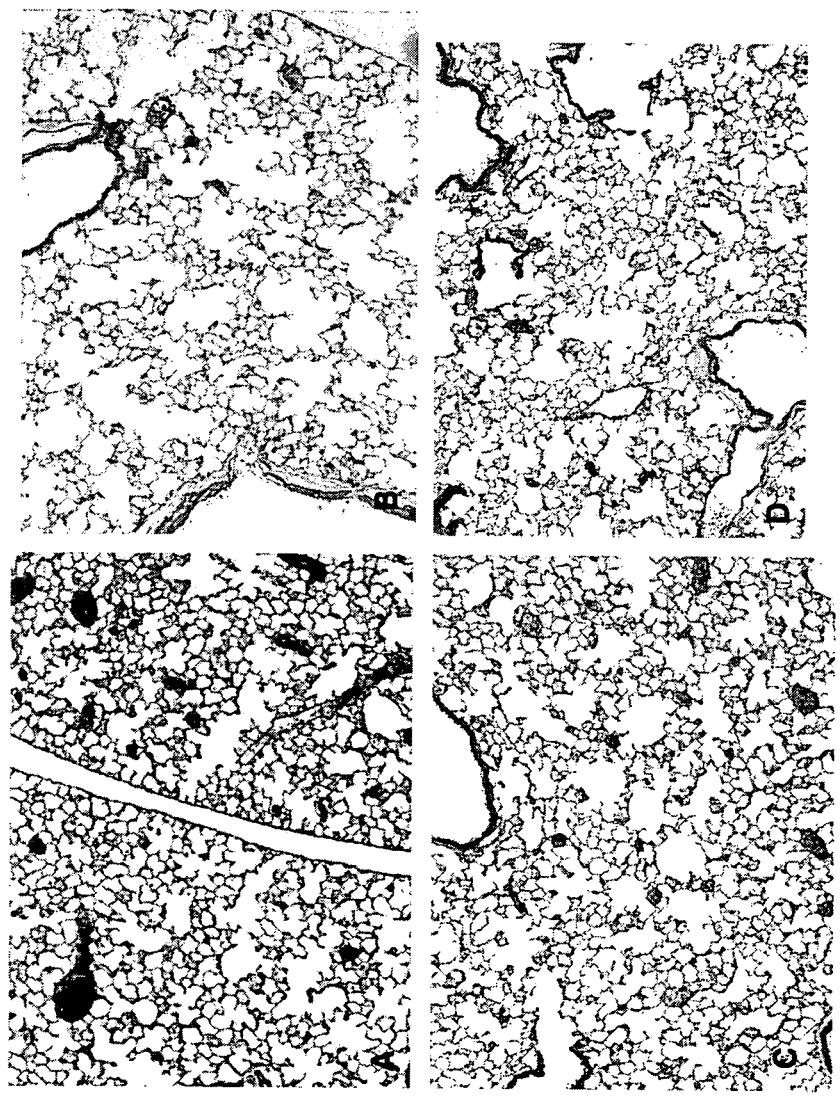
Figure 25:
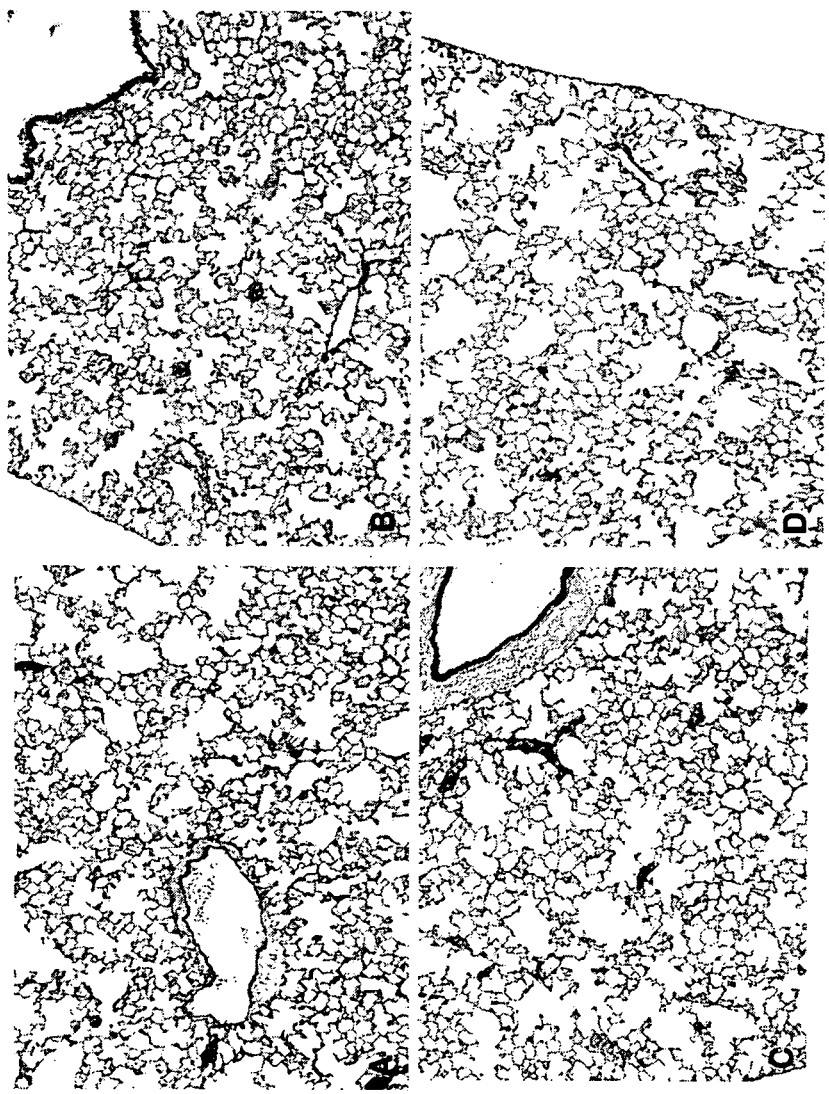

Target 2 (the Zeneca inhibitor) had no effect on HNE induced emphysema (compare FIG. 23, which shows lung histology sections of mice instilled with HNE and Zeneca inhibitor, with FIG. 22, which shows lung histology sections of mice with HNE induced emphysema). In contrast, target C (the Zeneca inhibitor covalently attached to a lung surfactant peptide) strongly inhibited HNE induced emphysema (compare FIG. 25, which shows lung histology sections of mice instilled with HNE and Zeneca inhibitor linked to a lung surfactant peptide with FIG. 22). Further, lung histology sections from animals instilled with HNE and target C (Zeneca inhibitor linked to a lung surfactant peptide) could not be distinguished in blind scoring from lung histology sections from animals receiving saline only (compare FIG. 25 with FIG. 24).

The distance between adjacent alveolar walls was also measured to quantitate the degree of lung destruction for each treatment group. Lung sections obtained from each animal were analyzed under a microscope (which is connected to a computer) and lines were drawn over the lung sections between adjacent alveolar walls. The distance along the lines was calculated to determine the average distance or mean linear intercept (MLI) between adjacent alveolar walls. An increase in the average distance between adjacent alveolar walls corresponds to an increase in lung destruction.

As shown in Table 3 below, exposure with HNE increased the MLI compared to the negative control (saline only) treatment group. Target 2 had no effect on HNE induced emphysema (HNE+Target 2), whereas target C(HNE+Target C) strongly inhibited HNE induced emphysema (i.e., shows a decrease in MLI compared to HNE only exposure and returns to the saline only baseline). Target 2 only and Target C only are negative controls.

TABLE 3

Distance between Adjacent Alveolar Wall Measurements

| Treatment Group | Animals (N) | MLI (µm) | Standard Deviation |
|---|---|---|---|
| Saline only | 4 | 44.40 | 6.50 |
| HNE only | 10 | 51.45 | 5.78 |
| Target 2 only | 4 | 43.27 | 3.82 |
| HNE + Target 2 | 8 | 53.27 | 8.27 |
| Target C only | 8 | 40.94 | 1.59 |
| HNE + Target C | 8 | 45.82 | 3.30 |

Incorporation by Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

TABLE 1

Exemplary human SP-B peptides (C-terminal truncations)

| Human SP-B peptides | SEQ ID NO |
|---|---|
| FPIPLPYCWLCRALIKRIQAMIPKGALAVAVAQVCRVVPLVAGGICQCLA ERYSVILLDTLLGRMLPQLVCRLVLRC | SEQ ID NO: 36 |
| FPIPLPYCWLCRALIKRIQAMIPKGALAVAVAQVCRVVPLVAGGICQCLA ERYSVILLDTLLGRMLPQLVCRLVLR | SEQ ID NO: 37 |
| FPIPLPYCWLCRALIKRIQAMIPKGALAVAVAQVCRVVPLVAGGICQCLA ERYSVILLDTLLGRMLPQLVCRLVL | SEQ ID NO: 38 |

TABLE 1-continued

Exemplary human SP-B peptides (C-terminal truncations)

| Human SP-B peptides | SEQ ID NO |
|---|---|
| FPIPLPYCWLCRALIKRIQAMIPKGALAVAVAQVCRVVPLVAGGICQCLA ERYSVILLDTLLGRMLPQLVCRLV | SEQ ID NO: 39 |
| FPIPLPYCWLCRALIKRIQAMIPKGALAVAVAQVCRVVPLVAGGICQCLA ERYSVILLDTLLGRMLPQLVCRL | SEQ ID NO: 40 |
| FPIPLPYCWLCRALIKRIQAMIPKGALAVAVAQVCRVVPLVAGGICQCLA ERYSVILLDTLLGRMLPQLVCR | SEQ ID NO: 41 |
| FPIPLPYCWLCRALIKRIQAMIPKGALAVAVAQVCRVVPLVAGGICQCLA ERYSVILLDTLLGRMLPQLVC | SEQ ID NO: 42 |
| FPIPLPYCWLCRALIKRIQAMIPKGALAVAVAQVCRVVPLVAGGICQCLA ERYSVILLDTLLGRMLPQLV | SEQ ID NO: 43 |
| FPIPLPYCWLCRALIKRIQAMIPKGALAVAVAQVCRVVPLVAGGICQCLA ERYSVILLDTLLGRMLPQL | SEQ ID NO: 44 |
| FPIPLPYCWLCRALIKRIQAMIPKGALAVAVAQVCRVVPLVAGGICQCLA ERYSVILLDTLLGRMLPQ | SEQ ID NO: 45 |
| FPIPLPYCWLCRALIKRIQAMIPKGALAVAVAQVCRVVPLVAGGICQCLA ERYSVILLDTLLGRMLP | SEQ ID NO: 46 |
| FPIPLPYCWLCRALIKRIQAMIPKGALAVAVAQVCRVVPLVAGGICQCLA ERYSVILLDTLLGRML | SEQ ID NO: 47 |
| FPIPLPYCWLCRALIKRIQAMIPKGALAVAVAQVCRVVPLVAGGICQCLA ERYSVILLDTLLGRM | SEQ ID NO: 48 |
| FPIPLPYCWLCRALIKRIQAMIPKGALAVAVAQVCRVVPLVAGGICQCLA ERYSVILLDTLLGR | SEQ ID NO: 49 |
| FPIPLPYCWLCRALIKRIQAMIPKGALAVAVAQVCRVVPLVAGGICQCLA ERYSVILLDTLLG | SEQ ID NO: 50 |
| FPIPLPYCWLCRALIKRIQAMIPKGALAVAVAQVCRVVPLVAGGICQCLA ERYSVILLDTLL | SEQ ID NO: 51 |
| FPIPLPYCWLCRALIKRIQAMIPKGALAVAVAQVCRVVPLVAGGICQCLA ERYSVILLDTL | SEQ ID NO: 52 |
| FPIPLPYCWLCRALIKRIQAMIPKGALAVAVAQVCRVVPLVAGGICQCLA ERYSVILLDT | SEQ ID NO: 53 |
| FPIPLPYCWLCRALIKRIQAMIPKGALAVAVAQVCRVVPLVAGGICQCLA ERYSVILLD | SEQ ID NO: 54 |
| FPIPLPYCWLCRALIKRIQAMIPKGALAVAVAQVCRVVPLVAGGICQCLA ERYSVILL | SEQ ID NO: 55 |
| FPIPLPYCWLCRALIKRIQAMIPKGALAVAVAQVCRVVPLVAGGICQCLA ERYSVIL | SEQ ID NO: 56 |
| FPIPLPYCWLCRALIKRIQAMIPKGALAVAVAQVCRVVPLVAGGICQCLA ERYSVI | SEQ ID NO: 57 |
| FPIPLPYCWLCRALIKRIQAMIPKGALAVAVAQVCRVVPLVAGGICQCLA ERYSV | SEQ ID NO: 58 |
| FPIPLPYCWLCRALIKRIQAMIPKGALAVAVAQVCRVVPLVAGGICQCLA ERYS | SEQ ID NO: 59 |
| FPIPLPYCWLCRALIKRIQAMIPKGALAVAVAQVCRVVPLVAGGICQCLA ERY | SEQ ID NO: 60 |
| FPIPLPYCWLCRALIKRIQAMIPKGALAVAVAQVCRVVPLVAGGICQCLA ER | SEQ ID NO: 61 |
| FPIPLPYCWLCRALIKRIQAMIPKGALAVAVAQVCRVVPLVAGGICQCLA E | SEQ ID NO: 62 |
| FPIPLPYCWLCRALIKRIQAMIPKGALAVAVAQVCRVVPLVAGGICQCLA | SEQ ID NO: 63 |
| FPIPLPYCWLCRALIKRIQAMIPKGALAVAVAQVCRVVPLVAGGICQCL | SEQ ID NO: 64 |

TABLE 1-continued

Exemplary human SP-B peptides (C-terminal truncations)

| Human SP-B peptides | SEQ ID NO |
|---|---|
| FPIPLPYCWLCRALIKRIQAMIPKGALAVAVAQVCRVVPLVAGGICQC | SEQ ID NO: 65 |
| FPIPLPYCWLCRALIKRIQAMIPKGALAVAVAQVCRVVPLVAGGICQ | SEQ ID NO: 66 |
| FPIPLPYCWLCRALIKRIQAMIPKGALAVAVAQVCRVVPLVAGGIC | SEQ ID NO: 67 |
| FPIPLPYCWLCRALIKRIQAMIPKGALAVAVAQVCRVVPLVAGGI | SEQ ID NO: 68 |
| FPIPLPYCWLCRALIKRIQAMIPKGALAVAVAQVCRVVPLVAGG | SEQ ID NO: 69 |
| FPIPLPYCWLCRALIKRIQAMIPKGALAVAVAQVCRVVPLVAG | SEQ ID NO: 70 |
| FPIPLPYCWLCRALIKRIQAMIPKGALAVAVAQVCRVVPLVA | SEQ ID NO: 71 |
| FPIPLPYCWLCRALIKRIQAMIPKGALAVAVAQVCRVVPLV | SEQ ID NO: 72 |
| FPIPLPYCWLCRALIKRIQAMIPKGALAVAVAQVCRVVPL | SEQ ID NO: 73 |
| FPIPLPYCWLCRALIKRIQAMIPKGALAVAVAQVCRVVP | SEQ ID NO: 74 |
| FPIPLPYCWLCRALIKRIQAMIPKGALAVAVAQVCRVV | SEQ ID NO: 75 |
| FPIPLPYCWLCRALIKRIQAMIPKGALAVAVAQVCRV | SEQ ID NO: 76 |
| FPIPLPYCWLCRALIKRIQAMIPKGALAVAVAQVCR | SEQ ID NO: 77 |
| FPIPLPYCWLCRALIKRIQAMIPKGALAVAVAQVC | SEQ ID NO: 78 |
| FPIPLPYCWLCRALIKRIQAMIPKGALAVAVAQV | SEQ ID NO: 79 |
| FPIPLPYCWLCRALIKRIQAMIPKGALAVAVAQ | SEQ ID NO: 80 |
| FPIPLPYCWLCRALIKRIQAMIPKGALAVAVA | SEQ ID NO: 81 |
| FPIPLPYCWLCRALIKRIQAMIPKGALAVAV | SEQ ID NO: 82 |
| FPIPLPYCWLCRALIKRIQAMIPKGALAVA | SEQ ID NO: 83 |
| FPIPLPYCWLCRALIKRIQAMIPKGALAV | SEQ ID NO: 84 |
| FPIPLPYCWLCRALIKRIQAMIPKGALA | SEQ ID NO: 85 |
| FPIPLPYCWLCRALIKRIQAMIPKGAL | SEQ ID NO: 86 |
| FPIPLPYCWLCRALIKRIQAMIPKGA | SEQ ID NO: 87 |
| FPIPLPYCWLCRALIKRIQAMIPKG | SEQ ID NO: 88 |
| FPIPLPYCWLCRALIKRIQAMIPK | SEQ ID NO: 89 |
| FPIPLPYCWLCRALIKRIQAMIP | SEQ ID NO: 90 |
| FPIPLPYCWLCRALIKRIQAMI | SEQ ID NO: 91 |
| FPIPLPYCWLCRALIKRIQAM | SEQ ID NO: 92 |
| FPIPLPYCWLCRALIKRIQA | SEQ ID NO: 93 |

I claim:

1. A method of treating a human suffering from or at risk of a lung disease, the method comprising:
providing a conjugate comprising a pulmonary active drug for lung treatment selected from the group consisting of an antihistamines; a P2X agonist; a P2Y agonist; a matrix metalloproteinase inhibitors; a kinase inhibitor; an endothelin receptor antagonist; a prostacyclin analogue selected from the group consisting of beraprost, epoprostenol, iloprost, and treprostinil; and a phosphodiesterase type 5 inhibitor; wherein said pulmonary active drug is covalently bonded to a surface active agent characterized by an affinity for the human alveolar/gas interface and comprising at least a portion of a mammalian lung surfactant polypeptide substantially non-immunogenic to humans, wherein the pulmonary active drug binds to an extracellular or cell surface-bound target accessible to the human alveolar/gas interface when the conjugate is present at the interface; and
administering the conjugate to the human by inhalation in an amount effective to induce a drug effect in the lungs, wherein said administration increases residence time of the pulmonary active drug in the lung relative to inhalation administration of unconjugated pulmonary active drug.

2. The method of claim 1 wherein said administration reduces systemic bioavailability of the pulmonary active drug relative to inhalation administration of unconjugated pulmonary active drug.

3. A method of adapting a pulmonary active drug to improve its lung pharmacodynamic bioavailability comprising:
covalently bonding the pulmonary active drug to a surface active agent to produce a pulmonary active drug conjugate, the surface active agent being characterized by an affinity for the human alveolar/gas interface and comprising at least a portion of a mammalian lung surfactant polypeptide, the conjugate having an increased concentration or an increased residence time in the lung relative to the pulmonary active drug administered by inhalation at the same concentration as the conjugate, wherein the pulmonary active drug binds to an extracellular or cell surface-bound target accessible to the human alveolar/gas interface when the conjugate is present at the interface;

wherein the pulmonary active drug is selected from the group consisting of: an antihistamine; a P2X agonist; a P2Y agonist; a matrix metalloproteinase inhibitor; a kinase inhibitor; an endothelin receptor antagonist; a prostacyclin analogue selected from the group consisting of beraprost, epoprostenol, iloprost, and treprostinil; and a phosphodiesterase type 5 inhibitor.

4. The method of claim 1, wherein the administration step is repeated once daily, every other day, every three days, every five days, biweekly, or weekly.

5. The method of claim 1, wherein the administration step is conducted using an inhalation device.

6. The method of claim 1, wherein the surface active agent comprises a human lung surfactant polypeptide, a non-human mammalian lung surfactant, or a portion thereof.

7. The method of claim 6, wherein the surface active agent comprises at least a portion of SP-A, SP-B, SP-C, SP-D, or a mixture thereof.

8. The method of claim 6, wherein the surface active agent comprises at least a portion of SP-B.

9. The method of claim 1, wherein the surface active agent comprises or is derived from a mammalian lung surfactant harvested from the lungs of a mammal.

10. The method of claim 1, wherein said surface active agent comprises a peptide selected from the group consisting of SEQ ID Nos. 36 through 93.

11. The method of claim 1, wherein the pulmonary active drug is an antihistamine selected from the group consisting of acrivastine, astemizole, azatadine, azelastine, brompheniramine, cetirizine, chlorpheniramine, cyclizine, cyproheptadine, diphehydramine, desloratidine, fexofenadine, hydroxyzine, levocetirizine, loratidine, meclizine, mepyramine, methscopolamine, misolastine, phenidamine, promethazine, pyrilamine, tecastemizole, and terfenadine.

12. The method of claim 1, wherein the pulmonary active drug is an P2Y agonist selected from the group consisting of denufosol tetrasodium, ATP, and an ATP analogue.

13. The method of claim 1, wherein the pulmonary active drug is a matrix metalloproteinase inhibitor.

14. The method of claim 1, wherein the pulmonary active drug is a kinase inhibitor selected from the group consisting of gefitinib and erlotinib.

15. The method of claim 1, wherein the pulmonary active drug is an endothelin receptor antagonist selected from the group consisting of tezosentan, bosentan, sitaxentan, ambrisentan, and atrasentan.

16. The method of claim 1, wherein the pulmonary active drug is a phophodiesterase type 5 inhibitor selected from the group consisting of sildenafil, tadalafil, and vardenafil.

17. The method of claim 1, wherein the surface active agent is covalently attached directly to the pulmonary active drug.

18. The method of claim 1, wherein the surface active agent is covalently attached to the pulmonary active drug by a linker comprising an amide, ester, urea, carbamate, ether, thioether, disubstituted amine, or trisubstituted amine.

19. The method of claim 1, wherein the pulmonary active drug is covalently attached to the C-terminus of the mammalian lung surfactant polypeptide of the surface active agent through an amide bond formed through an amino group of the drug and a carboxylic acid group of the surfactant polypeptide.

20. The method of claim 3, wherein the surface active agent comprises a human lung surfactant polypeptide, a non-human mammalian lung surfactant, or a fraction thereof.

21. The method of claim 20, wherein the surface active agent comprises at least a portion of SP-A, SP-B, SP-C, SP-D, or a mixture thereof.

22. The method of claim 20, wherein the surface active agent comprises at least a portion of SP-B.

23. The method of claim 3, wherein said surface active agent comprises a peptide selected from the group consisting of SEQ ID Nos. 36 through 93.

24. The method of claim 3, wherein the surface active agent is covalently attached directly to the pulmonary active drug.

25. The method of claim 3, wherein the surface active agent is covalently attached to the pulmonary active drug by a linker comprising an amide, ester, urea, carbamate, ether, thioether, disubstituted amine, or trisubstituted amine.

26. The method of claim 3, wherein the pulmonary active drug is covalently attached to the N-terminus of the mammalian lung surfactant polypeptide of the surface active agent through an amide bond formed through a carboxyl group of the drug and an amino group of the surfactant polypeptide.

27. The method of claim 3, wherein the pulmonary active drug is covalently attached to the C-terminus of the mammalian lung surfactant polypeptide of the surface active agent through an amide bond formed through an amino group of the drug and a carboxylic acid group of the surfactant polypeptide.

28. The method of claim 3, wherein the pulmonary active drug is covalently attached to the mammalian lung surfactant polypeptide of the surface active agent through a linker attached to an oxygen atom of the hydroxyl group of the drug and a carbonyl-carbon atom of the carboxylic acid group of the surfactant polypeptide.

* * * * *